(12) United States Patent
Dahiyat et al.

(10) Patent No.: US 6,746,853 B1
(45) Date of Patent: Jun. 8, 2004

(54) PROTEINS WITH INSULIN-LIKE ACTIVITY USEFUL IN THE TREATMENT OF DIABETES

(75) Inventors: Bassil I. Dahiyat, Los Angeles, CA (US); Andrew G. Morton, deceased, late of Mt. Lebanon, PA (US), by Bassil I. Dahiyat, legal representative

(73) Assignee: Xencor, Inc., Monrovia, CA (US)

( * ) Notice: Subject to any disclaimer, the term of this patent is extended or adjusted under 35 U.S.C. 154(b) by 0 days.

(21) Appl. No.: 09/574,443

(22) Filed: May 19, 2000

Related U.S. Application Data
(60) Provisional application No. 60/134,930, filed on May 19, 1999.

(51) Int. Cl.[7] .................. A61K 38/28; C12N 15/17; C12N 15/63; C12N 1/21; C07K 1/21
(52) U.S. Cl. ............... 435/69.1; 435/69.4; 435/243; 435/320.1; 435/325; 514/3; 530/303; 536/23.5
(58) Field of Search .................... 514/3; 530/303; 435/69.1, 320.1, 69.4, 325, 243; 536/235

(56) References Cited

U.S. PATENT DOCUMENTS

| | | | |
|---|---|---|---|
| 4,421,685 A | | 12/1983 | Chance et al. |
| 4,992,417 A | | 2/1991 | Katsoyannis et al. |
| 5,008,241 A | | 4/1991 | Markussen et al. |
| 5,506,202 A | | 4/1996 | Vertesy et al. |
| 5,514,646 A | | 5/1996 | Chance et al. |
| 5,559,094 A | | 9/1996 | Brems et al. |
| 5,618,913 A | * | 4/1997 | Brange et al. |
| 5,621,073 A | | 4/1997 | Dickhardt et al. |
| 5,663,291 A | | 9/1997 | Obermeier et al. |
| 5,700,662 A | | 12/1997 | Chance et al. |
| 6,034,054 A | | 3/2000 | DeFelippis et al. |

FOREIGN PATENT DOCUMENTS

| | | |
|---|---|---|
| WO | 93/03174 | 2/1993 |
| WO | 00/23564 | 4/2000 |

OTHER PUBLICATIONS

Kristensen et al, J. Biol. Chem. 272(20): 12978–12983, 1997.*
Marki et al. Hoppe–Seyler's Z. Physiol. Chem. 360(11): 1619–1632, 1979.*
Mirmira et al. J. Biol. Chem. 266(3): 1428–1436, 1991.*
Nakagawa et al. J. Biol. Chem. 261(16): 7332–7341, 1986.*
Marki et al., "Synthesis and Biological Activity of Seventeen Analogues of Human Insulin", *Hoppe Seylers Z. Phsiol. Chem.* 360(11):1619–32 (1979).
Hu et al., "Steric Requirements at Position B12 for High Biological Activity in Insulin", *Biochemistry* 32(10):2631–5 (1993).
Schwartz et al., A superactive insulin: [B10–Aspartic acid] insulin(human), *Proc. Natl. Acad. Sci. USA* 84(18):6408–11 (1987).

Kitagawa et al., "Critical Role of the $A^2$ Amino Acid Residue in the Biological Activity of Insulin: [2–Glycine–A]– and [2–Alanine–A]insulins", *Biochemistry* 23(7):1405–13 (1984).
Kobayashi et al., "Supernormal Insulin:[D–Phe$^{B24}$]–Insulin With Increased Affinity for Insulin Receptors", *Biochem. Biophys. Res. Commun.* 107(1):329–36 (1982).
Shoelson et al., "Mutations at the Dimer, Haxamer, and Receptor–Binding Surfaces of Insulin Independently Affect Insulin–Insulin and Insulin–receptor Interactions", *Biochemistry* 31(6):1757–67 (1992).
Blundell et al., "Insulin: The Structure in the Crystal and Its Reflection in Chemistry and Biology", in *Advances in Protein Chemistry*, Academic Press, New York and London, vol. 26, pp279–330 (1972).
Binder, "Insulin Pharmacokinetics", *Diabetes Care* 7(2):188–99 (1984).
Derewenda et al., "Phenol stabilizes more helix in a new symmetrical zinc insulin hexamer", *Nature* 338(6216):594–596 (1989).
Chothia et al., "Transmission of conformational change in insulin", *Nature* 302(5908):500–505 (1983).
Kruger, et al., "Cooperativity and Intermediate States in the T–R–Structureall Transformation of Insulin", *Biol. Chem. Hoppe–Seyler* 371(8):669–673 (1990).
Bentley et al., "Structure of insulin in 4–zinc insulin", *Nature* 261(5556):166–168 (1976).
Smith & Dodson, "The Structure of a Phombohedral $R_6$ Insulin Hexamer That Binds Phenol", *Biopolymers* 32(4):441–445 (1992).
Renscheidt et al., "A solution equivalent of the 2Zn–4Zn transformation of insulin in the crystal", *Eur. J. Biochem.* 142(1):7–14 (1984).
Brader et al., "Characterization of the R–state Insulin Hexamer and Its derivatives. The Hexamer Is Stabilized by Heterotropic Ligand Binding Interactions", *Biochemistry* 30(27):6636–6645 (1991).
Frank et al., "Insulin and Proinsulin Conformaton in Solution", *Diabetes* 21(2):Suppl. 2:486–491 (1972).
Hua et al., "Receptor binding redefined by a structural switch in a mutant human insulin," *Nature* 354(6350):238–41 (1991).
Bao et al., "Crystal structure of desheptapeptide(B24–B30)insulin at 1.6 Å resolution: Implications for receptor binding", *Proc. Natl. Acad. Sci. USA* 94(7):2975–80 (1997).

(List continued on next page.)

*Primary Examiner*—Christine J. Saoud
(74) *Attorney, Agent, or Firm*—Dorsey & Whitney LLP; Robin M. Silva; Renee M. Kosslak

(57) ABSTRACT

The invention relates to novel insulin activity (IA) proteins and nucleic acids. The Invention further relates to the use of the IA proteins in the treatment of insulin related disorders such as type 1 diabetes and type 2 diabetes.

14 Claims, 10 Drawing Sheets

OTHER PUBLICATIONS

Brange et al., "Chemical Stability of Insulin. 1. Hydorlytic degredation During Storage of Pharmaceutical Preparations", *Pharm. Res.* 9(6):715–726 (1992).

Brange et al., "Chemical Stability of Insulin. 2. Formation of Higher Molecular Weight Transformation Products During Storage of Pharmaceutical Preparations", *Pharm. Res.* 9(6):727–734 (1992).

Brange & Langkjaer, "Chemical Stability if Insulin. 3. Influence of excipients. formulations, and pH", Acta Pharm. Nord.,4(3):149–158 (1992).

Hellinga et al., "Construction of New Ligand Binding Sites in Proteins of Known Structure; I. Computer–aided Modeling of Sites with Pre–defined Geometry", *J. Mol. Biol.* 222:763–785 (1991).

Hurley et al., "Design and Structural Analysis of Alternative Hydrophobic Core Packing Arrangements in Bacteriophage T4 Lysozyme", *J. Mol. Biol.* 224:1143–1154 (1992).

Desjarlais and Handel, "De novo design of the hydrophobic cores of proteins", *Protein Science* 4:2006–2018 (1995).

Harbury et al., "Repacing protein cores with backbone freedom: Structure prediction for coiled coils", *Proc. Natl. Acad. Sci.* USA 92:8408–8412 (1995).

Klemba et al., "Novel metal–binding proteins by design", *Struc. Biol.* 2(5):368–373 (1995).

Nautiyal, et al., "A Designed Heterotrimeric Coiled Coil", *Biochemistry* 34:11645–11651 (1995).

Betz and Grado, "Controlling Topology and Native–like Behavior fo de Novo–Designed Peptides: Design and Characterization of Antiparallel Four–Stranded Coiled Coils", *Biochemistry* 35:6955–6962 (1996).

Dahiyat and Mayo, "Protein Design automation", *Protein Science* 5:895–903 (1996).

Dahiyat and Mayo, "De Novo Protein Design: Fully Automated Sequence Selection", *Science* 278:82–87 (1997).

Dahiyat et al., "De Novo Protein Design: Towards Fully Automated Sequence Selection", *J. Mol. Biol.* 273:789–796 (1997).

Dahiyat et al., "Automated design of the surface positions of protein helices", *Protein Science* 6:1333–1337 (1997).

Jones, "De novo protein design using pairwise potentials and a genetic algorith", *Protein Science* 3:567–574 (1994).

Kono and Doi, "Energy Minimization Method Using Automata Network for Sequence and Side–Chain Conformation Prediction From Given Backbone Geometry", *Proteins: Structure, Function and Genetics* 19:244–255 (1994).

Database: CHEMABS, Acc. No. 130:192138, Chemical Abstracts Service: Columbus, Ohio. Chen et al., "Hydrophilic Thr can replace the hydrophobic and absolutely conservative A3Val in insulin," *Biochim. Biophys, Acta* (1998) 1429(1):69–73. (Abstract No. XP–002167130).

Database: CHEMABS, Acc. No. 128:149680, Chemical Abstracts Service: Columbus, Ohio. Shi et al., "Studies on growth–promoting action of insulin: mitogenic activity of insulin and its analogs in mouse mammary tumor cells," *Biochem. Mol. Biol. Int.* (1997) 43(4):705–711 (Abstract No. XP–002167131).

Database: CHEMABS, Acc. No. 115:85565 Chemical Abstracts Service: Columbus, Ohio. Brange et al., "Design of novel insulins with changed self–association and ligand binding properties," *GBF Monogr.* (1989) 12(Adv. Protein Des.):129–144 (Abstract No. XP–002167132).

Database: CHEMABS, Acc. No. 115:985 Chemical Abstracts Service: Columbus, Ohio. Sasaki et al., "Tertiary structure analysis of receptor binding ability of mutant insulins," *Jikeikai Med. J.* (1990) 37(3):343–353 (Abstract No. XP–002167133).

Nakagawa and Tager, "Importance of Aliphatic Side–Chain Structure at Positions 2 and 3 of the Insulin A Chain in Insulin–Receptor Interactions," *Biochemistry* (1992) 31(12):3204–3214.

* cited by examiner

1 MALWMRLLPL LALLALWGPD PAAAFVNGHL CGSHLVEALY LVCGERGFFY
51 TPKTRREAED LQVGQVELGG GPGAGSLQPL ALEGSLGKRG IVEQCCTSIC
101 SLYQLENYCN

FIG._1A

A-chain | B-chain
---|---

1 GIVEQCCTSI CSLYQLENYC NFVNQHLCGS HLVEALYLVC GERGFFYTPK T

FIG._1B

1TRZ:A

1 GIVEQCCTSI CSLYQLENYC N
    HHHHTTS     HHHHGGG

1TRZ:B

1 FVNQHLCGSH LVEALYLVCG ERGFFYTPKT
       S    HHH HHHHHHHHHG GG

1TRZ:C

1 GIVEQCCTSI CSLYQLENYC N
    HHHHSSS    HHHHGGG

1TRZ:D

1 FVNQHLCGSH LVEALYLVCG ERGFFYTPKT
     HHHHHHH HHHHHHHHHG GG S

FIG._1C

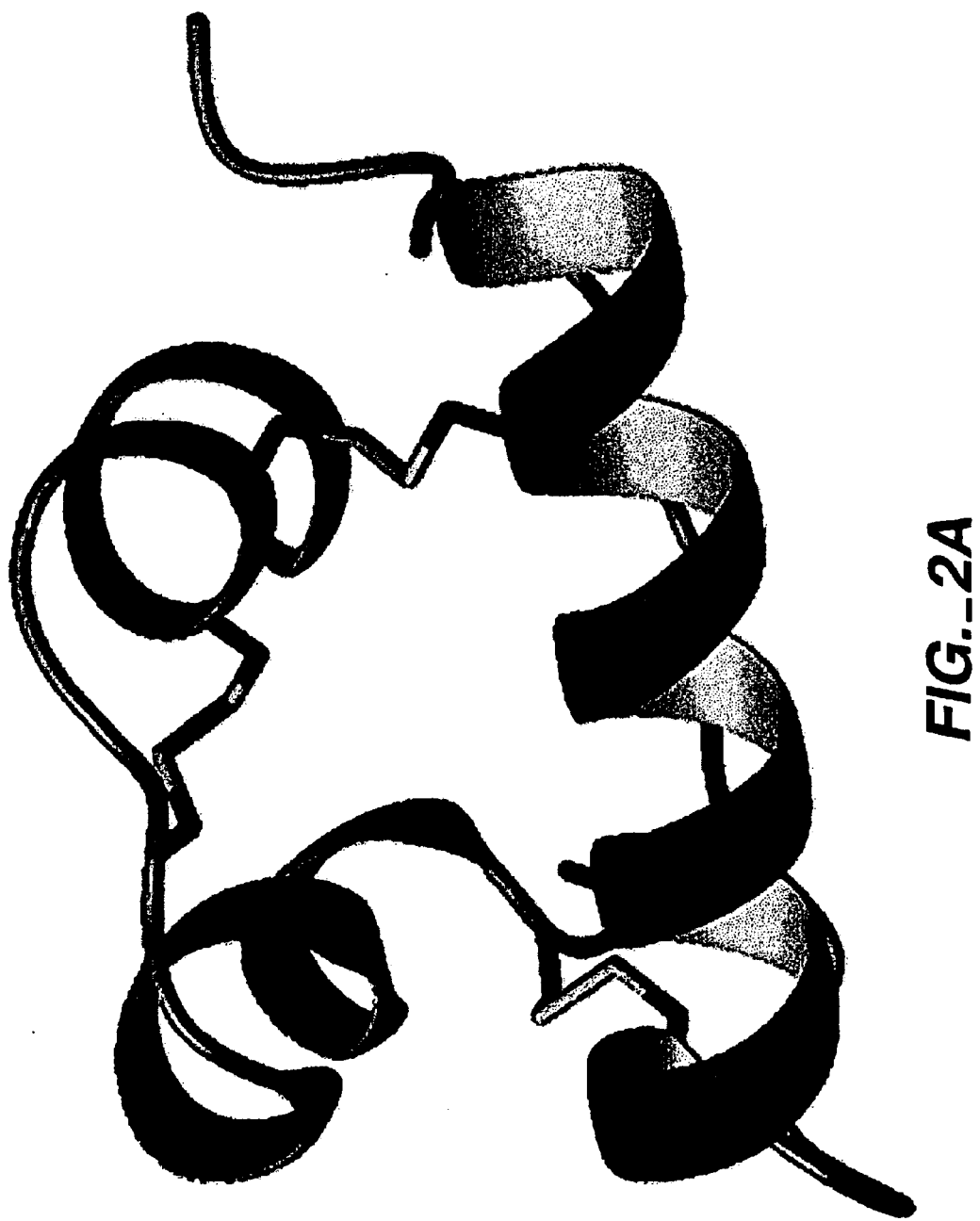
FIG._2A

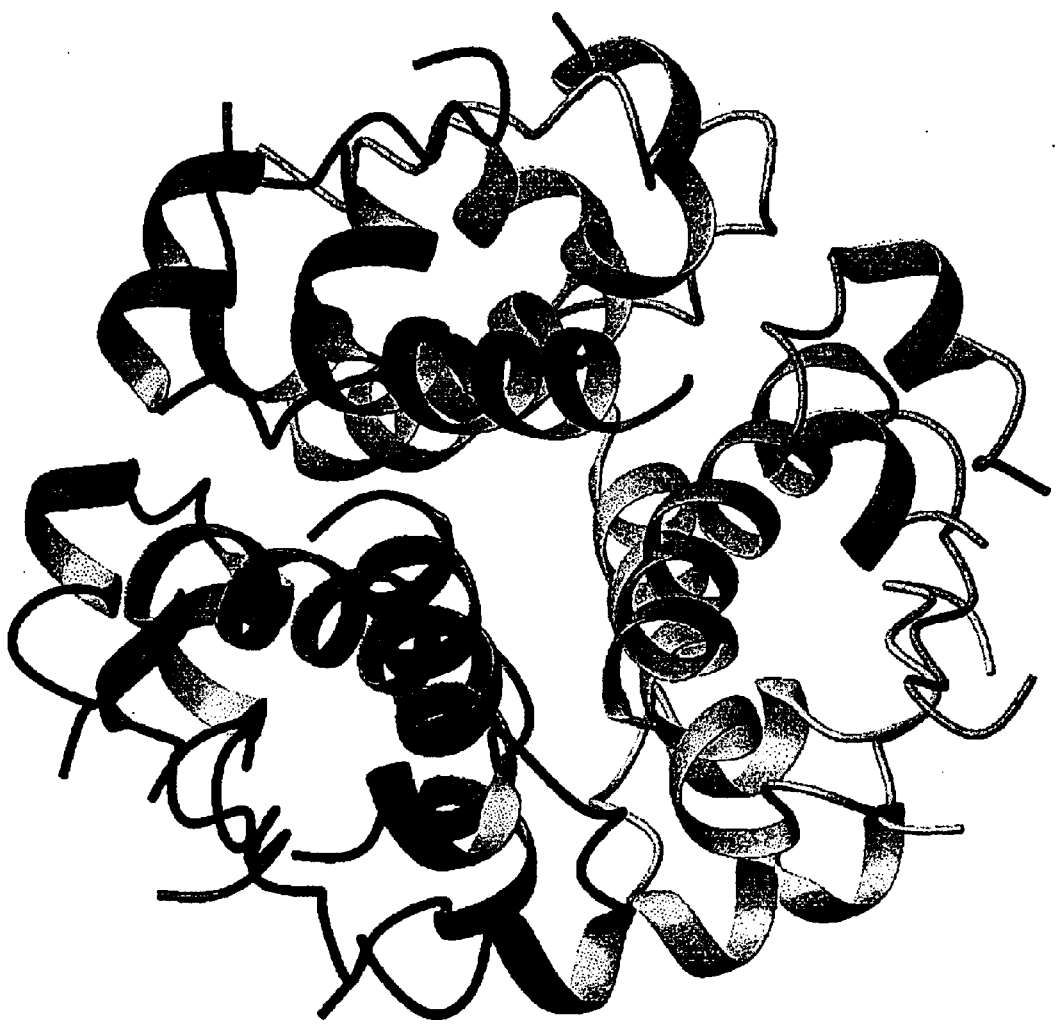
FIG._2B

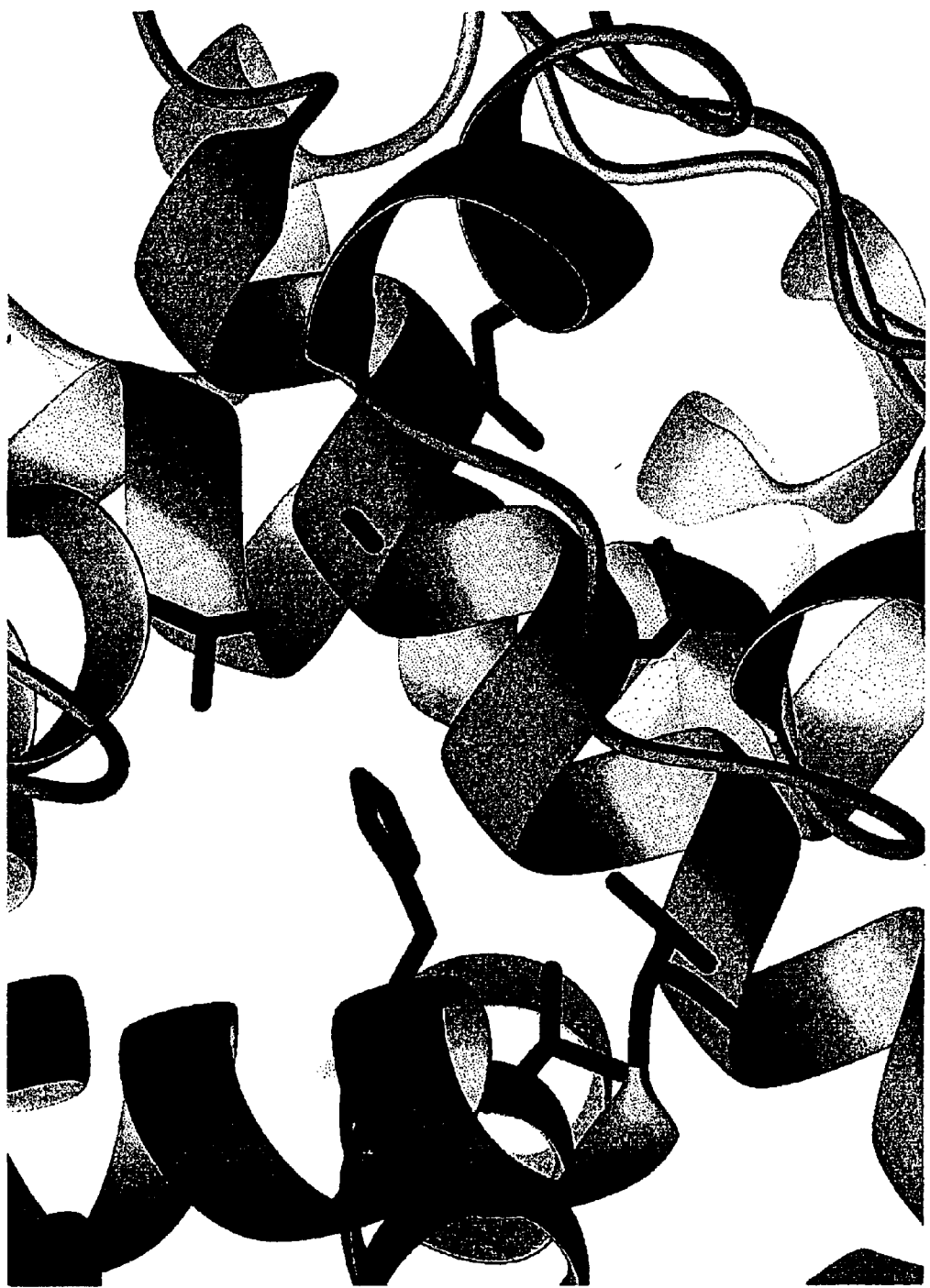
FIG._2C

A-chain | B-chain

1 NLVEQASTSQ ASLYQIYNFD NDVNFHLYGS HIREWLYLVA GERGFNFDPK T

FIG._3A

A-chain | B-chain

1 GIVEQCSTSI CSLYQLENYC NFENYHLYGS HLVEALYLVC GERGFFYTPK T

FIG._3B

A-chain | B-chain

1 GIVEQCSTSI CSLYQLENYC NFVNQHLDGS HLVEALYLVC GERGFFYTPK T

FIG._3C

A-chain | B-chain

1 GIVEQCSTSI CSLYQLENYC NFTNYHLYGS HLVEALYLVC GERGFFYTPK T

FIG._3D

A-chain | B-chain

1 GIVEQCSTSI CSLYQLENYC NFVNYHLYGS HLVEALYLVC GERGFFYTPK T

FIG._3E

A-chain | B-chain

1 GIVEQCSTSI CSLYQLENYC NFVNQHLEGS HLVEALYLVC GERGFFYTPK T

FIG._3F

A-chain | B-chain

1 GIVEQCETSI CSLYQLENYC N----HLEGS HLVEALYLVC GERGFFYTPK T

FIG._3G

```
              A-chain                        B-chain
    ---------------------|----------------------------------
    1  GIVEQCCTSI CSLYQLENYC NFVNQFLCGS HLVEFLYLVC GERGFFYTPK T
```

FIG. 4A

```
              A-chain                        B-chain
    ---------------------|----------------------------------
    1  GIVEQCCTSI CSLYQLENYC NFVNQFLCGS HLVEALYLVC GERGFFYTPK T
```

FIG. 4B

```
              A-chain                        B-chain
    ---------------------|----------------------------------
    1  GIVEQCCTSI CSLYQLENYC NFVNQHLCGS HLVEFLYLVC GERGFFYTPK T
```

FIG. 4C

```
              A-chain                        B-chain
    ---------------------|----------------------------------
    1  GIVEQCCTSI CSLYQLENYC NFVNQHLCGS HLVEWLYLVC GERGFFYTPK T
```

FIG. 4D

```
              A-chain                        B-chain
    ---------------------|----------------------------------
    1  GIVEQCCTSI CSLYQLENYC NFVNQFLCGS HLVEWLYLVC GERGFFYTPK T
```

FIG. 4E

```
              A-chain                        B-chain
    ---------------------|----------------------------------
    1  GIVEQCCTSI CSLYQLENYC NFVNQHLCGS HLVEYLYLVC GERGFFYTPK T
```

FIG. 4F

```
              A-chain                        B-chain
    ---------------------|----------------------------------
    1  GIVEQCCTSI CSLYQLENYC NFVNQHLCGS HLVEILYLVC GERGFFYTPK T
```

FIG. 4G

```
              A-chain                         B-chain
------------------------|------------------------------------
1 NIVEQCCTSQ CSLYQYENYC NDVNQHLCGS HLVEALYLVC GERGFNYDPK T
```

FIG._5A

```
              A-chain                         B-chain
------------------------|------------------------------------
1 NIVEQCCTSQ CSLYQYYNFC NDKNFHLCGS HIREWLYLVC GERGFNFDPK T
```

FIG._5B

```
              A-chain                         B-chain
------------------------|------------------------------------
1 NIVEQCCTSQ CSLYQYYNFC NDKNFHLCLS HIREWLYLVC GERGFNFDNK T
```

FIG._5C

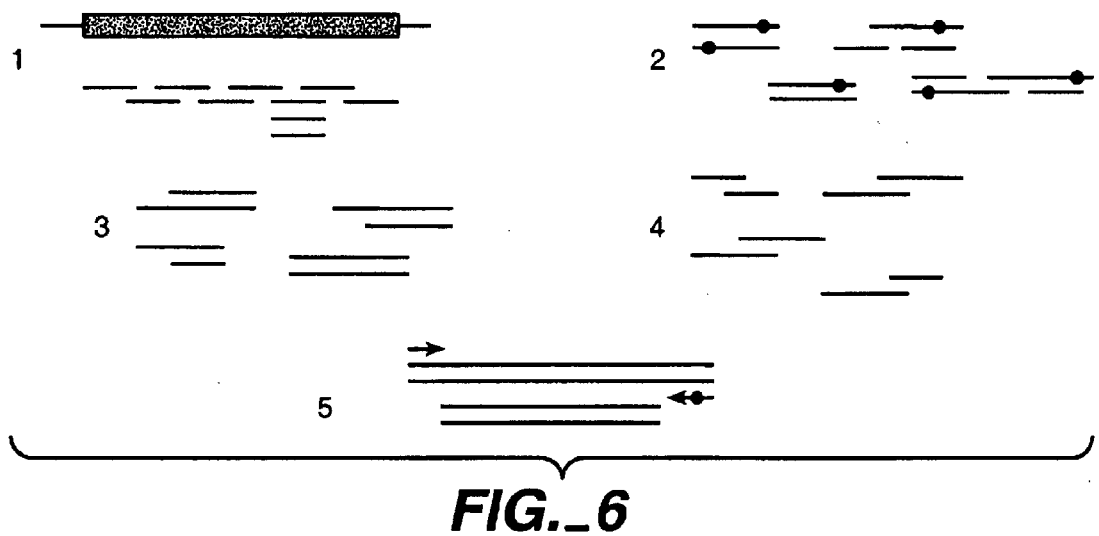
FIG._6
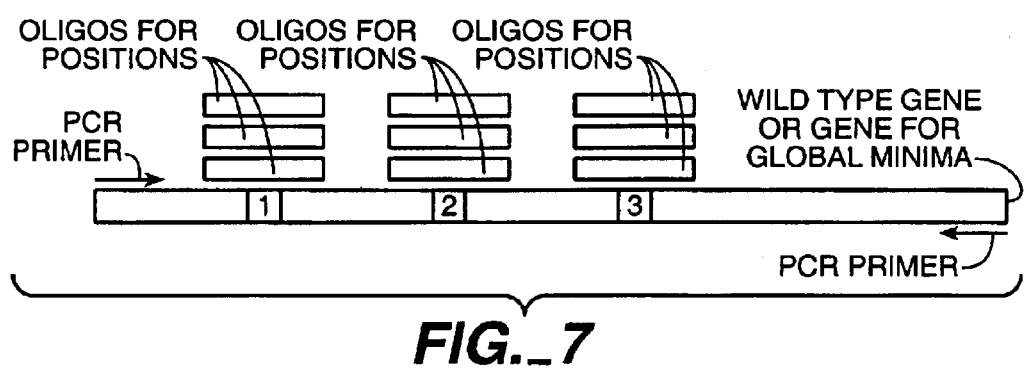
FIG._7

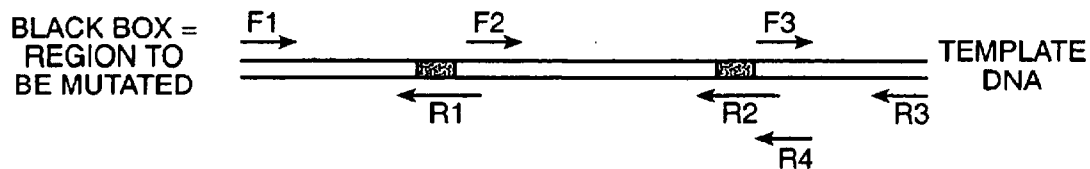
BLACK BOX = REGION TO BE MUTATED
TEMPLATE DNA
STEP 1: SET UP 3 PCR REACTIONS:
PRODUCTS:
TUBE 1:
TUBE 2:
TUBE 3:
STEP 2: SET UP PCR REACTION WITH PRODUCTS OF TUBE 1 + PRODUCTS TUBE 2 + F1 + R4.
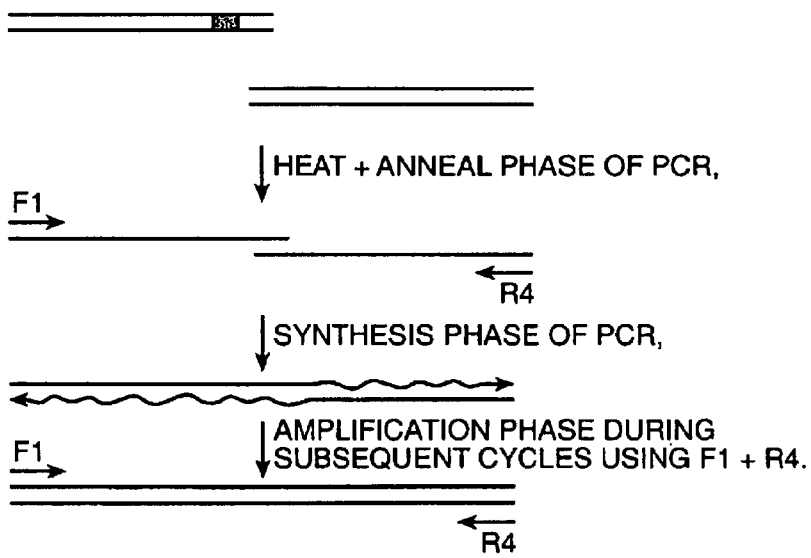
STEP 3: REPEAT STEP 2 USING PRODUCT FROM STEP 2 + PRODUCT FROM STEP 1, TUBE 3 + PRIMERS F1 + R3.
FIG._8

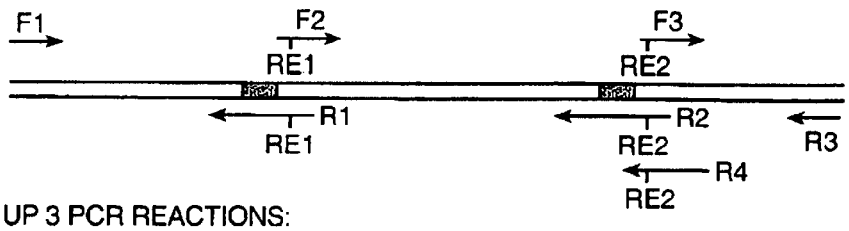

STEP 1: SET UP 3 PCR REACTIONS:

TUBE 1: 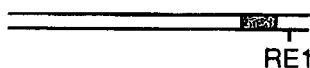

TUBE 2: 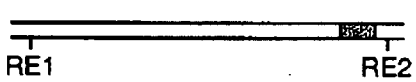

TUBE 3: 

STEP 2: DIGEST PRODUCTS FROM STEP 1 WITH SUITABLE RESTRICTION ENDONUCLEASES.

STEP 3: LIGATE DIGESTED PRODUCT FROM STEP 2, TUBE 2 WITH DIGESTED PRODUCT FROM STEP 2, TUBE 1.

STEP 4: AMPLIFY VIA PCR LIGATED PRODUCTS OF STEP 3 WITH F1 + R4.

STEP 5: DIGEST AMPLIFIED PRODUCT OF STEP 4 WITH RESTRICTION ENDONUCLEASE #2.

STEP 6: LIGATE PRODUCT FROM STEP 5 WITH PRODUCT FROM STEP 2, TUBE 3.

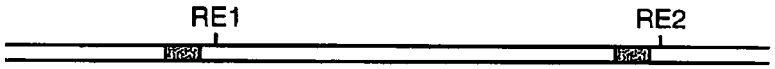

STEP 7: AMPLIFY PRODUCT FROM STEP 6 WITH F1 + R3.

FIG._9

DIAGRAM 3

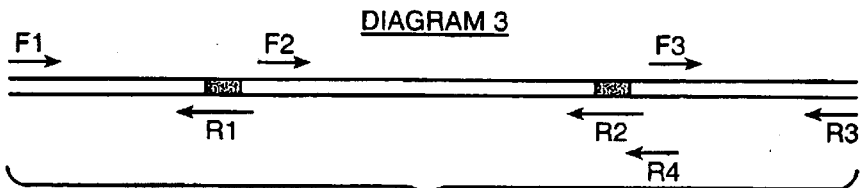

FIG._10

PROTEINS WITH INSULIN-LIKE ACTIVITY USEFUL IN THE TREATMENT OF DIABETES

This application is a continuing application of U.S. Ser. No. 60/134,930, filed May 19, 1999.

FIELD OF THE INVENTION

The invention relates to novel insulin activity (IA) proteins and nucleic acids. The Invention further relates to the use of the IA proteins in the treatment of Insulin-related disorders such as type 1 diabetes and type 2 diabetes.

BACKGROUND OF THE INVENTION

Insulin is a hormone that plays a major role in the regulation of growth and metabolism in vertebrates. A deficiency of insulin is the most important factor in diabetic disease states. Absence of insulin leads to severe metabolic disorders resulting from the failure to normally metabolize carbohydrate, fat and proteins at a normal rate. These disorders include, for example diabetes mellitus (DM), a complex chronic metabolic disorder. Diabetes mellitus is characterized in two broad groups based on clinical manifestations, namely the non-insulin-dependent diabetes (NIDDM) or maturity onset form, also known as Type 2 and the insulin-dependent diabetes (IDDM) or juvenile onset form, also known as Type 1. In the general population, diabetes mellitus occurs with a prevalence of approximately 1%, with one fourth of these being the Type1. In its most fully expressed clinical form, diabetes mellitus manifests itself as a series of hormone-induced metabolic abnormalities which eventually lead to serious, long-term and debilitating complications such as glucosuria, ketonuria, growth arrest, and negative nitrogen balance. These conditions can ultimately lead to death. Familial hyperproinsulinemla is a genetic disorder characterized by a marked increase in serum proinsulin-like molecules. The cause of this disease is an amino acid substitution which results in incomplete cleavage of proinsulin by the proteases which form insulin.

Type 1 diabetes arises for example, when patients lack beta-cells producing insulin in their pancreatic glands or when the produced insulin is inactive due to mutation(s). Type 2 diabetes occurs in patients with an impaired beta cell function. Type 1 diabetic patients are currently treated with insulin, while the majority of type 2 diabetic patients are treated either with sulfonylureas that stimulate beta cell function or with agents that enhance the tissue sensitivity of the patients towards insulin (e.g., metformin) or with insulin.

Today, insulin administration to diabetic patients is the primary therapeutic means for controlling the disease. In the treatment of diabetes mellitus, many varieties of insulin preparations have been suggested and used. Some of the preparations are fast acting and other preparations have more or less prolonged actions. Such a prolonged action may be obtained by administering the insulin as a suspension of insulin crystal which can be obtained by crystallization of insulin in the presence of zinc (such as LENTE; Novo Terapeutisk Laboratorium) or by crystallization of insulin in the presence of zinc and protamine (such as NPH-insulin).

The human insulin monomer, a 6000 dalton protein, is composed of two chains, the 21 amino acid A-chain and the 30 amino acid B-chain. Insulin is synthesized in pancreatic beta cells located within the islets of Langerhans as a precursor form that is post-translationally processed to the mature two polypeptide chain active hormone. In the biologically active human insulin, the A and B chains are linked with one another via two cysteine bridges, and a further cysteine bridge occurs within the A-chain. The following cysteine residues are linked with one another in human insulin: A6-A-11, A7-B7, and A20B-19 (the letters A and B stand for the amino acid chain, and the numbers for the position of the cysteine residues counted from the amino to carboxyl end of each chain; see FIG. 1).

Based on the functional analysis of insulins from various species and several insulin analogs or mutants, some pertinent properties of insulin have emerged with respect to the amino acid sequence (see also FIG. 1): biologically active insulin has three disulfide bonds; B1-Phe is present in all known mammalian insulins; A1-Gly; a terminal tripeptide sequence (A19–21) Tyr-Cys-Asn (removal of A21-Asn by carboxypeptidase digestion results in a loss of activity of>90%); an invariant sequence at B24–26, Phe-Phe-Tyr; B12-Val is highly conserved; A2–A3, Ile-Val is highly conserved; B5-His and B22-Arg are invariant in insulins of high potency; invariant surface residues (highly conserved) A1-Gly, A4-Glu, A5-Gln, A7-Cys, A19-Tyr, A21-Asn, and B7-Cys.

To this end, variants of insulin sequences, applications, production procedures and assays are known;

see for example U.S. Pat. No. 4,421,685 (reports process for producing insulin); U.S. Pat. No. 4,992,417 (reports superactive insulin analogues); U.S. Pat. No. 5,008,241 (reports insulin analogs characterized by amino acid residue substitutions of N21 in the A-chain, with a resulting improvement in stability of insulin solutions at acidic pH levels); U.S. Pat. No. 5,506,202 (reports preparation and use of insulin derivatives comprising various amino acid substitutions); U.S. Pat. No. 5,514,646 (reports analogs of human insulin modified at position 29 of the B-chain that have modified physico-chemical and pharmacokinetic properties and are useful in the treatment of hyperglycemia); U.S. Pat. No. 5,559,094(reports analogs of human insulin containing an aspartic acid at position 1 of the B-chain and U.S. Pat. No. 5,618,913 (reports rapid acting human insulin analogues having amino acid residue substitution and less tendency to self-associate into dimers, tetramers, hexamers or polymers); U.S. Pat. No. 5,621,073 (reports a process for purification of insulin or an insulin acetylated at position A9); U.S. Pat. No. 5,663,291 (reports a process for obtaining insulin having correctly linked cysteine bridges from a corresponding proinsulin amino acid chain); U.S. Pat. No. 5,700,662 (reports process for preparing insulin analogs comprising a modification of position 29 of the B-chain); U.S. Pat. No. 6,034,054 (reports a monomeric insulin analog formulation stabilized against aggregation); all of which are expressly incorporated by reference and further by Marki et al. [Hoppe Seylets Z. Phsiol. Chem. 360(11):1619–32 (1979)]; Hu et al. [Biochemistry 32(10):2631–5 (1993)]; Schwartz et al. [Proc. Natl. Acad. Sci. U.S.A. 84(18):6408–11(1987)]; Kitagawa et al. [Biochemistry 23(7):1405–13 (1984)]; Kobayashi et al. [Biochem. Biophs. Res. Commun. 107(1):329–36 (1982)]; Shoelson et al. [Biochemistry 31(6):1757–67 (1992]; and references cited therein, all of which are expressly incorporated as reference.

Human insulin in solution is known to exist in many molecular forms, such as the monomer, the dimer, the tetramer and the hexamer [Blundell et al., in Advances in Protein Chemistry, Academic Press, New York and London, Vol.26, pp279–330 (1972)], with the oligomer forms being favored at high insulin concentrations and the monomer being the active form of insulin. Insulin in the bloodstream is highly dilute, being $10^{-11}$ to $10^{-8}$ M and is primarily in monomer form. The much more concentrated insulin stored in the beta cell of the pancreas and in the usual administerable solution is largely in the non-active hexamer form, as the well-known 2 zinc hexamer (see below). The delayed absorption phenomena [Binder, Diabetes Care 7(2):188–99 (1984)] is in some large part attributable to the required for the insulin to disassociate from hexamer, tetramer and dimer form into the active monomer form.

in the presence of zinc (Zn), natural human insulin associates to a 2 Zn-hexamer that functions as an allosteric protein. Phenolic ligands or certain salts are capable of inducing a conformational transition, resulting in the N-terminal 8 amino acids of the B-chain converting from an extended conformation to an Q-helix. This conformational state induced by phenolic ligands has been referred to as the R state and the apoinsulin form as the T state. The R state is more compact, less flexible, and the Zn exchange is retarded compared to the T state [Derewenda et al., Nature 338(6216):594–596 (1989)]. A stable intermediate state, $T_3R_3$ has been Identified that has one trimer in the T state and the other in the R state [Chothia et al., Nature 302(5908):500–505 (1983)]. The $T_3R_3$ state was formally known as the 4-Zn insulin structure which is induced by salts (e.g. chloride) or by limited amounts of phenolics [Kruger, et al., Biol. Chem. Hoppe-Seyler 371(8):669–673 (1990)].

The different allosteric states of insulin hexamer have been best characterized in the crystal state by X-ray crystallography [Bentley et al., Nature 261(5556):166–168 (1976); Smith & Dodson, Biopolymers 32(4):441–445 (1992)], in solution by proton NMR, circular dichroism [Renscheidt et al., Eur. J. Biochem. 142(1):7–14 (1984)], and visible absorption spectroscopy of $Co_{2+}$ substituted insulins [Brader et al., Biochemistry 30(27):6636–6645 (1991)]. The biological significance of insulin allosterism has not been fully elucidated. The biologically active form of insulin is thought to be a monomer due to the dilute concentrations of insulin in the blood circulation [Frank et al., Diabetes 21(2):Suppl. 2:486–491 (1972)]. A receptor-mediated conformational change in the insulin conformation is thought to be required for binding [see Hua et al. Nature 354(6350):238–41 (1991); Bao et al. Proc. Natl. Acad. Sci. U.S.A. 94(7):2975–80 (1997)]. For the medicinal use of insulin, the T->R conformations have important consequences. Most formulations of insulin are solutions or suspensions that contain phenolics that function as preservatives against bacterial contamination. The phenolic concentrations in insulin formulations are 2–10 times that necessary to induce the R conformation (Kruger et al., supra). The presence of phenolics in insulin formulations has also important consequences on the shelf-life stability [Brange et al., Pharm. Res. 9(6):715–726 (1992); Brange et al., Pharm. Res. 9(6):727–734 (1992); Brange & Langkjaer, Acta Pharm Nord.,4(3):149–158 (1992)] and possibly time action profile. Minimizing degradation of insulin formulations is extremely important in reducing undesirable side effects of insulin therapy.

The crystal structures of various recombinant insulin molecules are solved. The structures can be obtained from the Research Collaboratory for Structural Bioinformatics as entries into the Protein Data Bank (PDB). Insulin entries include wild type insulin (e.g., see PDB entries 1ZEH, 1ZNJ, 1ZNI, 1XDA, 4INS, and 9INS), insulin analogs or mutants (e.g., PDB entries 1IOH, 1IOG, 1B9E, 1BYZ, 1ZEI, 1A7F, 1HUI, 1LPH, and 1IZA), R6 (wild type or analog) insulin hexamers (e.g., PDB entries 5AIY, 4AIY, 3AIY, 2AIY, 1AIY, 1AI0, 1QIZ, 1QJ0, and 1QIY); insulin complexed with phenol (e.g., PDB entry 1ZEG), insulin complexed with 4hydroxybenzanide (e.g., PDB entry 1BEN), insulin (wild type or analog) complexed with Zn ions (e.g., PDB entries 1TYM, 1TYL, 7INS, 1TRZ, and 1IZB), and other variants (e.g., PDB entries 1MPJ, 2TCI, 3MTH, 6INS, and 2INS) and insulins in various pH solutions (e.g., PDB entries 1DPH, 1CPH, 1BPH, and 1 APH), all of which are expressly incorporated by reference.

When carrying out protein engineering to modify protein properties, usually one had to select from the following options: (i) site-specific mutagenesis and (ii) random mutagenesis of the nucleic acid encoding the protein, or (iii) post-translational chemical modifications. No matter which method of protein engineering is used, a key aspect is determining which amino acids to modify, because few choices will improve the properties of the protein. The available crystal structure of insulin allows a completely different approach by using computational protein design and the generation of more stable proteins or protein variants with an altered activity. Several groups have applied and experimentally tested systematic, quantitative methods to protein design with the goal of developing general design algorithms (Hellinga et al., J. Mol. Biol. 222: 763–785 (1991); Hurley et al., J. Mol. Biol. 224:1143–1154 (1992); Desjarlaisl et al., Protein Science 4:2006–2018 (1995); Harbury et al., Proc. Natl. Acad. Sci. U.S.A. 92:8408–8412 (1995); Klemba et al., Nat. Struc. Biol. 2:368–373 (1995); Nautiyal et al., Biochemistry 34:11645–11651 (1995); Betzo et al., Biochemistry 35:6955–6962 (1996); Dahiyat et al., Protein Science 5:895–903 (1996); Dahiyat et al., Science 278:82–87 (1997); Dahiyat et al., J. Mol. Biol. 273:789–96; Dahiyat et al., Protein Sci. 6:1333–1337 (1997); Jones, Protein Science 3:567–574 (1994); Konol, et al., Proteins: Structure, Function and Genetics 19:244–255 (1994)). These algorithms consider the spatial positioning and steric complementarity of side chains by explicitly modeling the atoms of sequences under consideration. In particular, WO98/47089, and U.S. Ser. No. 09/127,926 describe a system for protein design; both are expressly incorporated by reference.

A need still exists for proteins exhibiting both significant stability and insulin activity. Accordingly, it is an object of the invention to provide insulin activity (IA) proteins, nucleic acids and antibodies for the treatment of insulin-related disorders.

SUMMARY OF THE INVENTION

In accordance with the objects outlined above, the present invention provides non-naturally occurring insulin activity (IA) proteins (e.g. the proteins are not found in nature) comprising amino acid sequences that are less than about 98% identical to human insulin. The IA proteins have at least one altered biological property of an insulin protein; for example, the IA proteins will be more stable than insulin and bind to a cell comprising an insulin receptor. Thus, the invention provides IA proteins with amino acid sequences that have at least about 1–20 amino acid substitutions as compared to the human insulin sequence shown in FIG. 1B.

In a further aspect, the present invention provides non-naturally occurring IA protein conformers that have three dimensional backbone structures that substantially correspond to the three dimensional backbone structure of insulin. The amino acid sequence of the IA protein conformer and the amino acid sequence of insulin are less than about 98% Identical.

In an additional aspect, the changes are selected from the amino acid residues at positions selected from positions A2, A3, A5, A6, A7, A11, A15, A16, A19, A20, B2, B7, B11, B15, B18, B19, B22, and B24. In a preferred aspect of this embodiment, the changes are substitutions selected from the group of A7-S, A7-E, B2-E, B2-T, B4-Y, B7-Y, B4F, B7-E, and B7-D.

In a preferred aspect, the changes are selected from the amino acid residues at positions selected from positions B5 and B14. in a preferred aspect of this embodiments the changes are substitutions selected from the group of B5-F, B5-W, B14-F, B14-W, B14-Y, and B14-I.

In an additional aspect, the changes are selected from the amino acid residues at positions selected from positions A1, A10, A16, A17, A19, B1, B2,B4, B8, B11, B12, B14, B25, B26, B27, and B28. In a preferred aspect of this embodiment, the changes are substitutions selected from the group of A1-N, A10-Q, A16-Y, A17-Y, A19-F, B1-D, B2-K, B4-F, B8-L, B11-I, B12-R, B14W, B25-N, B26-F, B27-D, and B28-N.

In a further aspect, the invention provides recombinant nucleic acids encoding the non-naturally occurring IA proteins, expression vectors comprising the recombinant nucleic acids, and host cells comprising the recombinant nucleic acids and expression vectors.

In an additional aspect, the invention provides methods of producing the IA proteins of the invention comprising culturing host cells comprising the recombinant nucleic acids under conditions suitable for expression of the nucleic acids. The proteins may optionally be recovered. In a further aspect, the invention provides pharmaceutical compositions comprising an IA protein of the invention and a pharmaceutical carrier.

In an additional aspect, the invention provides methods for treating an insulin responsive condition comprising administering an IA protein of the invention to a patient. The insulin responsive condition includes a disorder of carbohydrate metabolism, type 1 diabetes, and type 2 diabetes.

BRIEF DESCRIPTION OF THE DRAWINGS

FIG. 1A depicts the amino acid sequence of the insulin precursor (GenBank accession #P01308, #AAA59173). Amino acid residues 1–24 represent the signal peptide; amino acid residues 25–54 represent the mature B-chain; amino acid residues 90–110 represent the mature A-chain.

FIG. 1B depicts the amino acid sequence of human insulin [GenBank accession #229122; Nicol and Smith, Nature 187:483–485 (1960)], which is used herein for PDA design and for reference of amino acid positions. The A-chain comprises amino acid residues 1–21 (sometimes referred to as A1 through A 21) and the B-chain comprises residues 22–51 (sometimes referred to as B1 through B30), respectively.

FIG. 1C depicts the amino acid sequences of the A-chains of human insulin (1TRZ:A and 1TRZ:C) and B-chains of human insulin (1TRZ:B and 1TRZ:D) as used in determination of the structure of insulin (T3R3) complex with two zinc ions [PDB entry 1TRZ; Ciszak and Smith, Biochemistry 33(6):1512–7 (1994)] and secondary structure elements. Secondary structure element legend: H, alpha helix (4-helix); B, residue in isolated beta bridge; E, extended strand, participates in beta ladder, G, 310 helix (3-helix); I, pi helix (5-helix); T, hydrogen bonded turn; S, bend.

FIG. 2A depicts the structure of a wild type insulin monomer with side chains for disulfide bonds (A6–A11, A7–B7, and A20–B19) and the B-Ala14 side chain shown.

FIG. 2B depicts the structure of a wild type insulin hexamer.

FIG. 2C depicts a closeup of the B14, B5 design region in the insulin hexamer.

FIG. 3 shows preferred IA protein sequences from PDA designs involving disulfide replacement. Amino acid changes when compared to wild type human insulin are indicated in bold and are underlined.

FIG. 3A shows a preferred IA protein sequence from PDA design ‘cys1’.

FIG. 3B shows a preferred IA protein sequence from PDA design ‘cys77a’.

FIG. 3C shows a preferred IA protein sequence from PDA design ‘cys77b’.

FIG. 3D shows a preferred IA protein sequence from PDA design ‘cys77d’.

FIG. 3E shows a preferred IA protein sequence from PDA design ‘cys77d+’.

FIG. 3F shows a preferred IA protein sequence from PDA design ‘helix 24’.

FIG. 3G shows a preferred IA protein sequence from PDA design ‘cys-4’. For this design, a in the sequence indicates a deletion.

FIGS. 4A–4G show preferred IA protein sequences from FDA designs involving mutations which promote insulin hexamer formation. Amino acid changes when compared to wild type human insulin are indicated in bold and are underlined.

FIG. 5 shows preferred IA protein sequences from PDA designs involving global redesigns for improved stability. Amino acid changes when compared to wild type human insulin are indicated in bold and are underlined.

FIG. 5A shows a preferred IA protein sequence from PDA design ‘trz_06’.

FIG. 5B shows a preferred IA protein sequence from PDA design ‘trz_7b’.

FIG. 5C shows a preferred IA protein sequence from PDA design ‘trz_08’.

FIG. 6 depicts the synthesis of a full-length gene and all possible mutations by PCR. Overlapping oligonucleotides corresponding to the full-length gene (black bar, Step 1) and comprising one or more desired mutations are synthesized, heated and annealed. Addition of DNA polymerase to the annealed oligonucleotides results in the 5' to 3' synthesis of DNA (Step 2) to produce longer DNA fragments (Step 3). Repeated cycles of heating, annealing, and DNA synthesis (Step 4) result in the production of longer DNA, including some full-length molecules. These can be selected by a second round of PCR using primers (indicated by arrows) corresponding to the end of the full-length gene (Step 5).

FIG. 7 depicts a preferred scheme for synthesizing an IA protein library of the invention. The wild type gene, or any starting gene, such as the gene for the global minima gene, can be used. Oligonucleotides comprising sequences that encode different amino acids at the different variant positions (indicated in the Figure by box 1, box 2, and box 3 ) can be used during PCR. Those primers can be used in combination with standard primers. This generally requires fewer oligonucleotides and can result in fewer errors.

FIGS. 8A and 8B depict an overlapping extension method. At the top of FIG. 8A is the template DNA showing the locations of the regions to be mutated (black boxes) and the binding sites of the relevant primers (arrows). The primers R1 and R2 represent a pool of primers, each containing a different mutation; as described herein, this may be done using different ratios of primers if desired. The variant position is flanked by regions of homology sufficient to get hybridization. Thus, as shown in this example, oligos R1 and F2 comprise a region of homology and so do oligos R2 and F3. In this example, three separate PCR reactions are done for step 1. The first reaction contains the template plus oligos F1 and R1. The second reaction contains template plus oligos F2 and R2, and the third contains the template and oligos F3 and R3. The reaction products are shown. In Step 2, the products from Step 1 tube 1 and Step 1 tube 2 are taken. After purification away from the primers, these are added to a fresh PCR reaction together with F1 and R4. During the denaturation phase of the PCR, the overlapping regions anneal and the second strand is synthesized. The product is then amplified by the outside primers, F1 and R4. In Step 3, the purified product from Step 2 is used in a third PCR reaction, together with the product of Step 1, tube 3 and the primers F1 and R3. The final product corresponds to the full length gene and contains the required mutations. Alternatively, Step 2 and Step 3 can be performed in one PCR reaction.

FIGS. 9A and 9B depict a ligation of PCR reaction products to synthesize the libraries of the invention. In this technique, the primers also contain an endonuclease restriction site (RE), either generating blunt ends, 5' overhanging ends or 3' overhanging ends. We set up three separate PCR reactions for Step 1. The first reaction contains the template plus oligos F1 and R1. The second reaction contains template plus oligos F2 and R2, and the third contains the template and oligos F3 and R3. The reaction products are shown. In Step 2, the products of Step 1 are purified and then digested with the appropriate restriction endonuclease. The digestion products from Step 2, tube 1 and Step 2, tube 2 are ligated together with DNA ligase (Step 3). The products are then amplified in Step 4 using oligos F1 and R4. The whole process is then repeated by digesting the amplified products, ligating them to the digested products of Step 2, tube 3, and then amplifying the final product using oligos F1 and R3. It would also be possible to ligate all three PCR products from Step 1 together in one reaction, providing the two restriction sites RE1 and RE2) were different FIG. 10 depicts blunt end ligation of PCR products. In this technique, oligos such as F2 and R1 or R2 and F3 do not overlap, but they abut. Again three separate PCR reactions are performed. The products from tube 1 and tube 2 (see FIG. 9A, Step 1) are ligated, and then amplified with outside primers F1 and R4. This product is then ligated with the product from Step 1, tube 3. The final products are then amplified with primers F1 and R3:

DETAILED DESCRIPTION OF THE INVENTION

The present invention is directed to novel proteins and nucleic acids possessing insulin activity (sometimes referred to herein as "IA proteins" and "IA nucleic acids"). The proteins are generated using a system previously described in WO98/47089 and U.S. Ser. Nos. 09/058,459, 09/127,926, 60/104,612, 60/158,700, 09/419,351, 60/181,630, 60/186,904, and U.S. patent application, entitled Protein Design Automation For Protein Libraries (Filed: Apr. 14, 2000; inventor: Bassil Dahiyat), all of which are expressly incorporated by reference in their entirety, that is a computational modeling system that allows the generation of extremely stable proteins without necessarily disturbing the biological functions of the protein itself. In this way, novel IA proteins and nucleic acids are generated, that can have a plurality of mutations in comparison to the wild-type enzyme yet retain significant activity.

Generally, there are a variety of computational methods that can be used to generate the IA proteins of the invention. In a preferred embodiment, sequence based methods are used. Alternatively, structure based methods, such as PDA, described in detail below, are used.

Similarly, molecular dynamics calculations can be used to computationally screen sequences by individually calculating mutant sequence scores and compiling a rank ordered list In a preferred embodiment, residue pair potentials can be used to score sequences (Miyazawa et al., Macromolecules 18(3):534–552 (1985), expressly incorporated by reference) during computational screening.

In a preferred embodiment, sequence profile scores (Bowie et al., Science 253(50,16):164–70 (1991), incorporated by reference) and/or potentials of mean force (Hendlich et al., J. Mol. Biol. 216(1):167–180 (1990), also incorporated by reference) can also be calculated to score sequences. These methods assess the match between a sequence and a 3D protein structure and hence can act to screen for fidelity to the protein structure. By using different scoring functions to rank sequences, different regions of sequence space can be sampled in the computational screen.

Furthermore, scoring functions can be used to screen for sequences that would create metal or co-factor binding sites in the protein (Hellinga, Fold Des. 3(1):R1–8 (1998), hereby expressly incorporated by reference). Similarly, scoring functions can be used to screen for sequences that would create disulfide bonds in the protein. These potentials attempt to specifically modify a protein structure to introduce a new structural motif.

In a preferred embodiment, sequence and/or structural alignment programs can be used to generate the IA proteins of the invention. As is known in the art, there are a number of sequence-based alignment programs; including for example, Smith-Waterman searches, Needleman-Wunsch, Double Affine Smith-Waterman, frame search, Gribskov/GCG profile search, Gribskov/GCG profile scan, profile frame search, Bucher generalized profiles, Hidden Markov models, Hframe, Double Frame, Blast, Psi-Blast, Clustal, and GeneWise.

As is known in the art, there are a number of sequence alignment methodologies that can be used. For example, sequence homology based alignment methods can be used to create sequence alignments of proteins related to the target structure (Altschul et al., J. Mol. Biol. 215(3):403–410 (1990), Altschul et al., Nucleic Acids Res. 25:3389–3402 (1997), both incorporated by reference). These sequence alignments are then examined to determine the observed sequence variations. These sequence variations are tabulated to define a set of IA proteins.

Sequence based alignments can be used in a variety of ways. For example, a number of related proteins can be aligned, as is known in the art, and the "variable" and "conserved" residues defined; that is, the residues that vary or remain identical between the family members can be defined. These results can be used to generate a probability table, as outlined below. Similarly, these sequence variations can be tabulated and a secondary library defined from them as defined below. Alternatively, the allowed sequence variations can be used to define the amino acids considered at each position during the computational screening. Another variation is to bias the score for amino acids that occur in the sequence alignment, thereby increasing the likelihood that they are found during computational screening but still allowing consideration of other amino acids. This bias would result in a focused library of IA proteins but would not eliminate from consideration amino acids not found in the alignment. In addition, a number of other types of bias may be introduced. For example, diversity may be forced; that is, a "conserved" residue is chosen and altered to force diversity on the protein and thus sample a greater portion of the sequence space. Alternatively, the positions of high variability between family members (i.e. low conservation) can be randomized, either using all or a subset of amino acids. Similarly, outlier residues, either positional outliers or side chain outliers, may be eliminated.

Similarly, structural alignment of structurally related proteins can be done to generate sequence alignments (Orengo et al., Structure 5(8):1093–108 (1997); Holm et al., Nucleic Acids Res. 26(1):316–9 (1998), both of which are incorporated by reference). These sequence alignments can then be examined to determine the observed sequence variations. Libraries can be generated by predicting secondary structure from sequence, and then selecting sequences that are compatible with the predicted secondary structure. There are a number of secondary structure prediction methods such as helix-coil transition theory (Munoz and Serrano, Biopolymers 41:495, 1997), neural networks, local structure alignment and others (e.g., see in Selbig et al., Bioinformatics 15:1039–46, 1999).

Similarly, as outlined above, other computational methods are known, including, but not limited to, sequence profiling [Bowie and Eisenberg, Science 253(5016):164–70, (1991)], rotamer library selections [Dahiyat and Mayo, Protein Sci. 5(5):895–903 (1996); Dahiyat and Mayo, Science 278(5335):82–7 (1997); Desjarais and Handel, Protein Science 4:2006–2018 (1995); Harbury et Proc. Natl. Acad. Sci. U.S.A. 92(18):8408–8412 (1995); Kono et al., Proteins: Structure, Function and Genetics 19:244–255 (1994); Hellinga and Richards, Proc. Natl. Acad. Sci. U.S.A. 91:5803–5807 (1994)]; and residue pair potentials [Jones, Protein Science 3: 567–574, (1994)]; PROSA [Heindlich et al., J. Mol. Biol. 216:167–180 (1990)]; THREADER [Jones et al., Nature 358:86–89 (1992)], and other inverse folding methods such as those described by Simons et al. [Proteins, 34:535–543, (1999)], Levitt and Gerstein [Proc. Natl. Aced. Sci. U.S.A., 95:5913–5920, (1998)], Godzik and Skolnick [Proc. Natl. Aced. Sci. U.S.A., 89:12098–102, (1992)], Godzik et al. [J. Mol. Biol. 227:227–38, (1992)] and two profile methods [Gribskov et al. Proc. Natl. Acad. Sci. U.S.A. 84:4355–4358 (1987) and Fischer and Eisenberg, Protein Sci. 5:947–955 (1996), Rice and Eisenberg J. Mol. Biol. 267:1026–1038(1997)], all of which are expressly incorporated by reference. In addition, other computational methods such as those described by Koehl and Levitt (J. Mol. Biol. 293:1161–1181 (1999); J. Mol. Biol. 293:1183–1193 (1999); expressly incorporated by reference) can be used to create a protein sequence library which can optionally then be used to generate a smaller secondary library for use in experimental screening for improved properties and function. In addition, there are computational methods based on forcefield calculations such as SCMF that can be used as well for SCMF, see Delarue et al. Pac. Symp. Biocomput. 109–21 (1997); Koehl et al., J. Mol. Biol. 239:249–75 (1994); Koehl et al., Nat. Struct. Biol. 2:163–70 (1995); Koehl et al., Curr. Opin. Struct. Biol. 6:222–6 (1996); Koehl et al., J. Mol. Biol. 293:1183–93 (1999); Koehl et al., J. Mol. Biol. 293:1161–81 (1999); Lee J., Mol. Biol. 236:918–39 (1994); and Vasquez Biopolymers 36:53–70 (1995); all of which are expressly incorporated by reference. Other forcefield calculations that can be used to optimize the conformation of a sequence within a computational method, or to generate de novo optimized sequences as outlined herein include, but are not limited to, OPLS-AA [Jorgensen et al., J. Am. Chem. Soc. 118:11225–11236 (1996); Jorgensen, W. L.; BOSS, Version 4.1; Yale University: New Haven, Conn. (1999)]; OPLS [Jorgensen et al., J. Am. Chem. Soc.110:1657ff (1988); Jorgensen et al., J Am. Chem. Soc.112:4768ff (1990)]; UNRES (United Residue Forcefield; Liwo et al., Protein Science 2:1697–1714 (1993); Liwo et al., Protein Science 2:1715–1731 (1993); Liwo et al., J. Comp. Chem. 18:849–873 (1997); Liwo et al., J. Comp. Chem. 18:874–884 (1997); Liwo et al., J. Comp. Chem. 19:259–276 (1998); Forcefield for Protein Structure Prediction (Liwo et al., Proc. Natl. Acad. Sci. U.S.A. 96:5482–5485 (1999)]; ECEPP/3[Liwo et al., J Protein Chem. 13(4):375–80 (1994)]; AMBER 1.1 force field (Weiner et al., J. Am. Chem. Soc. 106:765–784); AMBER 3.0 force field [U.C. Singh et al., Proc. Natl. Acad. Sci. U.S.A. 82:755–759 (1985)]; CHARMM and CHARMM22 (Brooks et al., J. Comp. Chem. 4:187–217); cvff3.0 [Dauber-Osguthorpe et al., Proteins: Structure, Function and Genetics, 4:31–47 (1988)]; cff91 (Maple et al., J. Comp. Chem. 15:162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference. In fact, as is outlined below, these forcefield methods may be used to generate the secondary library directly; that is, no primary library is generated; rather, these methods can be used to generate a probability table from which the secondary library is directly generated.

In a preferred embodiment, the computational method used to generate the primary library is Protein Design Automation (PDA), as is described in U.S. Ser. Nos. 60/061, 097, 60/043,464, 60/054,678, 09/127,926, 60/104,612, 60/158,700, 09/419,351, 60/181630, 60/186,904, U.S. patent application, entitled Protein Design Automation For Protein Libraries (Filed: Apr. 14, 2000; Inventor: Bassil Dahiyat) and PCT US98/07254, all of which are expressly incorporated herein by reference. Briefly, PDA can be described as follows. A known protein structure is used as the stating point. The residues to be optimized are then identified, which may be the entire sequence or subset(s) thereof. The side chains of any positions to be varied are then removed. The resulting structure consisting of the protein backbone and the remaining side chains is called the template. Each variable residue position is then preferably classified as a core residue, a surface residue, or a boundary residue; each classification defines a subset of possible amino acid residues for the position (for example, core residues generally will be selected from the set of hydrophobic residues, surface residues generally will be selected from the hydrophilic residues, and boundary residues may be either). Each amino acid can be represented by a discrete set of all allowed conformers of each side chain, called rotamers. Thus, to arrive at an optimal sequence for a backbone, all possible sequences of rotamers must be screened, where each backbone position can be occupied either by each amino acid in all its possible rotameric states, or a subset of amino acids, and thus a subset of rotamers.

Two sets of interactions are then calculated for each rotamer at every position: the interaction of the rotamer side chain with all or part of the backbone (the "singles" energy, also called the rotamer/template or rotamer/backbone energy), and the interaction of the rotamer side chain with all other possible rotamers at every other position or a subset of the other positions (the "doubles" energy, also called the rotamer/rotamer energy). The energy of each of these interactions is calculated through the use of a variety of scoring functions, which include the energy of van der Waal's forces, the energy of hydrogen bonding, the energy of secondary structure propensity, the energy of surface area solvation and the electrostatics. Thus, the total energy of each rotamer interaction, both with the backbone and other rotamers, is calculated, and stored in a matrix form.

The discrete nature of rotamer sets allows a simple calculation of the number of rotamer sequences to be tested. A backbone of length n with m possible rotamers per position will have $m^n$ possible rotamer sequences, a number which grows exponentially with sequence length and renders the calculations either unwieldy or Impossible in real time. Accordingly, to solve this combinatorial search problem, a "Dead End Elimination" (DEE) calculation is performed. The DEE calculation is based on the fact that if the worst total interaction of a first rotamer is still better than the best total interaction of a second rotamer, then the second rotamer cannot be part of the global optimum solution. Since the energies of all rotamers have already been calculated, the DEE approach only requires sums over the sequence length to test and eliminate rotamers, which speeds up the calculations considerably. DEE can be rerun comparing pairs of rotamers, or combinations of rotamers, which will eventually result in the determination of a single sequence which represents the global optimum energy.

Once the global solution has been found, a Monte Carlo search may be done to generate a rank-ordered list of sequences in the neighborhood of the DEE solution. Starting at the DEE solution, random positions are changed to other rotamers, and the new sequence energy is calculated. If the new sequence meets the criteria for acceptance, it is used as a starting point for another jump. After a predetermined number of jumps, a rank-ordered list of sequences is generated. Monte Carlo searching is a sampling technique to explore sequence space around the global minimum or to find new local minima distant in sequence space. As is more additionally outlined below, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example), etc.). Similarly, for all the sampling techniques, the acceptance criteria of whether a sampling jump is accepted can be altered.

As outlined in U.S. Ser. No. 09/127,926, the protein backbone (comprising (for a naturally occurring protein) the nitrogen, the carbonyl carbon, the α-carbon, and the carbonyl oxygen, along with the direction of the vector from the α-carbon to the β-carbon) may be altered prior to the computational analysis, by varying a set of parameters called supersecondary structure parameters.

Once a protein structure backbone is generated (with alterations, as outlined above) and input into the computer, explicit hydrogens are added if not included within the structure (for example, if the structure was generated by X-ray crystallography, hydrogens must be added). After hydrogen addition, energy minimization of the structure is run, to relax the hydrogens as well as the other atoms, bond angles and bond lengths. In a preferred embodiment, this is done by doing a number of steps of conjugate gradient minimization [Mayo et al., J. Phys. Chem. 94:8897 (1990)] of atomic coordinate positions to minimize the Dreiding force field with no electrostatics. Generally from about 10 to about 250 steps is preferred, with about 50 being most preferred.

The protein backbone structure contains at least one variable residue position. As is known in the art, the residues, or amino acids, of proteins are generally sequentially numbered starting with the N-terminus of the protein. Thus a protein having a methionine at it's N-terminus is said to have a methionine at residue or amino acid position 1, with the next residues as 2, 3, 4, etc. At each position, the wild type (i.e. naturally occurring) protein may have one of at least 20 amino acids, in any number of rotamers. By "variable residue position" herein is meant an amino acid position of the protein to be designed that is not fixed in the design method as a specific residue or rotamer, generally the wild-type residue or rotamer.

In a preferred embodiment, all of the residue positions of the protein are variable. That is, every amino acid side chain may be altered in the methods of the present invention. This is particularly desirable for smaller proteins, although the present methods allow the design of larger proteins as well. While there is no theoretical limit to the length of the protein which may be designed this way, there is a practical computational limit.

In an alternate preferred embodiment, only some of the residue positions of the protein are variable, and the remainder are "fixed", that is, they are identified in the three dimensional structure as being in a set conformation. In some embodiments, a fixed position is left in its original conformation (which may or may not correlate to a specific rotamer of the rotamer fibrary being used). Alternatively, residues may be fixed as a non-wild type residue; for example, when known site-directed mutagenesis techniques have shown that a particular residue is desirable (for example, to eliminate a proteolytic site or alter the substrate specificity of an enzyme), the residue may be fixed as a particular amino acid. Alternatively, the methods of the present invention may be used to evaluate mutations de novo, as is discussed below. In an alternate preferred embodiment, a fixed position may be "floated"; the amino acid at that position is fixed, but different rotamers of that amino acid are tested. In this embodiment, the variable residues may be at least one, or anywhere from 0.1% to 99.9% of the total number of residues. Thus, for example, it may be possible to change only a few (or one) residues, or most of the residues, with all possibilities in between.

In a preferred embodiment, residues which can be fixed include, but are not limited to, structurally or biologically functional residues; alternatively, biologically functional residues may specifically not be fixed. For example, residues which are known to be important for biological activity, such as the residues which the binding site for a binding partner (ligand/receptor, antigen/antibody, etc.), phosphorylation or glycosylation sites which are crucial to biological function, or structurally important residues, such as disulfide bridges, metal binding sites, critical hydrogen bonding residues, residues critical for backbone conformation such as proline or glycine, residues critical for packing interactions, etc. may all be fixed in their amino acid identity and a single rotamer conformation, or "floated", which only fixes the identity but not the rotamer conformation.

Similarly, residues which may be chosen as variable residues may be those that confer undesirable biological attributes, such as susceptibility to proteolytic degradation, dimerization or aggregation sites, glycosylation sites which may lead to immune responses, unwanted binding activity, unwanted allostery, undesirable enzyme activity but with a preservation of binding, etc.

In a preferred embodiment, each variable position is classified as either a core, surface or boundary residue position, although in some cases, as explained below, the variable position may be set to glycine to minimize backbone strain. In addition, as outlined herein, residues need not be classified, they can be chosen as variable and any set of amino acids may be used. Any combination of core, surface and boundary positions can be utilized: core, surface and boundary residues; core and surface residues; core and boundary residues, and surface and boundary residues, as well as core residues alone, surface residues alone, or boundary residues alone.

The classification of residue positions as core, surface or boundary may be done in several ways, as will be appreciated by those in the art. In a preferred embodiment, the classification is done via a visual scan of the original protein backbone structure, including the side chains, and assigning a classification based on a subjective evaluation of one skilled in the art of protein modeling. Alternatively, a preferred embodiment utilizes an assessment of the orientation of the Cα-Cβ vectors relative to a solvent accessible surface computed using only the template Cα atoms, as outlined in U.S. Ser. Nos. 60/061,097, 60/043,464, 60/054, 678, 09/127,926 60/104,612, 60/158,700, 09/419,351, 60/181630, 60/186,904, U.S. patent application, entititled Protein Design Automation For Protein Libraries (Filed: Apr. 14, 2000; Inventor: Bassil Dahiyat) and PCT US98/07254. Alternatively, a surface area calculation can be done.

Suitable core, boundary and surface positions for IA proteins are outlined below.

Once each variable position is classified as either core, surface or boundary, a set of amino acid side chains, and thus a set of rotamers, is assigned to each position. That is, the set of possible amino acid side chains that the program will allow to be considered at any particular position is chosen. Subsequently, once the possible amino acid side chains are chosen, the set of rotamers that will be evaluated at a particular position can be determined. Thus, a core residue will generally be selected from the group of hydrophobic residues consisting of alanine, valine, isoleucine, leucine, phenylalanine, tyrosine, tryptophan, and methionine (in some embodiments, when the α scaling factor of the van der Waals scoring function, described below, is low, methionine is removed from the set), and the rotamer set for each core position potentially includes rotamers for these eight amino acid side chains (all the rotamers if a backbone independent library is used, and subsets if a rotamer dependent backbone is used). Similarly, surface positions are generally selected from the group of hydrophilic residues consisting of alanine, serine, threonine, aspartic acid, asparagine, glutamine, glutamic acid, arginine, lysine and histidine. The rotamer set for each surface position thus includes rotamers for these ten residues. Finally, boundary positions are generally chosen from alanine, serine, threonine, aspartic acid, asparagine, glutamine, glutamic acid, arginine, lysine histidine, valine, isoleucine, leucine, phenylalanine, tyrosine, tryptophan, and methionine. The rotamer set for each boundary position thus potentially includes every rotamer for these seventeen residues (assuming cysteine, glycine and proline are not used, although they can be). Additionally, in some preferred embodiments, a set of 18 naturally occurring amino acids (all except cysteine and proline, which are known to be particularly disruptive) are used.

Thus, as will be appreciated by those in the art, there is a computational benefit to classifying the residue positions, as it decreases the number of calculations. It should also be noted that there may be situations where the sets of core, boundary and surface residues are altered from those described above; for example, under some circumstances, one or more amino acids is either added or subtracted from the set of allowed amino acids. For example, some proteins which dimerize or multimerize, or have ligand binding sites, may contain hydrophobic surface residues, etc. In addition, residues that do not allow helix "capping" or the favorable interaction with an α-helix dipole may be subtracted from a set of allowed residues. This modification of amino acid groups is done on a residue by residue basis.

In a preferred embodiment, proline, cysteine and glycine are not included in the list of possible amino acid side chains, and thus the rotamers for these side chains are not used. However, in a preferred embodiment, when the variable residue position has a φ angle that Is, the dihedral angle defined by 1) the carbonyl carbon of the preceding amino acid; 2) the nitrogen atom of the current residue; 3) the α-carbon of the current residue, and 4) the carbonyl carbon of the current residue) greater than 0°, the position is set to glycine to minimize backbone strain.

Once the group of potential rotamers is assigned for each variable residue position, processing proceeds as outlined in U.S. Ser. No. 09/127,926 and PCT US98/07254. This processing step entails analyzing interactions of the rotamers with each other and with the protein backbone to generate optimized protein sequences. Simplistically, the processing initially comprises the use of a number of scoring functions to calculate energies of interactions of the rotamers, either to the backbone itself or other rotamers. Preferred PDA scoring functions include, but are not limited to, a Van der Waals potential scoring function, a hydrogen bond potential scoring function, an atomic solvation scoring function, a secondary structure propensity scoring function and an electrostatic scoring function. As is further described below, at least one scoring function is used to score each position, although the scoring functions may differ depending on the position classification or other considerations, like favorable interaction with an α-helix dipole. As outlined below, the total energy which is used in the calculations is the sum of the energy of each scoring function used at a particular position, as is generally shown in Equation 1:

$$E_{total} = nE_{vdw} + nE_{as} + nE_{h\text{-}bonding} + nE_{ss} + nE_{elec} \qquad \text{Equation 1}$$

In Equation 1, the total energy is the sum of the energy of the van der Waals potential ($E_{vdw}$), the energy of atomic salvation ($E_{as}$) the energy of hydrogen bonding ($E_{h\text{-}bonding}$), the energy of secondary structure ($E_{ss}$) and the energy of electrostatic interaction ($E_{elec}$). The term n is either 0 or 1, depending on whether the term is to be considered for the particular residue position.

As outlined in U.S. Ser. Nos. 60/061,097, 60/043,464, 60/054,678, 09/127,926, 60/104,612, 60/158,700, 09/419, 351, 60/181630, 60/186,904, U.S. patent application, entitled Protein Design Automation For Protein Libraries (Filed: Apr. 14, 2000; inventor: Bassil Dahiyat) and PCT US98/07254, any combination of these scoring functions, either alone or in combination, may be used. Once the scoring functions to be used are identified for each variable position, the preferred first step in the computational analysis comprises the determination of the interaction of each possible rotamer with all or part of the remainder of the protein. That is, the energy of interaction, as measured by one or more of the scoring functions, of each possible rotamer at each variable residue position with either the backbone or other rotamers, is calculated. In a preferred embodiment, the interaction of each rotamer with the entire remainder of the protein, i.e. both the entire template and all other rotamers, is done. However, as outlined above, it is possible to only model a portion of a protein, for example a domain of a larger protein, and thus in some cases, not all of the protein need be considered. The term "portion", or similar grammatical equivalents thereof, as used herein, with regard to a protein refers to a fragment of that protein. This fragment may range in size from 5–10 amino acid residues to the entire amino acid sequence minus one amino acid. Accordingly, the term "portion", as used herein, with regard to a nucleic refers to a fragment of that nucleic acid. This fragment may range in size from 6–10 nucleotides to the entire nucleic acid sequence minus one nucleotide.

In a preferred embodiment, the first step of the computational processing is done by calculating two sets of interactions for each rotamer at every position: the interaction of the rotamer side chain with the template or backbone (the "singles" energy), and the interaction of the rotamer side chain with all other possible rotamers at every other position (the "doubles" energy), whether that position is varied or floated. It should be understood that the backbone in this case includes both the atoms of the protein structure backbone, as well as the atoms of any fixed residues, wherein the fixed residues are defined as a particular conformation of an amino acid.

Thus, "singles" (rotamer/template) energies are calculated for the interaction of every possible rotamer at every variable residue position with the backbone, using some or all of the scoring functions. Thus, for the hydrogen bonding scoring function, every hydrogen bonding atom of the rotamer and every hydrogen bonding atom of the backbone is evaluated, and the $E_{HB}$ is calculated for each possible rotamer at every variable position. Similarly, for the van der Waals scoring function, every atom of the rotamer is compared to every atom of the template (generally excluding the backbone atoms of its own residue), and the $E_{vdw}$ is calculated for each possible rotamer at every variable residue position. In addition, generally no van der Waals energy is calculated if the atoms are connected by three bonds or less. For the atomic solvation scoring function, the surface of the rotamer is measured against the surface of the template, and the $E_{as}$ for each possible rotamer at every variable residue position is calculated. The secondary structure propensity scoring function is also considered as a singles energy, and thus the total singles energy may contain an $E_{ss}$ term. As will be appreciated by those in the art, many of these energy terms will be close to zero, depending on the physical distance between the rotamer and the template position; that Is, the farther apart the two moieties, the lower the energy.

For the calculation of "doubles" energy (rotamer/rotamer), the interaction energy of each possible rotamer is compared with every possible rotamer at all other variable residue positions. Thus, "doubles" energies are calculated for the interaction of every possible rotamer at every variable residue position with every possible rotamer at every other variable residue position, using some or all of the scoring functions. Thus, for the hydrogen bonding scoring function, every hydrogen bonding atom of the first rotamer and every hydrogen bonding atom of every possible second rotamer is evaluated, and the $E_{HB}$ is calculated for each possible rotamer pair for any two variable positions. Similarly, for the van der Waals scoring function, every atom of the first rotamer is compared to every atom of every possible second rotamer, and the $E_{vdw}$ is calculated for each possible rotamer pair at every two variable residue positions.

For the atomic salvation scoring function, the surface of the first rotamer is measured against the surface of every possible second rotamer, and the $E_{as}$ for each possible rotamer pair at every two variable residue positions is calculated. The secondary structure propensity scoring function need not be run as a "doubles" energy, as it is considered as a component of the "singles" energy. As will be appreciated by those in the art, many of these double energy terms will be close to zero, depending on the physical distance between the first rotamer and the second rotamer; that is, the farther apart the two moieties, the lower the energy.

In addition, as will be appreciated by those in the art, a variety of force fields that can be used in the PDA calculations can be used, including, but not limited to, Dreiding I and Dreiding II [Mayo et al, J. Phys. Chem. 94:8897 (1990)], AMBER [Weiner et al., J. Amer. Chem. Soc. 106:765 (1984) and Weiner et al., J. Comp. Chem. 106:230 (1986)], MM2[Allinger, J. Chem. Soc. 99:8127 (1977), Liljefors et al., J. Corn. Chem. 8:1051 (1987)]; MMP2 [Sprague et al., J. Comp. Chem. 8:581 (1987)]; CHARMM [Brooks et al., J. Comp. Chem. 106:187 (1983)]; GROMOS; and MM3[Allinger et al., J. Amer. Chem. Soc. 111:8551 (1989)], OPLS-AA [Jorgensen et al., J. Am. Chem. Soc. 118:11225–11236 (1995); Jorgensen, W. L.; BOSS, Version 4.1; Yale University: New Haven, Conn. (1999)]; OPLS [Jorgensen et al., J. Am. Chem. Soc.110:1657ff (1988); Jorgensen et al., J Am. Chem. Soc. 112:4768ff (1990)1; UNRES (United Residue Forcefield; Liwo et al., Protein Science 2:1697–1714 (1993); Liwo et al., Protein Science 2:1715–1731 (1993); Liwo et al., J. Comp. Chem. 18:849–873 (1997); Liwo et al., J. Comp. Chem. 18:874–884 (1997); Liwo et al., J. Comp. Chem. 19:259–276 (1998); Forcefield for Protein Structure Prediction (Liwo et al., Proc. Natl. Acad. Sci. U.S.A. 95:5482–5485 (1999)]; ECEPP/3[Liwo et al., J Protein Chem. 13(4):375–80 (1994)]; AMBER 1.1 force field (Weiner, et al., J. Am. Chem. Soc. 106:765–784); AMBER 3.0 force field (U.C. Singh et al., Proc. Natl. Acad. Sci. U.S.A. 82:755–759); CHARMM and CHARMM22 (Brooks et al., J. Comp. Chem. 4:187–217); cvff3.0[Dauber-Osguthorpe, et al., Proteins: Structure, Function and Genetics, 4:31–47 (1988)]; cff91 Maple, et al., J. Comp. Chem 15:162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.), all of which are expressly incorporated by reference.

Once the singles and doubles energies are calculated and stored, the next step of the computational processing may occur. As outlined in U.S. Ser. No. 09/127,926 and PCT US98/07254, preferred embodiments utilize a Dead End Elimination (DEE) step, and preferably a Monte Carlo step.

PDA, viewed broadly, has three components that may be varied to alter the output (e.g. the primary library): the scoring functions used in the process; the filtering technique, and the sampling technique.

In a preferred embodiment, the scoring functions may be altered. In a preferred embodiment, the scoring functions outlined above may be biased or weighted in a variety of ways. For example, a bias towards or away from a reference sequence or family of sequences can be done; for example, a bias towards wild-type or homolog residues may be used. Similarly, the entire protein or a fragment of it may be biased; for example, the active site may be biased towards wild-type residues, or domain residues towards a particular desired physical property can be done. Furthermore, a bias towards or against increased energy can be generated. Additional scoring function biases include, but are not limited to applying electrostatic potential gradients or hydrophobicity gradients, adding a substrate or binding partner to the calculation, or biasing towards a desired charge or hydrophobicity.

In addition, in an alternative embodiment, there are a variety of additional scoring functions that may be used. Additional scoring functions include, but are not limited to torsional potentials, or residue pair potentials, or residue entropy potentials. Such additional scoring functions can be used alone, or as functions for processing the library after it is scored initially. For example, a variety of functions derived from data on binding of peptides to MHC (Major Histocompatibility Complex) can be used to rescore a library in order to eliminate proteins containing sequences which can potentially bind to MHC, i.e. potentially immunogenic sequences.

In a preferred embodiment, a variety of filtering techniques can be done, including, but not limited to, DEE and its related counterparts. Additional filtering techniques include, but are not limited to branch-and-bound techniques for finding optimal sequences (Gordon and Mayo, Structure Fold. Des. 7:1089–98, 1999), and exhaustive enumeration of sequences.

As will be appreciated by those in the art, once an optimized sequence or set of sequences is generated, a variety of sequence space sampling methods can be done, either in addition to the preferred Monte Carlo methods, or instead of a Monte Carlo search. That is, once a sequence or set of sequences is generated, preferred methods utilize sampling techniques to allow the generation of additional, related sequences for testing.

These sampling methods can include the use of amino acid substitutions, insertions or deletions, or recombinations of one or more sequences. As outlined herein, a preferred embodiment utilizes a Monte Carlo search, which is a series of biased, systematic, or random jumps. However, there are other sampling techniques that can be used, including Boltzman sampling, genetic algorithm techniques and simulated annealing. In addition, for all the sampling techniques, the kinds of jumps allowed can be altered (e.g. random jumps to random residues, biased jumps (to or away from wild-type, for example), jumps to biased residues (to or away from similar residues, for example, etc.). Jumps where multiple residue positions are coupled (two residues always change together, or never change together), jumps where whole sets of residues change to other sequences (e.g., recombination). Similarly, for all the sampling techniques, the acceptance criteria of whether a sampling jump is accepted can be altered.

In addition, it should be noted that the preferred methods of the invention result in a rank ordered list of sequences; that is, the sequences are ranked on the basis of some objective criteria. However, as outlined herein, it is possible to create a set of non-ordered sequences, for example by generating a probability table directly (for example using SCMF analysis or sequence alignment techniques) that lists sequences without ranking them. The sampling techniques outlined herein can be used in either situation.

In a preferred embodiment, Boltzman sampling is done. As will be appreciated by those in the art, the temperature criteria for Boltzman sampling can be altered to allow broad searches at high temperature and narrow searches close to local optima at low temperatures (see e.g., Metropolis et al., J. Chem. Phys. 21:1087, 1953).

In a preferred embodiment, the sampling technique utilizes genetic algorithms, e.g., such as those described by Holland (Adaptation in Natural and Artifical Systems, 1975, Ann Arbor, U. Michigan Press). Genetic algorithm analysis generally takes generated sequences and recombines them computationally, similar to a nucleic acid recombination event, in a manner similar to "gene shuffling". Thus the "jumps" of genetic algorithm analysis generally are multiple position jumps. In addition, as outlined below, correlated multiple jumps may also be done. Such jumps can occur with different crossover positions and more than one recombination at a time, and can involve recombination of two or more sequences. Furthermore, deletions or insertions (random or biased) can be done. In addition, as outlined below, genetic algorithm analysis may also be used after the secondary library has been generated.

In a preferred embodiment, the sampling technique utilizes simulated annealing, e.g., such as described by Kirkpatrick et al. [Science, 220:671–680 (1983)]. Simulated annealing alters the cutoff for accepting good or bad jumps by altering the temperature. That Is, the stringency of the cutoff Is altered by altering the temperature. This allows broad searches at high temperature to new areas of sequence space, altering with narrow searches at low temperature to explore regions in detail.

In addition, as outlined below, these sampling methods can be used to further process a first set to generate additional sets of IA proteins.

The computational processing results in a set of optimized IA protein sequences. These optimized IA protein sequences are generally significantly different from the wild type insulin sequence from which the backbone was taken. That is, each optimized IA protein sequence preferably comprises at least about 2–50% variant amino acids from the starting or wild type sequence, with at least about 25% being preferred, with at least about 15–20% changes being more preferred and at least 4–15% being particularly preferred.

In a preferred embodiment, the IA proteins of the invention have 1, 2, 3, 4, 5, 6, 7, 8, 9, 10, 11, 12, 13, 14, 15, 15, 17, 18, 19, 20, 21, 22, 23, 24, 25, 26, 27, 28, 29, or 30 different residues from the human insulin sequence.

In one aspect of this embodiment, the IA protein of the invention has at least one different residue from the human insulin sequence. Preferred IA protein sequences comprising a substitution of one amino acid residye are shown in FIGS. 4B, 4C, 4D, 4F, and 4G.

In another aspect of this embodiment, the IA protein of the invention has at least two different residues from the human insulin sequence. Preferred IA protein sequences comprising a substitution of two amino acid residues are shown in FIGS. 3C, 3F, 4A, and 4E.

In another aspect of this embodiment, the IA protein of the invention has at least three different residues from the human insulin sequence. A preferred IA protein sequence comprising a substitution of three amino acid residues is shown in FIG. 3E.

In another aspect of this embodiment, the IA protein of the invention has at least four different residues from the human insulin sequence. Preferred IA protein sequences comprising a substitution of four amino acid residues are shown in FIGS. 3C, 3F, 4A, and 4E.

In another aspect of this embodiment, the IA protein of the invention has at least five different residues from the human insulin sequence.

In another aspect of this embodiment, the IA protein of the invention has at least six different residues from the human insulin sequence. A preferred IA protein sequence comprising a substitution of six amino acid residues is shown in FIG. 5A. A preferred IA protein sequence comprising a substitution of two amino acid residues and a deletion of four amino acid residues is shown in FIG. 3G.

In another aspect of this embodiment, the IA protein of the invention has at least seven different residues from the human insulin sequence.

In another aspect of this embodiment, the IA protein of the invention has at least eight different residues from the human insulin sequence.

In another aspect of this embodiment, the IA protein of the invention has at least nine different residues from the human insulin sequence.

In another aspect of this embodiment, the IA protein of the invention has at least ten different residues from the human insulin sequence.

In another aspect of this embodiment, the IA protein of the invention has at least eleven different residues from the human insulin sequence.

In another aspect of this embodiment, the IA protein of the invention has at least twelve different residues from the human insulin sequence.

In another aspect of this embodiment, the IA protein of the invention has at least thirteen different residues from the human insulin sequence.

In another aspect of this embodiment, the IA protein of the invention has at least fourteen different residues from the human insulin sequence. A preferred IA protein sequence comprising a substitution of fourteen amino acid residues is shown in FIG. 5B.

In another aspect of this embodiment, the IA protein of the invention has at least fifteen different residues from the human insulin sequence.

In another aspect of this embodiment, the IA protein of the invention has at least sixteen different residues from the human insulin sequence. A preferred IA protein sequence comprising a substitution of sixteen amino acid residues is shown in FIG. 5C.

In another aspect of this embodiment, the IA protein of the invention has at least twenty different residues from the human insulin sequence. A preferred IA protein sequence comprising a substitution of twenty amino acid residues is shown in FIG. 3A.

Thus, in the broadest sense, the present invention is directed to IA proteins that have insulin activity.

By "insulin activity" or "IA" herein is meant that the IA protein exhibits at least one, and preferably more, of the biological functions of an insulin, as defined below. In one embodiment, the biological function of an IA protein is altered, preferably improved, over the corresponding biological activity of an insulin.

By "protein" herein is meant at least two covalently attached amino acids, which includes proteins, polypeptides, oligopeptides and peptides. The protein may be made up of naturally occurring amino acids and peptide bonds, or synthetic peptidomimetic structures, i.e., "analogs" such as peptoids [see Simon et al., Proc. Natl. Acd. Sci. U.S.A. 89(20:9367–71 (1992)], generally depending on the method of synthesis. Thus "amino acid", or "peptide residue", as used herein means both naturally occurring and synthetic amino acids. For example, homo-phenylalanine, citrulline, and noreleucine are considered amino acids for the purposes of the invention. "Amino acid" also includes imino acid residues such as proline and hydroxyproline. In addition, any amino acid representing a component of the IA proteins can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon Its composition and chemical configuration. Such derivatives have the property of greatly increased stability, and therefore are advantageous in the formulation of compounds which may have longer in vivo half lives, when administered by oral, intravenous, intramuscular, intraperitoneal, topical, rectal, intraocular, or other routes. In the preferred embodiment, the amino acids are in the (S) or L-configuration. If non-naturally occurring side chains are used, non-amino acid substituents may be used, for example to prevent or retard in vivo degradations. Proteins including non-naturally occurring amino acids may be synthesized or in some cases, made recombinantly; see van Hest et al., FEBS Lett 428:(1–2) 68–70 May 22, 1998 and Tang et al., Abstr. Pap Am. Chem. S218:U138-U138 Part 2 Aug. 22, 1999, both of which are expressly incorporated by reference herein.

Additionally, modified amino acids or chemical derivatives of amino acids of consensus or fragments of IA proteins, according to the present invention may be provided, which polypeptides contain additional chemical moieties or modified amino acids not normally a part of the protein. Covalent and non-covalent modifications of the protein are thus included within the scope of the present invention. Such modifications may be introduced into an IA polypeptide by reacting targeted amino acid residues of the polypeptide with an organic derivatizing agent that is capable of reacting with selected side chains or terminal residues. The following examples of chemical derivatives are provided by way of illustration and not by way of limitation.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3pyridinyl)alanine, D- or L-(2-pyrazinyl)alanine, D- or L-(4-isopropyl)-phenylglycine, D-(trifluoromethyl) glycine, D-(trifluoromethyl)-phenylalanine, D-p-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole (alkyl)alanines, and D- or L-alkylainines where alkyl may be substituted or unsubstituted methyl, ethyl, propyl, hexyl, butyl, pentyl, isopropyl, iso-butyl, sec-isotyl, iso-pentyl, non-acidic amino acids, of C1–C20.

Acidic amino acids can be substituted with non-carboxylate amino acids while maintaining a negative charge, and derivatives or analogs thereof, such as the non-limiting examples of (phosphono)alanine, (phosphono) glycine, (phosphono)leucine, (phosphono)isoleucine, (phosphono)threonine, or (phosphono)serine; or sulfated (e.g., —SO$_3$H) threonine, serine, tyrosine.

Other substitutions may include unnatural hyroxylated amino acids that may be made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, Isobutyl, t-butyl, octyl, decyl, tetradecyl, hexadecyl, eicosyl, tetracisyl and the like. Preferred alkyl groups herein contain 1 to 12 carbon atoms. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, and nitrogen being preferred. Alkyl includes substituted alkyl groups. By "substituted alkyl group" herein is meant an alkyl group further comprising one or more substitution moieties. A preferred heteroalkyl group is an alkyl amine. By "alkyl amine" or grammatical equivalents herein is meant an alkyl group as defined above, substituted with an amine group at any position. In addition, the alkyl amine may have other substitution groups, as outlined above for alkyl group. The amine may be primary (—NH$_2$R), secondary (—NHR$_2$), or tertiary (—NR$_3$). Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the IA polypeptides can be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of IA polypeptides of the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chlommercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

The insulin may be from any number of organisms, with insulins from mammals being particularly preferred. Suitable mammals include, but are not limited to, rodents (rats, mice, hamsters, guinea pigs, etc.), primates, farm animals (including sheep, goats, pigs, cows, horses, etc) and in the most preferred embodiment, from humans (the sequence of which is depicted in FIG. 1). As will be appreciated by those in the art, insulins based on insulins from mammals other than humans may find use in animal models of human disease. The GenBank accession numbers for a variety of mammalian insulin species is as follows: bovine, IPBO; dog, IPDG; sheep, INSH; cat, INCT; pig, IPPG; mouse, INMS1, INMS2; rat, IPRT1, IPRT2; horse, IPHO; rabbit, INRB; guinea pig, IPGP; hamster, INHY; goat, INGT, chimpanzee, A42179; green monkey, B42179; and human IPHU.

The IA proteins of the invention exhibit at least one biological function of an insulin. By "insulin" or herein is meant a wild type insulin, an allelic variant thereof or a hybrid formed from a combination of an A-chain of one species and a B-chain of another species. Thus, insulin refers to all forms of insulins that are active in accepted insulin assays.

The IA proteins of the invention exhibit at least one biological function of an insulin By "biological function" or "biological property" herein is meant any one of the properties or functions of an insulin, including, but not limited to, the ability to bind to a naturally occurring insulin receptor; the ability to bind to a recombinant insulin receptor; the ability to bind to a cell comprising an insulin receptor, the ability to induce autophosphorylation of an insulin receptor [Combettes-Souverain and Issad, Diabetes Metab. 24(6) :477–89 (1998)]; the ability to regulate a Na+/K=-ATPase [Sweeney and Klip, Mol. Cell. Biochem. 182(1–2):121–33 (1998)]; the ability to regulate the Ras activation/inactivation cycle [Ceresa and Pessin, Mol. Cell. Biochem. 182(1–2):23–9 (1998)]; the ability to treat type I diabetes, the ability to treat type 2 diabetes; the ability to treat an insulin-dependent disorder; the ability to treat hyperglycemia; the ability to treat familial hyperproinsulinemia; the ability to regulate carbohydrate metabolism; the ability to regulate skeletal muscle protein turnover [Grizard et al., Reprod. Nutr. Dev. 39(1):61–74 (1999)]; the ability to modulate intracellular processes including, but not limited to cellular metabolism, cell proliferation, and cell differentiation [Rizzo and Romero, J. Basic Clin. Physiol. Pharmacol. 9(2–4):167–95 (1998)]; the ability to form multimers; the ability to complex zinc; and the ability to bind a phenolic preservative.

All of these IA proteins will exhibit at least 20% of the receptor binding or biological activity as the wild type insulin. More preferred are IA proteins that exhibit at least 50%, even more preferred are IA proteins that exhibit at least 90%, and most preferred are IA proteins that exhibit more than 100% of the receptor binding or biological activity as the wild type insulin. Biological assays, receptor binding assays, and other assays for measuring insulin activity, stability, conformation, potency, etc. are described e.g., in the Examples, in U.S. Pat. Nos. 4,421,685; 4,992,417; 5,008,241; 5,506,202; 5,514,646; 5,559,094; 5,618,913; 5,621,073; 5,663,291; 5,700,662; and 6,034,054 and further by Marki et al. [Hoppe Seylers Z. Phsiol. Chem, 360(11):1619–32 (1979)]; Hu et al. [Biochemistry 32(10):2631–5 (1993)]; Schwartz et al. [Proc. Natl. Acad. Sci. U.S.A. 84(18):6408–11 (1987)]; Kitagawa et al. [Biochemistry 23(7):1405–13 (1984)]; Kobayashi et al. [Biochem. Biophys. Res. Commun. 107(1):329–36 (1982)]; Shoelson et al. [Biochemistry 31(6):1757–67 (1992)]; Hua et al. [Nature 354:238–241 (1991)], Bao et al. [Proc. Natl. Acad. Sci. U.S.A. 94:2975–2980 (1997)]; Kitagawa et. al. [Biochemistry 23:1405–1413 (1984)]; Nakagawa and Tager [Biochemistry 31:3204–3214 (1992)]; Brader et al. [Biochemistry 30:6636–6645 (1991)]; and references cited therein, all of which are expressly incorporated as reference.

In one embodiment, at least one biological property of the IA protein is altered when compared to the same property of insulin. As outlined above, the invention provides IA nucleic acids encoding IA polypeptides. The IA polypeptide preferably has at least one property, which is substantially different from the same property of the corresponding naturally occurring insulin. The property of the IA polypeptide is the result the PDA analysis of the present invention.

The term "altered property" or grammatical equivalents thereof in the context of a polypeptide, as used herein, refer to any characteristic or attribute of an IA polypeptide that can be selected or detected and compared to the corresponding property of a naturally occurring insulin protein. These properties include, but are not limited to oxidative stability, prolonged shelf-life; thermal stability, alkaline stability, pH activity profile, resistance to proteolytic degradation, kinetic association ($K_{on}$) and dissociation ($K_{off}$) rate, protein folding, including an immune response, ability to bind to an insulin receptor, ability to be secreted, ability to oligomerize, ability to form dimers, ability to form tetramers, ability to form hexamers, ability to complex zinc, ability to bind phenolic preservative, ability to modulate potency, preference for the R state, preference for the T state, ability to signal, ability to modulate cell proliferation, ability to be modified by phosphorylation or glycosylation, ability to treat hyperglycemia, ability to treat diabetes mellitus, ability to treat type 1 diabetes, ability to treat type 2 diabetes, ability to treat an insulin-dependent disorder, ability to treat an insulin-independent disorder, ability to achieve hormonal homeostasis in a patient; ability to be cleared from the blood of a diabetic patient.

Unless otherwise specified, a substantial change in any of the above-listed properties, when comparing the property of an IA polypeptide to the property of a naturally occurring insulin protein is preferably at least a 20%, more preferably, 50%, more preferably at least a 2-fold increase or decrease.

A change in oxidative stability is evidenced by at least about 20%, more preferably at least 50% increase of activity of an IA protein when exposed to various oxidizing conditions as compared to that of insulin. Oxidative stability is measured by known procedures.

A change in alkaline stability is evidenced by at least about a 50% or greater increase or decrease (preferably increase) in the half life of the activity of an IA protein when exposed to increasing or decreasing pH conditions as compared to that of insulin. Generally, alkaline stability is measured by known procedures.

A change in thermal stability is evidenced by at least about a 50% or greater increase or decrease (preferably increase) in the half life of the activity of an IA protein when exposed to a relatively high temperature and neutral pH as compared to that of insulin. Generally, thermal stability is measured by known procedures. In a preferred embodiment, an IA protein of the invention has increase thermal stability when compared to the human insulin. Such an IA protein preferably has an amino acid sequence which comprises substitution of one or more amino acid residues when compared to the amino acid sequence of human insulin. In one aspect of this embodiment, the amino acid sequence of the IA protein comprises 2, 3, 4, 5, 6, 7, 8, 9, 10, or more substitutions when compared to the amino acid sequence of human insulin.

Similarly, IA proteins, for example are experimentally tested and validated in in vivo and in in vitro assays. Suitable assays include, but are not limited to, e.g., examining their binding affinity to natural occurring or variant receptors and to high affinity agonists and/or antagonists. In addition to cell-free biochemical affinity tests, quantitative comparison are made comparing kinetic and equilibrium binding constants for the natural receptor to the naturally occurring insulin and to the IA proteins. The kinetic association rate ($K_{on}$ and dissociation rate ($K_{off}$), and the equilibrium binding constants ($K_d$) can be determined using surface plasmon resonance on a BIAcore instrument following the standard procedure in the literature [Pearce et al., Biochemistry 38:81–89 (1999)]. Comparing the binding constant between a natural receptor and its corresponding naturally occurring insulin with the binding constant of a natural occurring receptor and an IA protein are made in order to evaluate the sensitvity and specificity of the IA protein. Preferably, binding affinity of the IA protein to natural receptors and agonists increases relative to the naturally occurring insulin, while antagonist affinity decreases. IA proteins with higher affinity to antagonists relative to the insulin may also be generated by the methods of the invention.

In one preferred embodiment, an IA protein of the invention has modulated potency when compared to the human insulin. The term "modulated potency" herein means that an IA protein leads to an increase (more potent) or a decrease (less potent) in response when compared to the human insulin. The response includes any response due to the biological property of an IA protein as defined above. In one aspect of this embodiment, the modulated potency is brought about by a faster acting IA protein, a slower acting IA protein, a longer acting IA protein, a shorter acting IA protein, or causing a similar response as the human insulin at a lower concentration. Such an IA protein preferably has an amino acid sequence which comprises substitutions of four or more amino acid residues when compared to the amino acid sequence of human insulin. In one aspect of this embodiment, the amino acid sequence of the IA protein comprises 5, 6, 7, 8, 9, 10, or more substitutions when compared to the amino acid sequence of human insulin.

In one preferred embodiment, an IA protein of the invention shows increased hexamer formation when compared to the human insulin. The term "increased hexamer formation" herein means that an IA protein forms a hexamer at a lower concentration than the human insulin or that the hexamer formed by an IA protein is more stable than those formed by human insulin. Such an IA protein preferably has an amino acid sequence which comprises substitution of one or more amino acid residues when compared to the amino acid sequence of human insulin. In one aspect of this embodiment, the amino acid sequence of the IA protein comprises 2, 3, 4, 5, 6, 7, 8, 9, 10, or more substitutions when compared to the amino acid sequence of human insulin.

In one preferred embodiment, an IA protein of the invention has an increased preference for the R state when compared to the human insulin. The term "increased preference for the R state" herein means a greater portion of an IA protein is in the R state than in the T state when compared to human insulin. Such an IA protein preferably has an amino acid sequence which comprises substitution of three or more amino acid residues when compared to the amino acid sequence of human insulin. In one aspect of this embodiment, the amino acid sequence of the IA protein comprises 4, 5, 6, 7, 8, 9, 10, or more substitutions when compared to the amino acid sequence of human insulin.

As described in the art, both zinc and a phenolic preservative are essential to achieve a complex that is stable ana capable of rapid dissociation and onset of action. The hexamer complex consists of two zinc ions per hexamer of insulin, and at least three molecules of a phenolic preservative. "Phenolic preservative" as used herein refers to clorocresol, m-cresol, phenol, or mixtures thereof. In a preferred embodiment, an IA protein does not bind phenolic preservatives or binds less that insulin.

High insulin concentrations lead to oligomerization, the formation of dimers, tetramers and hexamers. In a preferred embodiment, an IA protein oligomerizes at a lower concentration as the corresponding wild type insulin.

Insulin preparations for treatment of diabetes are administered in adequate therapeutic amounts of the active compound to achieve hormonal homeostasis. In a preferred embodiment, an IA protein is more potent than natural insulin in vitro. In one aspect of this embodiment, it is believed that the therapeutic amount of the IA protein to achieve homeostasis in diabetic patient or In animal models is less than the therapeutic amount of the wild type insulin. Various animal models are available, for example the BB mouse [Nakbookda et al., Diabetologia 14(3):199–207 (1978)] and the NOD (non-obese-diabetic) mouse in which diabetes develops spontaneously [Prochazka et al., Science 237(4812):286–9 (1987)].

Insulin clearance from the blood is mediated by the insulin receptor on cells. In a preferred embodiment, an IA protein binds to an insulin receptor more tightly than wild type insulin. In one aspect of this embodiment, it is believed that IA protein is cleared from the blood of a patient at a faster rate than wild type insulin. As a consequence thereof, it is further believed that in treatment of diabetes that vascular toxicity associated with the growth promoting effects of circulating insulin may be lessened by the use of IA proteins.

As described above, one biological function of an IA protein is the ability of the IA protein to bind to cells comprising an insulin receptor. GenBank Accession numbers for Insulin receptors OR) are available for various species, e.g., human, INHUR, P06213, NP_000199; mouse, A34157, P15208; and rat, A36080, P15127.

In a preferred embodiment, the assay system used to determine IA is an in vitro system using cells that either express endogenous insulin receptors or cells stably transfected with the gene encoding the human insulin receptor or an insulin receptor from another species, known to bind human insulin, e.g., mouse. In this system, cell proliferation is measured as a function of BrdU incorporation, which is incorporated into the nucleic acid of proliferating cells. A decrease above background of at least about 10%, with at least about 20% being preferred, with at least about 30% being more preferred and at least about 50%, 75% and 90% being especially preferred is an indication of IA.

In another preferred embodiment, autophosphorylation of the insulin receptor, which occurs after insulin binding is determined using known phosphorylation assays.

In a preferred embodiment, the antigenic profile In the host animal of the IA protein is similar, and preferably identical, to the antigenic profile of the host insulin; that is, the IA protein does not significantly stimulate the host organism (e.g. the patient) to an Immune response; that is, any immune response is not clinically relevant and there is no allergic response or neutralization of the protein by an antibody. That is, in a preferred embodiment, the IA protein does not contain additional or different epitopes from the insulin. By "epitope" or "determinant" herein is meant a portion of a protein which will generate and/or bind an antibody. Thus, in most instances, no significant amount of antibodies are generated to a IA protein. In general, this is accomplished by not significantly altering surface residues, as outlined below nor by adding any amino acid residues on the surface which can become glycosylated, as novel glycosylation can result in an immune response.

The IA proteins and nucleic acids of the invention are distinguishable from naturally occurring insulins. By "naturally occurring" or "wild type" or grammatical equivalents, herein is meant an amino acid sequence or a nucleotide sequence that is found in nature and includes allelic variations; that is, an amino acid sequence or a nucleotide sequence that usually has not been intentionally modified. Accordingly, by "non-naturally occurring" or "synthetic" or "recombinant" or grammatical equivalents thereof, herein is meant an amino acid sequence or a nucleotide sequence that is not found in nature; that is, an amino acid sequence or a nucleotide sequence that usually has been intentionally modified. It is understood that once a recombinant nucleic acid is made and reintroduced into a host cell or organism, it will replicate non-recombinantly, i.e., using the in vivo cellular machinery of the host cell rather than in vitro manipulations, however, such nucleic acids, once produced recombinantly, although subsequently replicated non-recombinantly, are still considered recombinant for the purpose of the invention. A representative amino acid sequences of a naturally occurring human insulin is shown in FIG. 1. It should be noted that unless otherwise stated, all positional numbering of IA proteins and IA nucleic acids is based on these sequences. That is, as will be appreciated by those in the art, an alignment of insulin proteins and IA proteins can be done using standard programs, as is outlined below, with the identification of "equivalent" positions between the two proteins. Thus, the IA proteins and nucleic acids of the invention are non-naturally occurring; that is, they do not exist in nature.

Thus, in a preferred embodiment, the IA protein has an amino acid sequence that differs from a wild-type insulin sequence by at least 2% of the residues. That is, the IA proteins of the invention are less than about 98% identical to an insulin amino acid sequence. Accordingly, a protein is an "IA protein" If the overall homology of the protein sequence to the amino acid sequence shown In FIG. 1A or FIG. 1B is preferably less than about 98%, more preferably less than about 95%, even more preferably less than about 90% and most preferably less than 85%. In some embodiments the homology will be as low as about 75 to 80%. In other embodiments the homology will be as low 5–70%. Stated differently, based on the human insulin sequence of 51 residues (see FIG. 1B), IA proteins have at least about 1 residue that differs from the human insulin sequence (2%), with IA proteins having from 2 residues to upwards of 25 residues being different from the human insulin sequence. Preferred IA proteins have 1–20 different residues with from about 2 to about 10 being particularly preferred (that is, 4–20% of the protein is not identical to human insulin).

Homology in this context means sequence similarity or identity, with Identity being preferred. As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Nat. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in: Altschul et al., J. Mol. Biol. 215, 403–410, (1990); Altschul et al., Nucleic Acids Res. 25:3389–3402 (1997); and Karin et Proc. Natl. Acad. Sci. U.S.A. 90:5873–5787 (1993). A particularly useful BLAST program is the WU-BLAST-2 program which was obtained from Altschul et al., Methods in Enzymology, 266:460–480 (1996); http.//blast.wust1/edu/blast/README.html]. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucl. Acids Res., 25:3389–3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequence of FIG. 1, it is understood that in one embodiment, the percentage of sequence identity will be determined based on the number of identical amino acids in relation to the total number of amino acids. Thus, for example, sequence identity of sequences shorter than that shown in FIG. 1, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Thus, IA proteins of the present invention may be shorter or longer than the amino acid sequence shown in FIG. 1. Thus, in a preferred embodiment, included within the definition of IA proteins are portions or fragments of the sequences depicted herein. Fragments of IA proteins are considered IA proteins if a) they share at least one antigenic epitope; b) have at least the indicated homology; c) and preferably have IA biological activity as defined herein.

In a preferred embodiment, as is more fully outlined below, the IA proteins include further amino acid variations, as compared to a wild type insulin, than those outlined herein. In addition, as outlined herein, any of the variations depicted herein may be combined in any way to form additional novel IA proteins.

In addition, IA proteins can be made that are longer than those depicted in the figures, for example, by the addition of epitope or purification tags, as outlined herein, the addition of other fusion sequences, etc. For example, the IA proteins of the invention may be fused to other therapeutic proteins such as IL-11 or to other proteins such as Fc or serum albumin for pharmacokinetic purposes. See for example U.S. Pat. Nos. 5,766,883 and 5,876,969, both of which are expressly incorporated by reference.

In a preferred embodiment, the IA proteins are globally redesigned for improved stability. In one aspect of this embodiment, the IA protein comprises variable residues in core residues.

In one embodiment, the variable core positions are altered to any of the other 19 amino acids. In a preferred embodiment, the variable core residues are chosen from Ala, Val, Phe, Ile, Leu, Tyr, Trp and Met. In another preferred embodiment, the variable core residues are chosen from Ala, Val, Leu, Ile, Phe, Tyr, and Trp. In another preferred embodiment, the variable core residues are chosen from Ala, Val, Ieu, Ile, and Gly.

Human insulin core residues are as follows: positions A2, A3, A16, B11, B15, and B24, whereby "A" refers to a residue in the A-chain of insulin and the number identifies the position within the A-chain. Accordingly, "B" refers to a residue in the B-chain of insulin and the number identifies the position within the B-chain. In the context of the mature insulin, the A-chain comprises residues 1–21 and the B-chain residues 22–51 of the amino acid sequence shown in FIG. 1B. In some embodiments, when referred explicitly to the B-chain, residues 22–51 are also referred to B1–B30, respectively. Accordingly, in a preferred embodiment, IA proteins have variable positions selected from positions A2, A3, A16, B11, B15, and B24.

In a preferred embodiment, the IA protein of the invention has a sequence that differs from a wild-type human insulin protein in at least one amino acid position selected from positions A2, A3, A16, B11, B15, or B24.

Preferred amino acid substitutions for each position are as follows: Position A3: Ile; position A16: Tyr; position B11: Ile; and position B24: Tyr. The preferred amino acids in position A2 is Ile (wild type) and B15 is Leu (wild type). Any combination of the above-listed amino acid substitutions is possible and should result in an IA protein that is more stable than insulin.

In a preferred embodiment, IA proteins have variable positions selected solely from core residues of human insulin. Alternatively, at least a majority (51%) of the variable positions are selected from core residues, with at least about 75% of the variable positions being preferably selected from core residue positions, and at least about 90% of the variable positions being particularly preferred. A specifically preferred embodiment has only core variable positions altered as compared to human insulin.

In another aspect of this preferred embodiment, globally redesigned IA proteins comprise variable residues in boundary residues.

Human insulin boundary residues are as follows: positions A5, A15, A17, A19, A21, B2, B3, B4, B8, B12, B14, B18B, B22, B26, and B28. Accordingly, in a preferred embodiment, IA proteins have variable positions selected from these positions.

In a preferred embodiment, the IA protein of the invention has a sequence that differs from a wild-type human insulin protein in at least one amino acid position selected from positions A5, A15, A17, A19, A21, B2, B3, B4, B8, B12, B14, B18, B22, B26, or B28.

Preferred amino acid substitutions for each position are as follows: Position A5: Glu, and Arg; position A15: Glu, Leu, and Arg; position A17: Lys, Trp, Gln, and Tyr, position Al 9: Phe; position A21: Asp, Gln, and Arg; position B2: Lys, position B4: Phe and Tyr; position B8: Lys, Leu, Glu; position B12: Arg and Lys; position B14: Glu and Trp; position B18: Lys; position B22: Gln; position B26: Phe; and position B28: Phe and Asn. The preferred amino acids in position B3 is Asn (wild type). Any combination of the above-listed amino acid substitutions is possible and should result in an IA protein that is more stable than insulin.

In another aspect of this preferred embodiment, globally redesigned IA proteins comprise variable residues in surface residues.

Human insulin surface residues are as follows: positions A1, A4, A8, A9, A10, A12, A13, A14, A18, B1, B5, B6, B9, B10, B13, B11, B17, B21, B25 B27, B29, and B30. Accordingly, in embodiment, IA proteins have variable positions selected from these positions.

In a preferred embodiment, the IA protein of the invention has a sequence that differs from a wild-type human insulin protein in at least one amino acid position selected from positions A1, A4, A8, A9, A10, A12, A13, A14, A18, B1, B5, B6, B9, B10, B13, B16, B17, B21, B25, B27, B29, and B30.

Preferred amino acid substitutions for each position are as follows: Position A1: Asn; position A4: Gln; position A8: Asp and Gln; position A9: Asn and Gln; position A10: Gln; position A12: Lys, Gln, and Thr; position A13:Glu; position A14: Arg and Lys; position A18: Ser, Glu, Lys, and Arg; position B1: Asp; position B5: Glu, Lys, and Arg; position B6: Glu, Gln, Lys, and Arg; position B9: Arg, Glu, and Gln; position B10: Arg, Glu, and Gln; position B13: Asn; position B16: Glu and Arg; position B17: Lys; position B21: Arg, Gln, and Lys; position B25: Asn; position B27: Asp; position B29: Thr, Ser, Asn, and Glu; and position B30: Ser and Ala. Any combination of the above-listed amino acid substitutions is possible and should result in an IA protein that is more stable than insulin.

In a preferred embodiment, the IA protein comprises amino acid substitutions from core residues, and/or boundary residues, and/or surface residues.

In a preferred aspect of this embodiment, the IA protein comprises the amino acid sequence shown in FIG. 5A. This sequence shows 6 amino acid substitution (11–12% divergence from the wild type insulin sequence) and comprises A1-N, A10-Q, A16-Y, B1-D, B25-N, and B27-D.

In another aspect of this embodiment, the IA protein comprises the amino acid sequence shown in FIG. 5B. This sequence shows 14 mutation (27–28% divergence from the wild type insulin sequence) and comprises A1-N, A10-Q, A16Y, A17-Y, A19-F, B1-D, B2-K, B4-F, B11-I, B12-R14-W, B25-N, B26F, and B27-D.

In one preferred aspect of this embodiment, the IA protein comprises the amino acid sequence shown in FIG. 5C. This sequence shows 16 mutation (31–34% divergence from the wild type insulin sequence) and comprises A1-N, A10-Q, A16-Y, A17-Y, A19-F, B1-D, B2-K, B4-F, B8-L, B11-I, B12-R, B14-W, B25-N, B26-F, B27-D, and B28-N.

The following cysteine residues are linked via disulfide bonds with one another in human insulin: A6–A11, A7–B7, and A20–B19. In a preferred embodiment, IA proteins are provided which comprise a disulfide bond replacement in one aspect of this embodiment, the following residues were considered in the PDA calculation: A2, A3, A5, A6, A7, A11, A15, A16, A19, A20, B2, B7, B11, B15, B18, B19, B22, and B24. Accordingly, in a preferred embodiment, IA proteins have variable positions selected from these positions.

In a preferred embodiment, the IA protein of the invention has a sequence that differs from a wild-type human insulin protein in at least one amino acid position selected from positions A2, A3, A5, A6, A7, A11, A15, A16, A19, A20, B2, B7, B11, B15, B18, B19, B22, and B24.

Preferred amino acid substitutions for each position are as follows: Position A2:Leu; position A3: Ile; position A5: Arg, Val, and Glu; position A6: Ala; position A7: Ala and Ser; position A11: Ala; position A15: Leu, Glu, and Arg; position A16: Ile; position A19: Phe; position A20: Asp, Ala, and Ser; position B2: Asp, Asn, Glu, Gln, Lys, and Arg; position B7: Tyr and Hsp; position B15: Leu; position B19: Ala; and position B22: Gln. Any combination of the above-listed amino acid substitutions is possible and should result in an IA protein that is more stable than insulin. Preferred amino acids at position B11, B18, B24 are Leu, Val, and Phe, respectively (all wild type).

In one aspect of this embodiment, the IA protein comprises the amino acid sequence shown in FIG. 3A. This sequence shows 20 mutation (39–40% divergence from the wild type insulin sequence) and comprises A1-N, A2-I, A6-A, A7-S, A10-Q, A11-A, A16I, A17-Y, A19-F, A20-D, B1-D, B4-F, B7-Y, B11I, B12-R, B14-W, B19-A, B25-N, B26F, and B27-D.

In another aspect of this embodiment, the following residues were considered for a disulfide bond replacement: A3, A7, B2, B4, B7, and B11. Accordingly, in a preferred embodiment, IA proteins have variable positions selected from these positions.

In a preferred embodiment, the IA protein of the invention has a sequence that differs from a wild-type human insulin protein in at least one amino acid position selected from positions A3, A7, B2, B4, B7, and B11.

Preferred amino acid substitutions for each position are as follows: Position A3: Ile and Ala; position A7: Ala and Ser; position B2: Thr, Asp, Asn, Glu, Gln, Lys, and Arg; position B4: Phe, Tyr, Glu, Lys, and Arg; position B7: Ala, Ser, Asp, Asn, Tyr and Hsp; and position B11: Ile.

In one aspect of this embodiment, the IA protein comprises the amino acid sequence shown in FIG. 3B. This sequence shows 4 mutation (8% divergence from the wild type insulin sequence) and comprises A7-S, B2-E, B4-Y, and B7-Y.

In another aspect of this embodiment, the IA protein comprises the amino acid sequence shown in FIG. 3C. This sequence shows 2 mutation (8% divergence from the wild type insulin sequence) and comprises A7-S, and B7-D.

In a preferred aspect of this embodiment, the IA protein comprises the amino acid sequence shown in FIG. 3D. This sequence shows 4 mutation (8% divergence from the wild type insulin sequence) and comprises A7-S, B2-T, B4-Y, and B7-Y.

In another aspect of this embodiment, the IA protein comprises the amino acid sequence shown in FIG. 3E. This sequence shows 3 mutation (6% divergence from the wild type insulin sequence) and comprises A7-S, B4-Y, and B7-Y.

In one aspect of this embodiment, the IA protein comprises the amino acid sequence shown in FIG. 3F. This sequence shows 2 mutation (4% divergence from the wild type insulin sequence) and comprises A7-S, B7-E.

In another preferred aspect of this embodiment, the IA protein comprises the amino acid sequence shown In FIG. 3G. This sequence shows 2 mutation and 4deletions at positions B1 to B4 (12% divergence from the wild type insulin sequence) and comprises A7-E and B7-E.

Insulin oligomerizes to dimers, tetramers and hexamers. The hexamers are biologically inactive, however, they stabilize the monomeric compounds, particularly in pharmaceutical compositions, wherein insulin forms a hexamer which is complexed with zinc ions and bound phenolic preservatives. Upon administration into the bloodstream it is believed that the (active) monomer dissociates from the hexamer complex. In some applications it may be desired to occlude phenolic preservatives from the hexamer complex, but still retain the capability to form hexamers. These IA protein complexes find use as slow-acting insulins in contrast to formulations which favor the monomeric state.

Thus, in one preferred embodiment, PDA design is used to generate IA proteins that promote hexamer formation, but occlude phenol binding. In one aspect of this embodiment, IA proteins are generated that are stable and form hexamers in the absence of phenolic preservatives. Some of these IA proteins may form hexamers that are more stable than the human insulin bound to a phenolic compound. In this embodiment, the PDB entry 1wav was chosen. For the PDA calculation, the entire insulin hexamer complex, consisting of 6 A-chains (chains 1, 3, 5, 7, 9, and 11 in hexamer) and 6 B-chains (chains 2, 4, 6, 8, 10, and 12 in the hexamer) was used.

In one embodiment, the following residues were considered in the PDA calculation: Leu-B17 (chain 6), Val-B2 (chain 8), His-B5 (chain 5), Leu-B6 (chain 8), Leu-A16 (chain 11), Leu-B11 (chain 12), and Ala-B14 (chain 12). Accordingly, in a preferred embodiment, IA proteins have variable positions selected from these positions.

In a preferred embodiment, the IA protein of the invention has a sequence that differs from a wild-type human insulin protein in at least one amino acid position selected from positions B17, B2, B5, B6, A16, B11, and B14.

Preferred amino acid substitutions for each position are as follows: Position Leu-B17 (chain 6): Val and Glu; , position Val-B2 (chain 8): Phe and Glu; position His-B5 (chain 5): Phe, Trp, and Leu; position Leu-A16 (chain 11): Phe and Tyr, position Leu-B11 (chain 12): Ile; and position Ala-B14 (chain 12):Trp, Phe, and Leu. The preferred amino acid at position Leu-B6 (chain 8) is Leu (wild type). Thus, preferred substitutions occur at positions B14 and B5.

In a further embodiment, the B14 and B5 positions were analyzed with respect to possible substitutions that promote hexamer formation.

In a preferred embodiment, the IA protein comprises a substitution at amino acid residue B14.

In one aspect of this embodiment, the IA protein comprises the amino acid sequence shown in FIG. 4C. This sequence shows only 1 mutation (2% divergence from the wild type insulin sequence) and comprises B14-F. This IA protein does not bind efficiently a phenol preservative, however, it still forms a hexamer.

In another aspect of this embodiment, the IA protein comprises the amino acid sequence shown in FIG. 4D. This sequence shows only 1 mutation (2% divergence from the wild type insulin sequence) and comprises B14-W. This IA protein does not bind efficiently a phenol preservative, however, it still forms a hexamer.

In another aspect of this embodiment, the IA protein comprises the amino acid sequence shown in FIG. 4F. This sequence shows only 1 mutation (2% divergence from the wild type insulin sequence) and comprises B14-Y. This IA protein does not bind efficiently a phenol preservative, however, it still forms a hexamer.

In another aspect of this embodiment, the IA protein comprises the amino acid sequence shown in FIG. 4G. This sequence shows only 1 mutation (2% divergence from the wild type insulin sequence) and comprises B14-I. This IA protein does not bind efficiently a phenol preservative, however, it still forms a hexamer.

In a another preferred embodiment, the IA protein comprises a substitution at amino acid residue B5.

In one aspect of this embodiment, the IA protein comprises the amino acid sequence shown in FIG. 4B. This sequence shows only 1 mutation (2% divergence from the wild type insulin sequence) and comprises B5-F. This IA protein does not bind efficiently a phenol preservative, however, it still forms a hexamer.

In another preferred embodiment, the IA protein comprises substitutions at amino acid residues B5 and B14.

In one aspect of this embodiment, the IA protein comprises the amino acid sequence shown in FIG. 4A. This sequence shows 2 mutations (42% divergence from the wild type insulin sequence) and comprises B5-F and B14-F. This IA protein does not bind efficiently a phenol preservative, however, it still forms a hexamer.

In another aspect of this embodiment, the IA protein comprises the amino acid sequence shown in FIG. 4E. This sequence shows 2 mutations (42% divergence from the wild type insulin sequence) and comprises B5-F and B14-W. This IA protein does not bind efficiently a phenol preservative, however, it still forms a hexamer.

In a preferred embodiment, the IA proteins of the invention are human insulin conformers. By "conformer" herein is meant a protein that has a protein backbone 3D structure that is virtually the same but has significant differences In the amino acid side chains. That is, the IA proteins of the invention define a conformer set, wherein all of the proteins of the set share a backbone structure and yet have sequences that differ by at least 35%. The three dimensional backbone structure of an IA protein thus substantially corresponds to the three dimensional backbone structure of human insulin "Backbone" in this context means the non-side chain atoms: the nitrogen, carbonyl carbon and oxygen, and the α-carbon, and the hydrogens attached to the nitrogen and α-carbon. To be considered a conformer, a protein must have backbone atoms that are no more than 2 Å from the human insulin structure, with no more than 1.5 Å being preferred, and no more than 1 Å being particularly preferred. In general, these distances may be determined in two ways. In one embodiment, each potential conformer is crystallized and its three dimensional structure determined. Alternatively, as the former is quite tedious, the sequence of each potential conformer is run in the PDA program to determine whether it is a conformer by examining the energy of the sequence.

IA proteins may also be identified as being encoded by IA nucleic acids. In the case of the nucleic acid, the overall homology of the nucleic acid sequence is commensurate with amino acid homology but takes into account the degeneracy In the genetic code and codon bias of different organisms. Accordingly, the nucleic acid sequence homology may be either lower or higher than that of the protein sequence, with lower homology being preferred.

In a preferred embodiment, an IA nucleic acid encodes an IA protein. As will be appreciated by those in the art, due to the degeneracy of the genetic code, an extremely large number of nucleic acids may be made, all of which encode the IA proteins of the present invention. Thus, having identified a particular amino acid sequence, those skilled in the art could make any number of different nucleic acids, by simply modifying the sequence of one or more codons in a way which does not change the amino acid sequence of the IA protein.

In one embodiment, the nucleic acid homology is determined through hybridization studies. Thus, for example, a nucleic acid, which hybridize under high stringency to a nucleic acid sequence encoding insulin (e.g. see GenBank accession numbers J00265 M10039) and encode an IA protein is considered an IA gene.

High stringency conditions are known In the art; see for example Sambrook et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found In Tijssen, Techniques In Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium Ion, typically about 0.01 to 1.0 M sodium Ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known In the art; see Sambrook et al., supra; Ausubel et al., supra, and Tijssen, supra.

The IA proteins and nucleic acids of the present invention are recombinant. As used herein, "nucleic acid" may refer to either DNA or RNA, or molecules which contain both deoxy- and ribonuclotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"). By the term "recombinant nucleic acid" herein is meant nucleic acid, originally formed in vitro, in general, by the manipulation of nucleic acid by endonucleases, in a form not normally found in nature. Thus an isolated IA nucleic acid, in a linear form, or an expression vector formed in vitro by ligating DNA molecules that are not normally joined, are both considered recombinant for the purposes of this invention. It is understood that once a recombinant nucleic acid is made and reintroduced Into a host cell or organism, it will replicate non-recombinantly, i.e. using the In vivo cellular machinery of the host cell rather than in vitro manipulations, however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an IA protein from one organism in a different organism or host cell. Alternatively, the protein may be made at a significantly higher concentration than is normally seen, through the use of an inducible promoter or high expression promoter, such that the protein is made at increased concentration levels. Furthermore, all of the IA proteins outlined herein are in a form not normally found in nature, as they contain amino acid substitutions, insertions and deletions, with substitutions being preferred, as discussed below.

Also included within the definition of IA proteins of the present invention are amino acid sequence variants of the IA protein sequences outlined herein and shown in the Figures. That is, the IA proteins may contain additional variable positions as compared to human insulin. These variants fall into one or more of three classes: substitutional, insertional or deletional variants. These variants ordinarily are prepared by site specific mutagenesis of nucleotides in the DNA encoding an IA protein, using cassette or PCR mutagenesis or other techniques well known in the art, to produce DNA encoding the variant, and thereafter expressing the DNA in recombinant cell culture as outlined above. However, variant IA protein fragments having up to about 100–150 residues may be prepared by in vitro synthesis using established techniques. Specifically, IA proteins comprising only amino acid sequences for the A-chain may be prepared by in vitro synthesis. Similarly, IA proteins comprising only amino acid sequences for the B-chain may be prepared by in vitro synthesis. The individually prepared IA protein A-chain and IA protein B-chain can be combined after synthesis to form the mature IA protein. Techniques for the synthesis of insulin A-chains and B-chains and subsequent formation of mature insulin, i.e., the insulin comprising an A-chain and a B-chain appropriately linked via the disulfide bonds described herein, are known in the art. The same techniques apply to the formation of mature IA proteins starting out with individual IA A-chains and IA B-chains. Amino acid sequence variants are characterized by the predetermined nature of the variation, a feature that sets them apart from naturally occurring allelic or interspecies variation of the IA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed IA variants screened for the optimal combination of desired activity. Techniques for making substitution mutations at predetermined sites in DNA having a known sequence are well known, for example, M13 primer mutagenesis and PCR mutagenesis. Screening of the mutants is done using assays of IA protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances, When small alterations in the characteristics of the IA protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the original IA protein, although variants also are selected to modify the characteristics of the IA proteins as needed. Alternatively, the variant may be designed such that the biological activity of the IA protein is altered. For example, glycosylation sites may be altered or removed. Similarly, the biological function may be altered; for example, in some instances it may be desirable to have more or less potent insulin activity.

The IA proteins and nucleic acids of the invention can be made in a number of ways. Individual nucleic acids and proteins can be made as known in the art and outlined below. Alternatively, libraries of IA proteins can be made for testing.

In a preferred embodiment, sets or libraries of IA proteins are generated from a probability distribution table. As outlined herein, there are a variety of methods of generating a probability distribution table, including using PDA, sequence alignments, forcefield calculations such as SCMF calculations, etc. In addition, the probability distribution can be used to generate information entropy scores for each position, as a measure of the mutational frequency observed in the library.

In this embodiment, the frequency of each amino acid residue at each variable position in the list is Identified. Frequencies can be thresholded, wherein any variant frequency lower than a cutoff is set to zero. This cutoff is preferably 1%, 2%, 5%, 10% or 20%, with 10% being particularly preferred. These frequencies are then built into the IA protein library. That is, as above, these variable positions are collected and all possible combinations are generated, but the amino acid residues that "fill" the library are utilized on a frequency basis. Thus, in a non-frequency based library, a variable position that has possible residues will have 20% of the proteins comprising that variable position with the first possible residue, 20% with the second, etc. However, in a frequency based library, a variable position that has 5 possible residues with frequencies of 10%, 15%, 25%, 30% and 20%, respectively, will have 10% of the proteins comprising that variable position with the first possible residue, 15% of the proteins with the second residue, 25% with the third, etc. As will be appreciated by those in the art, the actual frequency may depend on the method used to actually generate the proteins; for example, exact frequencies may be possible when the proteins are synthesized. However, when the frequency-based primer system outlined below is used, the actual frequencies at each position will vary, as outlined below.

As will be appreciated by those in the art and outlined herein, probability distribution tables can be generated in a variety of ways. In addition to the methods outlined herein, self-consistent mean field (SCMF) methods can be used in the direct generation of probability tables. SCMF is a deterministic computational method that uses a mean field description of rotamer interactions to calculate energies. A probability table generated in this way can be used to create libraries as described herein. SCMF can be used in three ways: the frequencies of amino acids and rotamers for each amino acid are listed at each position; the probabilities are determined directly from SCMF (see Delarue et la. Pac. Symp. Biocomput. 109–21 (1997), expressly incorporated by reference). In addition, highly variable positions and non-variable positions can be identified. Alternatively, another method is used to determine what sequence is jumped to during a search of sequence space; SCMF is used to obtain an accurate energy for that sequence; this energy is then used to rank it and create a rank-ordered fist of sequences (similar to a Monte Carlo sequence list). A probability table showing the frequencies of amino acids at each position can then be calculated from this list (Koehl et al., J. Mol. Biol. 239:249 (1994); Koehl et al., Nat. Struc. Biol. 2:163 (1995); Koehl et al., Curr. Opin. Struct. Biol. 6:222 (1996); Koehl et al., J. Mol. Bio. 293:1183 (1999); Koehl et al., J. Mol. Biol. 293:1161 (1999); Lee J. Mol. Biol. 236:918 (1994); and Vasquez Biopolymers 36:53–70 (1995); all of which are expressly incorporated by reference. Similar methods include, but are not limited to, OPLS-AA (Jorgensen, et al., J. Am. Chem. Soc. (1996), v 118, pp 11225–11236; Jorgensen, W. L.; BOSS, Version 4.1; Yale University: New Haven, Conn. (1999)); OPLS (Jorgensen, et al., J. Am. Chem. Soc. (1988), v 110, pp 1657ff; Jorgensen, et al., J Am. Chem. Soc. (1990), v 112, pp 4768ff); UNRES (United Residue Forcefield; Liwo, at al., Protein Science (1993), v 2, pp1697–1714; Liwo, et al., Protein Science (1993), v 2, pp1715–1731; Liwo, et al., J. Comp. Chem. (1997), v 18, pp849–873; Liwo, et al., J. Comp. Chem. (1997), v 18, pp874–884; Liwo, et al., J. Comp. Chem (1998), v 19, pp259–276; Forcefield for Protein Structure Prediction (Liwo, et al., Proc. Natl. Acad. Sci. USA (1999), v 96, pp5482–5485); ECEPP/3 (Liwo et al., J Protein Chem 1994 May;13(4):375–80); AMBER 1.1 force field (Weiner, et al., J. Am. Chem. Soc. v106, pp765–784); AMBER 3.0 force field (U.C. Singh et al., Proc. Natl. Acad. Sci. USA. 82:755–759); CHARMM and CHARMM22 (Brooks, et al., J. Comp. Chem. v4, pp 187–217); cvff3.0 (Dauber-Osguthorpe, et al.,(1988) Proteins: Structure, Function and Genetics, v4 pp31–47); cff91 (Maple, et al., J. Comp. Chem. v15, 162–182); also, the DISCOVER (cvff and cff91) and AMBER forcefields are used in the INSIGHT molecular modeling package (Biosym/MSI, San Diego Calif.) and HARMM is used in the QUANTA molecular modeling package (Biosym/MSI, San Diego Calif.).

In addition, as outlined herein, a preferred method of generating a probability distribution table is through the use of sequence alignment programs. In addition, the probability table can be obtained by a combination of sequence alignments and computational approaches. For example, one can acid amino acids found in the alignment of homologous sequences to the result of the computation. Preferable one can acid the wild type amino acid identity to the probability table if it is not found in the computation.

As will be appreciated, an IA protein library created by recombining variable positions and/or residues at the variable position may not be in a rank-ordered list. In some embodiments, the entire list may just be made and tested. Alternatively, in a preferred embodiment, the IA protein library is also in the form of a rank ordered list. This may be done for several reasons, including the size of the library is still too big to generate experimentally, or for predictive purposes. This may be done in several ways. In one embodiment, the library is ranked using the scoring functions of PDA to rank the library members. Alternatively, statistical methods could be used. For example, the library may be ranked by frequency score; that is, proteins containing the most of high frequency residues could be ranked higher, etc. This may be done by adding or multiplying the frequency at each variable position to generate a numerical score. Similarly, the library different positions could be weighted and then the proteins scored; for example, those containing certain residues could be arbitrarily ranked.

In a preferred embodiment, the different protein members of the IA protein library may be chemically synthesized. This is particularly useful when the designed proteins are short, preferably less than 150 amino acids in length, with less than 100 amino acids being preferred, and less than 50 amino acids being particularly preferred, although as is known in the art, longer proteins can be made chemically or enzymatically. See for example Wilken et al, Curr. Opin. Biotechnol. 9:412–26 (1998), hereby expressly incorporated by reference.

In a preferred embodiment, particularly for longer proteins or proteins for which large samples are desired, the library sequences are used to create nucleic acids such as DNA which encode the member sequences and which can then be cloned into host cells, expressed and assayed, if desired. Thus, nucleic acids, and particularly DNA, can be made which encodes each member protein sequence. This is done using well known procedures. The choice of codons, suitable expression vectors and suitable host cells will vary depending on a number of factors, and can be easily optimized as needed.

In a preferred embodiment, multiple PCR reactions with pooled oligonucleotides is done, as is generally depicted in FIG. 6. In this embodiment overlapping oligonucleotides are synthesized which correspond to the full length gene. Again, these oligonucleotides may represent all of the different amino acids at each variant position or subsets.

In a preferred embodiment, these oligonucleotides are pooled in equal proportions and multiple PCR reactions are performed to create full length sequences containing the combinations of mutations defined by the library. In addition, this may be done using error-prone PCR methods.

In a preferred embodiment, the different oligonucleotides are added in relative amounts corresponding to the probability distribution table. The multiple PCR reactions thus result in full length sequences with the desired combinations of mutations in the desired proportions.

The total number of oligonucleotides needed is a function of the number of positions being mutated and the number of mutations being considered at these positions: (number of oligos for constant positions)+M1+M2+M3+ . . . Mn=(total number of oligos required), where Mn is the number of mutations considered at position n in the sequence.

In a preferred embodiment, each overlapping oligonucleotide comprises only one position to be varied; in alternate embodiments, the variant positions are too close together to allow this and multiple variants per oligonucleotide are used to allow complete recombination of all the possibilities. That is, each oligo can contain the codon for a single position being mutated, or for more than one position being mutated. The multiple positions being mutated must be close in sequence to prevent the oligo length from being impractical. For multiple mutating positions on an oligonucleotide, particular combinations of mutations can be included or excluded in the library by including or excluding the oligonucleotide encoding that combination. For example, as discussed herein, there may be correlations between variable regions; that is, when position X is a certain residue, position Y must (or must not) be a particular residue. These sets of variable positions are sometimes referred to herein as a "cluster". When the clusters are comprised of residues close together, and thus can reside on one oligonucleotide primer, the clusters can be set to the "good" correlations, and eliminate the bad combinations that may decrease the effectiveness of the library. However, if the residues of the cluster are far apart in sequence, and thus will reside on different oligonucleotides for synthesis, it may be desirable to either set the residues to the "good" correlation, or eliminate them as variable residues entirely. In an alternative embodiment, the library may be generated in several steps, so that the cluster mutations only appear together. This procedure, i.e. the procedure of identifying mutation clusters and either placing them on the same oligonucleotides or eliminating them from the library or library generation in several steps preserving clusters, can considerably enrich the experimental library with properly folded protein. Identification of clusters can be carried out by a number of ways, e.g. by using known pattern recognition methods, comparisons of frequencies of occurrence of mutations or by using energy analysis of the sequences to be experimentally generated (for example, if the energy of interaction is high, the positions are correlated). These correlations may be positional correlations (e.g. variable positions 1 and 2 always change together or never change together) or sequence correlations (e.g. if there is residue A at position 1, there is always residue B at position 2). See: Pattern discovery in Biomolecular Data: Tools, Techniques, and Applications; edited by Jason T. L. Wang, Bruce A. Shapiro, Dennis Shasha. New York: Oxford University, 1999; Andrews, Harry C. introduction to mathematical techniques in pattern recognition; New York, Wiley-interscience [1972]; Applications of Pattern Recognition; Editor, K. S. Fu. Boca Raton, Fla. CRC Press, 1982; Genetic Algorithms for Pattern Recognition; edited by Sankar K. Pal, Paul P. Wang. Boca Raton: CRC Press, c1996; Pandya, Abhijit S., Pattern recognition with neural networks in C++ /Abhijit S. Pandya, Robert 8. Macy. Boca Raton, Fla.: CRC Press, 1998; Handbook of pattern recognition & computer vision I edited by C. H. Chen, L. F. Pau, P. S. P. Wang. 2nd ed. Singapore; River Edge, N.J.: World Scientific, c1999; Friedman, Introduction to Pattern Recognition: Statistical, Structural, Neural, and Fuzy Logic Approaches; River Edge, N.J.: World Scientific, c1999, Series title: Series in machine perception and artificial intelligence; vol. 32; all of which are expressly incorporated by reference. In addition, programs used to search for consensus motifs can be used as well.

In addition, correlations and shuffling can be fixed or optimized by altering the design of the oligonucleotides; that is, by deciding where the oligonucleotides (primers) start and stop (e.g. where the sequences are "cut"). The start and stop sites of oligos can be set to maximize the number of clusters that appear in single oligonucleotides, thereby enriching the library with higher scoring sequences. Different oligonucleotide start and stop site options can be computationally modeled and ranked according to number of clusters that are represented on single oligos, or the percentage of the resulting sequences consistent with the predicted library of sequences.

The total number of oligonucleotides required increases when multiple mutable positions are encoded by a single oligonucleotide. The annealed regions are the ones that remain constant, i.e. have the sequence of the reference sequence.

Oligonucleotides with insertions or deletions of codons can be used to create a library expressing different length proteins. In particular computational sequence screening for Insertions or deletions can result in secondary libraries defining different length proteins, which can be expressed by a library of pooled oligonucleotide of different lengths.

In a preferred embodiment, the IA protein library is done by shuffling the family (e.g. a set of variants); that is, some set of the top sequences (if a rank-ordered list is used) can be shuffled, either with or without error-prone PCR. "Shuffling" in this context means a recombination of related sequences, generally in a random way. It can include "shuffling" as defined and exemplified in U.S. Pat. Nos. 5,830,721; 5,811,238; 5,605,793; 5,837,458 and PCT US/19256, all of which are expressly incorporated by reference in their entirety. This set of sequences can also be an artificial set; for example, from a probability table (for example generated using SCMF) or a Monte Carlo set Similarly, the "family" can be the top 10 and the bottom 10 sequences, the top 100 sequence, etc. This may also be done using error-prone PCR.

Thus, in a preferred embodiment, in silco shuffling is done using the computational methods described herein. That is, starting with either two libraries or two sequences, random recombinations of the sequences can be generated end evaluated.

In a preferred embodiment, error-prone PCR is done to generate the IA protein library. See U.S. Pat. Nos. 5,605,793, 5,811,238, and 5,830,721, all of which are hereby incorporated by reference. This can be done on the optimal sequence or on top members of the library, or some other artificial set or family. In this embodiment, the gene for the optimal sequence found in the computational screen of the primary library can be synthesized. Error prone PCR is then performed on the optimal sequence gene in the presence of oligonucleotides that code for the mutations at the variant positions of the library (bias oligonucleotides). The addition of the oligonucleotides will create a bias favoring the incorporation of the mutations in the library. Alternatively, only oligonucleotides for certain mutations may be used to bias the library.

In a preferred embodiment, gene shuffling with error prone PCR can be performed on the gene for the optimal sequence, in the presence of bias oligonucleotides, to create a DNA sequence library that reflects the proportion of the mutations found in the IA protein library. The choice of the bias oligonucleotides can be done in a variety of ways; they can be chosen on the basis of their frequency, i.e. oligonucleotides encoding high mutational frequency positions can be used; alternatively, oligonucleotides containing the most variable positions can be used, such that the diversity is increased; if the secondary library is ranked, some number of top scoring positions can be used to generate bias oligonucleotides; random positions may be chosen; a few top scoring and a few low scoring ones may be chosen; etc. What is important is to generate new sequences based on preferred variable positions and sequences.

In a preferred embodiment, PCR using a wild type gene or other gene can be used, as is schematically depicted in FIG. 7. In this embodiment, a starting gene is used; generally, although this is not required, the gene is usually the wild type gene. In some cases it may be the gene encoding the global optimized sequence, or any other sequence of the list, or a consensus sequence obtained e.g. from aligning homologous sequences from different organisms. In this embodiment, oligonucleotides are used that correspond to the variant positions and contain the different amino acids of the library. PCR is done using PCR primers at the termini, as is known in the art. This provides two benefits; the first is that this generally requires fewer oligonucleotides and can result in fewer errors. In addition, it has experimental advantages in that if the wild type gene is used, it need not be synthesized.

In addition, there are several other techniques that can be used, as exemplified in the figures, e.g. FIGS. 8–10. In a preferred embodiment, ligation of PCR products is done.

In a preferred embodiment, a variety of additional steps may be done to the IA protein library; for example, further computational processing can occur, different IA protein libraries can be recombined, or cutoffs from different libraries can be combined. In a preferred embodiment, an IA protein library may be computationally remanipulated to form an additional IA protein library (sometimes referred to herein as "tertiary libraries"). For example, any of the IA protein library sequences may be chosen for a second round of PDA, by freezing or fixing some or all of the changed positions in the first library. Alternatively, only changes seen in the last probability distribution table are allowed. Alternatively, the stringency of the probability table may be altered, either by increasing or decreasing the cutoff for inclusion. Similarly, the IA protein library may be recombined experimentally after the first round; for example, the best gene/genes from the first screen may be taken and gene assembly redone (using techniques outlined below, multiple PCR, error prone PCR, shuffling, etc.). Alternatively, the fragments from one or more good gene(s) to change probabilities at some positions. This biases the search to an area of sequence space found in the first round of computational and experimental screening.

In a preferred embodiment, a tertiary library can be generated from combining different IA protein libraries. For example, a probability distribution table from a first IA protein library can be generated and recombined, either computationally or experimentally, as outlined herein. A PDA IA protein library may be combined with a sequence alignment IA protein library, and either recombined (again, computationally or experimentally) or just the cutoffs from each joined to make a new tertiary library. The top sequences from several libraries can be recombined. Sequences from the top of a library can be combined with sequences from the bottom of the library to more broadly sample sequence space, or only sequences distant from the top of the library can be combined. IA protein libraries that analyzed different parts of a protein can be combined to a tertiary library that treats the combined parts of the protein.

In a preferred embodiment, a tertiary library can be generated using correlations in an IA protein library. That is, a residue at a first variable position may be correlated to a residue at second variable position (or correlated to residues at additional positions as well). For example, two variable positions may sterically or electrostatically interact, such that if the first residue is X, the second residue must be Y. This may be either a positive or negative correlation.

Using the nucleic acids of the present invention which encode an IA protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the IA protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or, secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

In a preferred embodiment, when the endogenous secretory sequence leads to a low level of secretion of the naturally occurring protein or of the IA protein, a replacement of the naturally occurring secretory leader sequence is desired. In this embodiment, an unrelated secretory leader sequence is operably linked to an IA protein encoding nucleic acid leading to increased protein secretion. Thus, any secretory leader sequence resulting in enhanced secretion of the IA protein, when compared to the secretion of insulin and its secretory sequence, is desired. Suitable secretory leader sequences that lead to the secretion of a protein are know in the art.

In another preferred embodiment, a secretory leader sequence of a naturally occurring protein or a protein is removed by techniques known in the art and subsequent expression results in intracellular accumulation of the recombinant protein.

Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acd will generally be appropriate to the host cell used to express the fusion protein; for example, transcriptional and translational regulatory nucleic acid sequences from Bacillus are preferably used to express the fusion protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in cells, particularly mammalian cells, such as the CMV promoter, particularly in combination with a Tet regulatory element.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

In a preferred embodiment, the expression vector comprises the components described above and a gene encoding an IA protein. In this aspect, only one species of an IA protein will be expressed in the cell comprising the expression vector.

In one preferred embodiment, it is desired to express two different IA proteins (variant A and variant B) and thus, two expression vectors, one comprising a gene coding IA protein variant A, the other one comprising a gene coding for IA protein variant B are introduced into the same host cell. This allows formation of a preferred IA protein dimer.

In one aspect of this embodiment, an expression vector is constructed that comprises two IA genes encoding two different IA proteins (variant A and variant B). In one aspect of this embodiment, a polycistronic gene can be constructed as is known in the art for co-expression in a host cell.

As will be appreciated by those in the art, all combinations are possible and accordingly, as used herein, the combination of components, comprised by one or more vectors, which may be retroviral or not, is referred to herein as a "vector composition".

The IA nucleic acids are introduced into the cells either alone or in combination with an expression vector. By "introduced into" or grammatical equivalents herein is meant that the nucleic acids enter the cells in a manner suitable for subsequent expression of the nucleic acid. The method of introduction is largely dictated by the targeted cell type, discussed below. Exemplary methods include $(Ca_3PO_4)_2$ precipitation, liposome fusion, lipofectin®, electroporation, viral infection, etc. The IA nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

The IA proteins of the present invention are produced by culturing a host cell transformed with an expression vector containing nucleic acid encoding an IA protein, under the appropriate conditions to induce or cause expression of the IA protein. The conditions appropriate for IA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, *Pichia Pastoris,* etc.

In a preferred embodiment, the IA proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for the fusion protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei. As outlined herein, a particularly preferred method utilizes retroviral infection, as outlined in PCT US97/01019, incorporated by reference.

As will be appreciated by those in the art, the type of mammalian cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive peptide. As is more fully described below, cell types implicated in a wide variety of disease conditions are particularly useful, so long as a suitable screen may be designed to allow the selection of cells that exhibit an altered phenotype as a consequence of the presence of a peptide within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteociasts, chondrocytes and other connective issue cells, keratinoytes, melanocytes, liver cells, kidney cells, and adipocytes. Particularly preferred cells are pancreatic beta cells or variants thereof. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be additionally genetically engineered, that is, contain exogeneous nucleic acid other than the IA nucleic acid.

In a preferred embodiment, the IA proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of the IA protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the IA protein in bacteria. The signal sequence typically encodes a signal peptide comprised of hydrophobic amino acids which direct the secretion of the protein from the cell, as is well known in the art The protein is either secreted into the growth media (gram-positive bacteria) or into the periplasmic space, located between the inner and outer membrane of the cell gram-negative bacteria). For expression in bacteria, usually bacterial secretory leader sequences, operably linked to an IA protein encoding nucleic acid, are preferred.

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, IA proteins are produced in insect cells. Expression vectors for the transformation of insect cells, and in particular, baculovirus-based expression vectors, are well known in the art.

In a preferred embodiment, IA proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1, 10 promoter, the promoters from alcohol dehydrogenase, enolase, glucolinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In addition, the IA polypeptides of the invention may be further fused to other proteins, if desired, for example to increase expression or stabilize the protein.

In one embodiment, the IA nucleic acids, proteins and antibodies of the invention are labeled with a label other than the scaffold. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Once made, the IA proteins may be covalently modified. One type of covalent modification includes reacting targeted amino acid residues of an IA polypeptide with an organic derivatizing agent that is capable of reacting with selected side chains or the N- or C-terminal residues of an IA polypeptide. Derivatization with bifunctional agents is useful, for instance, for crosslinking an IA protein to a water-insoluble support matrix or surface for use in the method for purifying anti-IA protein antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctonal imidoesters, including disuccimidyl esters such as 3,3-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T.E. Creighton, Proteins: Structure and Molecular Properties, W.H. Freeman & Co., San Francisco, pp. 79–86 (1983)], acetylation of the N-terminal amine, and amidation of any C-terminal carboxyl group.

Another type of covalent modification of the IA polypeptide included within the scope of this invention comprises altering the native glycosylation pattern of the polypeptide. "Altering the native glycosylation pattern" is intended for purposes herein to mean deleting one or more carbohydrate moieties found in native sequence IA polypeptide, and/or adding one or more glycosylation sites that are not present in the native sequence IA polypeptide.

Addition of glycosylation sites to IA polypeptides may be accomplished by altering the amino acid sequence thereof. The alteration may be made, for example, by the addition of, or substitution by, one or more serine or threonine residues to the native sequence IA polypeptide (for O-linked glycosylation sites). The IA protein amino acid sequence may optionally be altered through changes at the DNA level, particularly by mutating the DNA encoding the IA polypeptide at preselected bases such that codons are generated that will translate into the desired amino acids.

Another means of increasing the number of carbohydrate moieties on the IA polypeptide is by chemical or enzymatic coupling of glycosides to the polypeptide. Such methods are described in the art, e.g., in WO 87/05330 published Sep. 11, 1987, and in Aplin and Wriston, CRC Crit. Rev. Biochem., pp. 259–306 (1981).

Removal of carbohydrate moieties present on the IA polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Such derivatized moieties may improve the solubility, absorption, permeability across the blood brain barrier, biological half life, and the like. Such moieties or modifications of IA polypeptides may alternatively eliminate or attenuate any possible undesirable side effect of the protein and the like. Moieties capable of mediating such effects are disclosed, for example, in Remington's Pharmaceutical Sciences, 16th ed., Mack Publishing Co., Easton, Pa. (1980).

Another type of covalent modification of IA proteins comprises linking the IA polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

IA polypeptides of the present invention may also be modified in a way to form chimeric molecules comprising an IA polypeptide fused to another, heterologous polypeptide or amino acid sequence. In one embodiment, such a chimeric molecule comprises a fusion of an IA polypeptide with a tag polypeptide which provides an epitope to which an anti-tag antibody can selectively bind. The epitope tag is generally placed at the amino- or carboxyl-terminus of the IA polypeptide. The presence of such epitope-tagged forms of an IA polypeptide can be detected using an antibody against the tag polypeptide. Also, provision of the epitope tag enables the IA polypeptide to be readily purified by affinity purification using an ant-tag antibody or another type of affinity matrix that binds to the epitope tag. In an alternative embodiment, the chimeric molecule may comprise a fusion of an IA polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag-polypeptide and its antibody 12CA5 [Field et al., Mol. Cell. Biol. 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the *Herpes Simplex* virus glycoprotein D (gD) tag and its antibody [Paborsky et al., Protein Engineering, 3(6):547–553 (1990)]. Other tag polypeptides include the Flag-peptide [Hopp et al., BioTechnology 6:1204–1210 (1988)]; the KT3 epitope peptide [Martin et al., Science 255:192–194 (1992)]; tubulin epitope peptide [Skinner et al., J. Biol. Chem. 266:15163–15166 (1991)]; and the T7 gene 10 protein peptide tag [Lutz-Freyermuth et al., Proc. Natl. Acad. Sci. U.S.A. 87:6393–6397 (1990)].

In a preferred embodiment, the IA protein is purified or isolated after expression. IA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the IA protein may be purified using a standard anti-library antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the IA protein. In some instances no purification will be necessary.

Once made, the IA proteins and nucleic acids of the invention find use in a number of applications. In a preferred embodiment, the IA proteins are administered to a patient to treat aninsulin-associated disorder.

By "insulin associated disorder", "insulin-dependent disorder", "insulin responsive disorder", "condition" or similar grammatical equivalents thereof, herein is meant a disorder that can be ameliorated by the administration of a pharmaceutical composition comprising an insulin or an IA protein, including, but not limited to type I diabetes, type 2 diabetes; hyperglycemia; diabetes mellitus; familial hyperproinsulinemia; disorder of carbohydrate metabolism; disorder of skeletal muscle protein turnover; and disorders associated with any of the above-listed conditions.

In a preferred embodiment, a therapeutically effective dose of an IA protein is administered to a patient in need of treatment. By "therapeutically effective dose" herein is meant a dose that produces the effects for which it is administered. The exact dose will depend on the purpose of the treatment, and will be ascertainable by one skilled in the art using known techniques. As is known in the art, adjustments for IA protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The term "treatment" in the instant invention is meant to include therapeutic treatment, as well as prophylactic, or suppressive measures for the disease or disorder. Thus, for example, in the case of type I diabetes, successful administration of an IA protein prior to onset of the disease results in "treatment" of the disease. As another example, successful administration of an IA protein after clinical manifestation of the disease to combat the symptoms of the disease comprises "treatment" of the disease, "Treatment" also encompasses administration of an IA protein after the appearance of the disease in order to eradicate the disease. Successful administration of an agent after onset and after clinical symptoms have developed, with possible abatement of clinical symptoms and perhaps amelioration of the disease, comprises "treatment" of the disease.

Those "in need of treatment" include mammals, in particular humans, already having the disease or disorder, as well as those prone to having the disease or disorder, including those in which the disease or disorder is to be prevented. Specifically, an "individual at risk" for type I diabetes or diabetes mellitus, herein means (i) an individual having a blood relative with type 1 diabetes or diabetes mellitus; (ii) auto-antibody-positive individuals without overt type 1 diabetes these auto-antibodies include cytoplasmic islet cell auto-antibodies, insulin antibodies and glutamic acid decarboxylase auto-antibodies; (iii) individuals with histocompatibility (HLA) type DR3 or DR4DQWB; (iv) individuals with glucose abnormalities such as a loss of first phase insulin secretion on glucose tolerance tests.

In another embodiment, a therapeutically effective dose of an IA protein, an IA gene, or an IA protein antibody is administered to a patient having a disease involving inappropriate expression of insulin. A "disease involving inappropriate expression of insulin" within the scope of the present invention is meant to include diseases or disorders characterized by an overabundance of insulin. This overabundance may be due to any cause, including, but not limited to, overexpression at the molecular level, prolonged or accumulated appearance at the site of action, or increased activity of insulin relative to normal. Included within this definition are diseases or disorders characterized by a reduction of insulin. This reduction may be due to any cause, including, but not limited to, reduced expression at the molecular level, shortened or reduced appearance at the site of action, or decreased activity of insulin relative to normal.

Such an overabundance or reduction of insulin can be measured relative to normal expression, appearance, or activity of insulin according to, but not limited to, the assays described and referenced herein.

The administration of the IA proteins of the present invention, preferably in the form of a sterile aqueous solution, can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds, inflammation, or multiple sclerosis, the IA protein may be directly applied as a solution or spray. Depending upon the manner of introduction, the pharmaceutical composition may be formulated in a variety of ways. The concentration of the therapeutically active IA protein in the formulation may vary from about 0.1 to 100 weight %. In another preferred embodiment, the concentration of the IA protein is in the range of 1–100 U/ml, with dosages from 0.05, 0.1, 0.2, and 0.5 U/kg of body weight being preferred.

The pharmaceutical compositions of the present invention comprise an IA protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, proplonic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers such as NaOAc; fillers such as microcrystalline cellulose, lactose, corn and other starches; binding agents; sweeteners and other flavoring agents; coloring agents; and polyethylene glycol. Additives are well known in the art, and are used in a variety of formulations.

In addition, in one embodiment, the IA proteins of the present invention are formulated using a process for pharmaceutical compositions of recombinant insulin as described in U.S. Pat. Nos. 5,843,886, 6,034,054, 4,992,417, 5,506,202, 5,559,094, 5,700,662, 5,618,913, 5,514,646, and 5,514,646, which, hereby, are expressly incorporated in its entirety.

In a further embodiment, the IA proteins are added in a micellular formulation; see U.S. Pat. No.5,833,948, hereby expressly incorporated by reference in its entirety.

Combinations of pharmaceutical compositions may be administered. Moreover, the compositions may be administered in combination with other therapeutics.

In one embodiment provided herein, antibodies, including but not limited to monoclonal and polyclonal antibodies, are raised against IA proteins using methods known in the art. In a preferred embodiment, these anti-IA protein antibodies are used for immunotherapy. Thus, methods of immunotherapy are provided. By "immunotherapy" is meant treatment of an IFN-β related disorders with an antibody raised against an IA protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with an IA protein antigen to which antibodies are raised. As appreciated by one of ordinary skill in the art, the IA protein antigen may be provided by injecting an IA polypeptide against which antibodies are desired to be raised into a recipient, or contacting the recipient with an IA protein encoding nucleic acid, capable of expressing the IA protein antigen, under conditions for expression of the IA protein antigen.

In another preferred embodiment, a therapeutic compound is conjugated to an antibody, preferably an anti-IA protein antibody. The therapeutic compound may be a cytotoxic agent in this method, targeting the cytotoxic agent to e.g., pancreatic tumor tissue or cells, results in a reduction in the number of afflicted cells, thereby reducing symptoms associated with cancer, and IA protein related disorders. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, IA proteins are administered as therapeutic agents, and can be formulated as outlined above. Similarly, IA genes (including both the full-length sequence, partial sequences, or regulatory sequences of the IA protein coding regions) can be administered in gene therapy applications, as is known in the art. These IA genes can include antisense applications, either as gene therapy (i.e. for incorporation into the genome) or as antisense compositions, as will be appreciated by those in the art.

In a preferred embodiment, the nucleic acid encoding the IA proteins may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. [Zamecnik et al., Proc. Natl. Acad. Sci. U.S.A. 83:4143–4146 (1986)]. The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of riposomes, electroporation, microinjection, cell fusion, DEAE-dextran, the calcium phosphate precipitation method, etc. The currently preferred in vivo gene transfer techniques include transfection with viral (typically retrovirad) vectors and viral coat protein-liposome mediated transfection [Dzau et al., Trends in Biotechnology 11:205–210 (1993)]. In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem 262:4429–4432 (1987); and Wagner et al., Proc. Natl. Acad. Sci. U.S.A. 87:3410–3414 (1990). For review of gene marking and gene therapy protocols see Anderson et al., Science 256:808–813 (1992).

In a preferred embodiment, IA genes are administered as DNA vaccines, either single genes or combinations of IA genes. Naked DNA vaccines are generally known in the art. Brower, Nature Biotechnology, 16:1304–1305 (1998). Methods for the use of genes as DNA vaccines are well known to one of ordinary skill in the art, and include placing an IA gene or portion of an IA gene under the control of a promoter for expression in a patient in need of treatment. The IA gene used for DNA vaccines can encode full-length IA proteins, but more preferably encodes portions of the IA proteins including peptides derived from the IA protein. In a preferred embodiment a patient is immunized with a DNA vaccine comprising a plurality of nucleotide sequences derived from an IA gene. Similarly, it is possible to immunize a patient with a plurality of IA genes or portions thereof as defined herein. Without being bound by theory, expression of the polypeptide encoded by the DNA vaccine, cytotoxic T-cells, helper T-cells and antibodies are induced which recognize and destroy or eliminate cells expressing IFN-β proteins.

In a preferred embodiment, the DNA vaccines include a gene encoding an adjuvant molecule with the DNA vaccine. Such adjuvant molecules include cytokines that increase the immunogenic response to the IA polypeptide encoded by the DNA vaccine. Additional or alternative adjuvants are known to those of ordinary skill in the art and find use in the invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLE 1

Design and Characterization of Novel IA Proteins by PDA

Summary: Sequences for novel insulin activity proteins (IA proteins) were designed by simultaneously optimizing residues in the burled core of the protein, residues on the surface of the protein and residues at the boundary of the protein using Protein Design Automation (PDA) as described in WO98/47089, U.S. Ser. Nos. 09/058,459, 09/127,926, 60/104,612, 60/158,700, 09/419,351, 60/181,630, 60/186,904, and U.S. patent application, entitled Protein Design Automation For Protein Libraries (Filed: Apr. 14, 2000; Inventor: Bassil Dahiyat), all of which are expressly incorporated by reference in their entirety.

Several core designs (6 positions), boundary designs (15 positions) and surface designs (22 positions) were completed, with 43 residues considered in total, corresponding to $20^{43}$ sequence possibilities. Residues unexposed to solvent were designed in order to minimize changes to the molecular surface and to limit the potential for antigenicity of designed novel protein analogues.

Calculations required from 12–19 hours on 16 Silicon Graphics R10000 CPU's. The global optimum sequence from each design was selected for characterization. From 1–20 residues were changed from human insulin in the designed proteins, out of 51 residues total.

Computational Protocols
Template Structure Preparation:

For this study the crystal structure of human insulin as deposited in the PDB data bank was used [PDB record 1TRZ; Ciszak and Smith, Biochemistry 33(6):1512–7 (1994)]. Ciszak and Smith solved the structure by x-ray crystallography to a resolution of 1.6 Ångstrom. The structure of the T3R3 human insulin hexamer is complexed with two zinc ions. The asymmetric unit consists of a TR trimer and the insulin hexamer is generated by the action of the crystallographic 3-fold axis. The conformation of one Insulin trimer is nearly identical to that of the T6 hexamer, while the other trimer approximates that of the R6 hexamer, except for the three N-terminal B-chain residues that adopt an extended rather than an alpha-helical conformation. Each of the two zinc ions, which lie on the crystallographic 3fold axis and exhibit two different, disordered coordination geometries, is coordinated by the imidazole groups of three symmetry-related B10-His residues. The coordination sphere of the zinc in the T3 trimer is either tetrahedral, with the fourth site filled by a chloride ion, or octahedral, completed by three water molecules. The coordination of the zinc in the 12 Å narrow channel in the R3 trimer is tetrahedral, with either a second chloride ion or a water molecule completing the coordination sphere [Ciszak and Smith, supra).

PDA calculations were performed for the A-chain and B-chain simultaneously. The zinc ions and all water molecules as well as all hydrogen atoms that are present in the PDB file 1TRZ or 1wav were removed from the structure prior to the PDA calculation.
Design Strategies:

Core residues were selected for design since optimization of these positions can improve stability, although stablization has been obtained from modifications at other sites as well. Core designs also minimize changes to the molecular surface and thus limit the designed protein's potential for antigenicity. Other PDA calculations involved core, boundary and surface residues.
PDA Calculations All PDA calculations were preformed with solvation model 2. Solvation model 2 is the solvation model described by Street and Mayo [Fold. Design 3:253–258 (1998)]. If possible, Dead End Elimination (DEE) was run to completion to find the PDA ground state. The hexamer calculations were performed with both salvation 1 and 2, giving similar results.

This was done for the PDA calculations for the A-chain and B-chain of insulin in the designs for (i) disulfide replacement(ii) mutations promoting hexamer formation, and (iii) global redesigns for improved stability. For the 'trz_08' calculation (see below), DEE was aborted after the rotamer sequence space was reduced to less than $10^{25}$ sequences. The DEE calculation was for all the given Core calculation followed by Monte Carlo (MC) minimization and a ist of the 1,000 or up to 10,000 lowest energy sequences was generated.

Before the PDA calculations were started an initial preparation of the structure was performed. For the A-chain and B-chain, all side chains were minimized with Biograf for 50 steps using conjugate gradient procedure without a Coulomb potential this is followed by an additional 50 steps of conjugate gradient minimization without a Coulomb potential for the complete structure of the A-chain using Biograf. This minimization procedure was chosen to remove initial bad contacts in the structure.

The PDA calculations for all the designs were run using the a2h1p0 rotamer library. This library is based on the backbone-dependent rotamer library of Dunbrack and Karplus (Dunbrack and Karplus, J. Mol. Biol. 230(2):543–74 (1993); hereby expressly incorporated by reference) but includes more rotamers for the aromatic and hydrophobic amino acids; $X_1$ and $X_2$ angle values of rotamers for all the aromatic amino acids and $X_1$ angle values for all the other hydrophobic amino acids were expanded ±1 standard deviation about the mean value reported in the Dunbrack and Karplus library. Typical PDA parameters were used: the van der Waals scale factor was set to 0.9, the H-bond potential well-depth was set to 8.0 kcal/mol, the solvation potential was calculated using type 2 solvation with a nonpolar burial energy of 0.048 kca/mol and a nonpolar exposure multiplication factor of 1.6, and the secondary structure scale factor was set to 0.0 (secondary structure propensities were not considered).

Calculations required from 12–24 hours on 16 Silicon Graphics R10000 CPU's.
Monte Carlo Analysis Monte Carlo analysis of the sequences produced by PDA shows the ground state (optimal) amino acid and amino acids allowed for each variable position and their frequencies of occurrence (see Tables 1–4).

EXAMPLE 2

Disulfide Replacement (Design cys1)

This PDA calculation considers potential cysteine knockouts and all positions within dose proximity (5 Å) to these cysteines to allow for flexibility in the structure and to accommodate additional mutations.

By visual inspection, the following residues were identified as belonging to the boundary of the protein:

A5-Gln, A15-Gln, A19-Tyr, B2-Val, B18-Val, and B22-Arg. The following residues were identified as belonging to the core of the protein: A2-Ile, A3Val, A16-Leu, B11-Leu, B15-Leu, and B24-Phe. The following cysteine residues were included in this design: A6, A7, A11, A20, B7, and B19.

Thus, the following positions were included in the PDA design:

| A2 | A3 | A5 | A6 | A7 | A11 | A15 | A16 | A19 | A20 | B2 | B7 | B11 | B15 | B18 | B19 | B22 | B24 |
|---|---|---|---|---|---|---|---|---|---|---|---|---|---|---|---|---|---|
| Ile | Val | Gln | Cys | Cys | Cys | Gln | Leu | Tyr | Cys | Val | Cys | Leu | Leu | Val | Cys | Arg | Phe |

The boundary and cysteine residues were allowed to change to any amino acid, except Cys, Pro, and Gly. Core residues were allowed to change to any PHOBIC amino acid (Ala, Val, Leu, Ile, Phe, Tyr, Trp, Met) and the PDA core solvation potential was used including surface area calculation.

Using Monte Carlo technique a list of low energy sequences was generated. The analysis of the lowest 1000 protein sequences generated by Monte Carlo leads to the mutation pattern are shown in the Table 1: If no probability is shown, a value of 1 was assigned (×1000=1000).

Any combination of amino acid substitutions shown In Table 1 is possible and has a high probability to result in an IA protein that has fewer disulfide bonds than insulin.

Disulfide Replacement (Designs cys77a, cys77b, cys77d, cys77d+, helix24 and cys-4)

PDA design 'cys77', only A7Cys, B7-Cys and all residues within 6 Å of their sulfur atoms (A3,7, B2,4,7,11) were considered in the calculation.

By visual inspection, the following residues were identified as belonging to the boundary of the protein: A7-Cys,

| # | consensus | probabilities (x1000) | | | | | | |
|---|---|---|---|---|---|---|---|---|
| 2 (A2): | LEU 905 | | | | | | | |
| 3 (A3): | ILE 811 | VAL 188 | ILE 811 | | | | | |
| 5 (A5): | ARG 306 | VAL 84 | GLU 218 | GLN 288 | ARG 306 | | | |
| 6 (A6): | ALA 999 | | | | | | | |
| 7 (A7): | SER 765 | ALA 234 | SER 765 | | | | | |
| 11 (A11): | ALA 999 | | | | | | | |
| 15 (A15): | LEU 388 | LEU 388 | GLU 362 | GLN 164 | ARG 52 | | | |
| 16 (A16): | ILE 566 | LEU 383 | ILE 566 | | | | | |
| 19 (A19): | PHE 999 | | | | | | | |
| 20 (A20): | ASP 538 | ALA 119 | SER 332 | ASP 538 | | | | |
| 23 (B2): | GLU 386 | ASP 70 | ASN 71 | GLU 386 | GLN 235 | LYS 117 | ARG 85 | |
| 28 (B7): | TYR 808 | HSP 171 | TYR 808 | | | | | |
| 32 (B11): | LEU 968 | | | | | | | |
| 36 (B15): | LEU 999 | | | | | | | |
| 39 (B18): | VAL 999 | | | | | | | |
| 40 (B19): | ALA 999 | | | | | | | |
| 43 (B22): | GLN 985 | | | | | | | |
| 45 (B24): | PHE 983 | | | | | | | |

Thus, any protein sequence showing mutations at the positions according to Table 1 will potentially generate a more stable and active IA protein. In particular those protein sequences found among the list of the lowest 101 MC generated sequences (data not shown) have a high potential to result in a more stable and active IA protein. A preferred IA sequence derived from the PDA design 'cys1' is shown in FIG. 3A. This sequence shows 20 mutations when compared to the wild type insulin: G-A1-N, I-A2-L, CA6A, C-A7-S, I-A10Q, C-A11-A, L-A16I, E-A17-Y, Y-A19F, CA20-D, F-B1-D, Q-B4-F, CB7-Y, L-B11-I, V-B12-R, A-B14-W, C-B19-A, F-B25N, Y-B26-F, and T-B27-D. Cysteines at positions A6, A11, and B19 all become Ala, indicating a lack of space at these positions.

B2-Val, B4Gln, and B7-Cys. The following residues were identified as belonging to the core of the protein: A3-Val and B11-Leu.

Thus, the following positions were included in the PDA design:

| A3 | A7 | B2 | B4 | B7 | B11 |
|---|---|---|---|---|---|
| Val | Cys | Val | Gln | Cys | Leu |

Using Dead-End Elimination and Monte Carlo technique a list of low energy sequences was generated. The analysis of the lowest 1000 protein sequences generated by Monte Carlo leads to the mutation pattern are shown in the Table 2:

| # | consensus | probabilities (x1000) | | | | | |
|---|---|---|---|---|---|---|---|
| 3(A3) | VAL 751 | ALA 161 | VAL 751 | ILE 80 | | | |
| 7 (A7) | SER 573 | ALA 408 | SER 573 | | | | |
| 23 (B2) | GLN 204 | THR 90 | VAL 54 | ASP 76 | ASN 51 | GLU 185 | |
| | | GLN 204 | LYS 78 | ARG 103 | | | |

-continued

| # | consensus | probabilities (x1000) | | | | | |
|---|---|---|---|---|---|---|---|
| 25 (B4) | TYR 304 | PHE 207 | TYR 304 | GLU 67 | GLN 93 | LYS 62 | ARG 154 |
| 28 (B7) | TYR 467 | ALA 139 | SER 107 | ASP 157 | ASN 52 | HSP 77 | TYR 467 |
| 32 (B11) | LEU 756 | LEU 756 | ILE 239 | | | | |

Thus, any protein sequence showing mutations at the positions according to Table 2 will potentially generate a more stable and active IA protein. In particular those protein sequences found among the list of the lowest 101 MC generated sequences (data not shown) have a high potential to result in a more stable and active IA protein. A preferred IA sequence derived from the PDA design 'cys77a' is shown in FIG. 3B. This sequence shows 4 mutations when compared to the wild type insulin: CA7-S, V-B2-E, OB4-Y, and C-B7-Y.

PDA design 'cys77b' is similar to PDA design 'cys77a', however, in this calculation only positions A7 and B7 were allowed to change to other residues. The other positions had their amino acid identities fixed, but were allowed to change conformation. 'Cys77b' was a design of only A7–B7, the reduced conformational freedom blocked the Tyr mutation from BT. A preferred sequence from this design is shown in FIG. 3C. This sequence shows 2 mutations, C-A7-S and C-B7-D.

PDA designs 'cys77d' and 'cys77d+' are the minimal sets of mutations that allow the A7 Ser. B7 Tyr pair to occur. Preferred sequences from these two designs are shown in FIGS. 3D and 3E.

The sequence shown in FIG. 3D shows 4 mutations, C-A7-S , V-B2-T, Q-B4-Y, and C-B7-Y.

The sequence shown in FIG. 3E shows 3 mutations, C-A7-S , Q-B4-Y, and C-B7-Y.

PDA design 'helix 24' is same as PDA design 'cys77a' except that the backbone of B-chain residues 1–5 were set to helical $\phi$, $\psi$ of $-57°$ and $50°$, respectively. This is an idealized R state with more room.

A preferred sequence obtained from this design is shown in FIG. 3F. This sequence shows 2 mutations, C-A7-S and C-B7-E.

PDA design 'cys-4' included deletion of residues B1–B4 and calculations for positions A3, A7, B3, and B7.

A preferred sequence obtained from this design is shown in FIG. 3G. This sequence shows 2 substitutions, CA7-E and CB7-E and deletions of residues at positions B1 to B4. This IA protein generates more room for A7-B7.

Other preferred mutations for the A-chain are as follows: 1Ala, 2Leu, 6Ala, 7Ser, 7Ala, 7Glu, 7Asn, 10Gin, 11Ala, 16Ile, 17Tyr, 19Phe, 20Asp, 20Ser, and 20Ala.

Other preferred mutations for the B-chain are as follows: 1Asp, 2Glu, 2Thr, 4Tyr, 4Phe, 7Tyr, 7His, 7Asp, 7Ala, 7Ser, 7Glu, 11Ile, 12Arg, 14Trp, 19Ala, 25Asn, 26Phe, and 27Asp.

Any combination of amino acid substitutions shown in Table 2 is possible and should result in a more stable IA protein.

Generally, the steric constraints in the insulin dimer make the disulfide positions difficult to model for side chain substitution without perturbing the backbone significantly. A6–A11 was very sterically constrained as was A20–B19. The disulfide A7–B7was an exception, and was replaced with a Ser-Tyr, or Ser-Glu/Asp as shown above for various calculations.

EXAMPLE 3

Insulin Variants that Promote Hexamer Formation: B14 Substitutions

In preliminary calculations, position 14 on the B chain optimized to become a large hydrophobic residue, despite its location near the surface of the protein. In the R6 hexamer this position is mostly buried, and is in contact with the phenol molecule that stabilizes the R-form of the hexamer. In an effort to occlude the phenol binding site of the hexameric R6 conformation of human insulin (PDB 1wav; Ding et al. Sci. China C. Life Sci. 39(2):144–53 (1996); hereby expressly incorporated as reference), or to mimic the allosteric effect of phenol binding, redesigns on the residues (from different subunits) surrounding one of the phenol binding sites (in the absence of phenol) were made. Predicted structures of these mutants fill the space occupied by the phenol in the hexamer, and mimic the structural placement of the phenol and its chemical identity. By occluding the phenol binding site, phenol binding will be prevented and the link between phenol binding and R state formation will be broken.

All of the PDA 'wav14' design sequences and hexamer sequences were derived from calculations that were done on the entire insulin hexamer complex (PDB file 1wav; Ding et al., supra) which contains 6 sets of insulin heterodimers (chains 1 through 12). As ingle phenol binding site centered on the chain 12, Ala-B14 (the 6th insulin heterodimer in the complex, B-chain) was designed. The following positions were involved:

where the first number is the PDA renumbering of residues and the second number is the chain number in the hexamer, the core and boundary residues are specified last:

| | | | |
|---|---|---|---|
| 140 | #6 | LeuB17 | boundary |
| 176 | #8 | ValB2 | boundary |
| 179 | #8 | HisB5 | boundary |
| 180 | #8 | LeuB6 | boundary |
| 271 | #11 | LeuA16 | core |
| 287 | #12 | LeuB11 | core |
| 290 | #12 | AlaB14 | boundary |

These positions were chosen because they are within 4.6 Å from the B14 side chain. 71

Using DEE and Monte Carlo technique a list of low energy sequences was generated. The analysis of the lowest 1000 protein sequences generated by Monte Carlo leads to the mutation pattern are shown in the Table 3:

| res# | | | consensus | probabilities (× 1000) |
|---|---|---|---|---|
| 140 | #6 | LeuB17 | Leu 350 | Val 184, Leu 597, Glu 218 |
| 176 | #8 | ValB2 | Val 587 | Val 684, Phe 183, Glu 133 |
| 179 | #8 | HisB5 | Phe 490 | Leu 205, Phe 597, Trp 199 |

| res# | | consensus | | probabilities (× 1000) |
|---|---|---|---|---|
| 180 | #8 | LeuB6 | Leu 767 | Leu 1000 |
| 271 | #11 | LeuA16 | Phe 667 | Leu 108, Phe 713, Tyr 179 |
| 287 | #12 | LeuB11 | Ile 514 | Leu 449, Ile 551 |
| 290 | #12 | AlaB14 | Trp 469 | Leu 157, Phe 228, Trp 615 |

Preferred IA sequences obtained from this PDA calculation and comprising only B14substitutions are shown in FIGS. 4C, 4D. 4F, and 4G.

Further, substitutions B14Trp or B14Phe will prevent formation of the T state formed by the monomer in solution, further driving the equilibrium to the R state. This will promote self-association of insulin, since the R state is not stable as a monomer.

Other substitutions at B14 with similar effects are B14Tyr (FIG. 4F) and B14 Ile (FIG. 4G). These mutations may require further mutations as described further below for B5 substitutions.

Insulin Variants that Promote Hexamer Formation: B5 Substitutions

In this PDA design the B5 position of the B-chain was analyzed with respect to possible substitutions that promote insulin hexamer formation.

Substitutions of HisB5 to Trp or Phe is expected to have the same occlusion of the phenol binding site in hexameric insulin as a mutation of B14 to Trp or Phe. These B5 substitutions should destabilize the monomeric form of insulin (relative to the unfolded monomer) because the side chain of B5 is solvent exposed in the monomer and should stabilize the R6 form of the hexamer (relative to the wild type form of the R6 hexamerin the absence of phenol because it has formed a close interaction with other nonpolar side chains from other subunits which surround the phenol binding site, similar to the interactions normally made by phenol.

Unlike the B14 mutations, the presence of Trp and Phe at B5 is sterically compatible with a T state. A preferred IA protein sequence comprising a B5 substitution only is shown in FIG. 4B.

Insulin Variants that Promote Hexamer Formation: B14/B5 Double Substitutions In this PDA design the B5 and B14 positions of the B-chain were analyzed with respect to possible substitutions that promote insulin hexamer formation. The following substitutions were found: B-chain, position 14: Phe, Trp, Tyr, or Ile; and B-chain, position 5: Phe or Trp.

Any combination of the above substitutions is possible, such as B14-Phe/B5-Phe, B14-Phe/B5Trp, B14-Trp/B5-Phe, B14Trp/B5-Trp, B14Tyr/B5Phe, B14-Tyr/B5Trp, B14Ile/B5-Phe, and B14-Ile/B5-Trp. Preferred IA sequences comprising B5 and B14 substitutions are shown in FIG. 4A and in FIG. 4E.

Insulin Variants that Promote Hexamer Formation: Summary

The results suggest that His-B5-Phe and/or Ala-B14-Phe should occlude the phenol binding site and prevent binding of phenol-like molecules at these sites in the hexamer. B14-Phe should be more effective at preventing phenol binding simply for steric reasons. Either mutation can be made singly, or they can be made as a double mutant, which should be even more effective at occluding the phenol binding site.

B5-Phe is completely compatible with the T-form of the monomer, but B14-Phe (and the double mutant containing B14-Phe) should be sterically unable to form the standard T-state, in either the monomer or the hexamer, due to steric clashes with atoms from the first several residues of the B-chain, particularly B6-Leu.

Thus, in addition to preventing phenol binding, these mutations should promote the formation of the R6 form of the protein thereby mimicking phenol binding) for two distinct reasons. First, the B5Phe mutation should destabilize the monomeric form of the protein (relative to the unfolded monomer) because the side chain of B5 is solvent exposed in the monomer and should stabilize the R6 form of the hexamer (relative to the wild type form of the R6 hexamer in the absence of phenol because it has formed a close interaction with other nonpolar side chains from other subunits which surround the phenol binding site, similar to the interactions normally made by phenol. Second, the B14-Phe mutation is sterically incapable of forming the normal T-state monomer structure, thereby providing a large driving force for formation of the R6 hexamer.

Thus, all the mutants described above under B14 substitutions, B5 substitutions and B14/B5 double substitutions should effect the stability of the monomer and the monomer:hexamer equilibrium as well as the T6←→T3R3←→R6 equilibria within the hexamer (although the T state should not be the canonical T state as seen in structural studies of the wild type monomer).

EXAMPLE 4

Global Redesigns for improved Stability

In these PDA designs ('trz'_06', 'trz_07b' and 'trz_08'), the insulin monomer was improved for stability. No consideration was given to the possible functional role of the mutations. For example, GlY-A1 is always designed to be A1-Asn, though this residue should be more conserved for function.

In general, PDA design 'trz_06' is more conservative than PDA designs 'trz_07b' and 'trz_08'. In all three PDA calculations, residues at the following positions were considered 'core' residues: A2, A3, A16, B11, B15, and B24; residues at the following positions were considered 'boundary' residues: A5, A15, A17, A19, A21, B2, B3, B4, B8, B12, B14, B18, B22, B26, and B28; residues at the following positions were considered 'surface' residues: A1, A4, A8, A9, A10, A12, A13, A14, A18, B1, B5, B6, B9, B10, B13, B16, B17, B21, B25, B27, B29, and B30.

A preferred IA protein sequence from the PDA calculation 'trz_06' is shown in FIG. 5A. This sequence shows 6 mutations when compared to the wild type insulin sequence, G-A1-N, I-A10-Q, L-A16-Y, F-B1-D, F-B25N, and T-B27-D.

A preferred IA protein sequence from the PDA calculation 'trz_07b' is shown in FIG. 5B. This sequence shows 14 mutations when compared to the wild type insulin sequence, G-A1-N, I-A10-Q, L-A16-Y, E-A17-Y, Y-A19-F, F-B1-D, V-B2-K, Q-B4-F, L-B11-I, V-B12-R, A-B14W, F-B25-N, Y-B26-F and T-B27-D.

A preferred IA protein sequence from the PDA calculation 'trz_08' is shown in FIG. 5C. This sequence shows 16 mutations when compared to the wild type insulin sequence, G-A1-N, I-A10-Q, L-A16-Y, E-A17-Y, Y-A19-F, F-B1-D, V-B2-K, Q-B4-F, G-B8L, L-B11-I, V-B12-R, A-B14-W, F-B25-N, Y-B26-F, T-B27-D and P-B28-N.

As note in the PDA design to promote hexamer binding (see Example 3), Trp at position B14 replaces Ala in PDA designs 'trz_07b' and 'trz_08'. There appears to be a small cleft between the B-chain helix and the A-chain strand that accommodates Trp binding. This is the same cleft used in the hexamer design in Example 3.

Other preferred mutations for the A-chain are as follows: 1Asn, 10Gln, 16Tyr, 17Tyr, 17Lys, 17Trp, and 19Phe.

Other preferred mutations for the B-chain are as follows: 1Asp, 2Lys, 4Tyr, 4Phe, 8Leu, 8Lys, 12Arg, 14Trp, 14Glu, 18Lys, 25Asn, 26Phe, 27Asp, 28Asn and 28Phe.

Using Monte Carlo technique a list of low energy sequences was generated. The analysis of the lowest 1000 protein sequences generated by Monte Carlo leads to the mutation pattern are shown in the Table 4:

| # | consensus | probability table (x1000) | | | |
|---|---|---|---|---|---|
| 1 (A1) | ASN 993 | ASN 1000 | | | |
| 2 (A2) | ILE 992 | ILE 1000 | | | |
| 3 (A3) | ILE 819 | VAL 180 | ILE 820 | | |
| 4 (A4) | GLN 874 | GLN 1000 | | | |
| 5 (A5) | GLU 376 | GLU 383 | GLN 329 | ARG 287 | |
| 8 (A8) | GLN 838 | ASP 154 | GLN 846 | | |
| 9 (A9) | ASN 858 | ASN 879 | GLN 121 | | |
| 10 (A10) | GLN 921 | GLN 1000 | | | |
| 12 (A12) | LYS 415 | THR 226 | GLN 332 | LYS 441 | |
| 13 (A13) | GLU 855 | GLU 1000 | | | |
| 14 (A14) | LYS 778 | LYS 846 | ARG 154 | | |
| 15 (A15) | GLU 324 | LEU 216 | GLU 346 | GLN 132 | ARG 306 |
| 16 (A16) | TYR 979 | TYR 1000 | | | |
| 17 (A17) | LYS 399 | TRP 410 | GLN 128 | LYS 463 | |
| 18 (A18) | SER 441 | SER 534 | GLU 213 | LYS 130 | ARG 124 |
| 19 (A19) | PHE 537 | PHE 543 | TYR 457 | | |
| 21 (A21) | ASN 412 | ASP 116 | ASN 470 | GLN 123 | ARG 291 |
| 22 (B1) | ASP 929 | ASP 1.0 | | | |
| 23 (B2) | LYS 930 | LYS 1000 | | | |
| 24 (B3) | ASN 998 | ASN 1000 | | | |
| 25 (B4) | PHE 672 | PHE 673 | TYR 327 | | |
| 26 (B5) | GLU 610 | GLU 646 | LYS 164 | ARG 190 | |
| 27 (B6) | GLU 309 | GLU 370 | GLN 266 | LYS 207 | ARG 157 |
| 29 (B8) | LYS 603 | LEU 245 | GLU 128 | LYS 627 | |
| 30 (B9) | ARG 593 | GLU 188 | GLN 169 | ARG 643 | |
| 31 (B10) | ARG 421 | GLU 256 | GLN 185 | ARG 559 | |
| 32 (B11) | ILE 674 | LEU 322 | ILE 678 | | |
| 33 (B12) | ARG 743 | LYS 219 | ARG 781 | | |
| 34 (B13) | GLU 607 | ASN 368 | GLU 632 | | |
| 35 (B14) | GLU 898 | TRP 102 | GLU 898 | | |
| 36 (B15) | LEU 1000 | LEU 1000 | | | |
| 37 (B16) | GLU 775 | GLU 880 | ARG 120 | | |
| 38 (B17) | LYS 728 | LYS 1000 | | | |
| 39 (B18) | VAL 652 | VAL 683 | LYS 317 | | |
| 42 (B21) | ARG 623 | GLN 123 | LYS 160 | ARG 717 | |
| 43 (B22) | GLN 877 | GLN 1000 | | | |
| 45 (B24) | TYR 975 | TYR 1000 | | | |
| 46 (B25) | ASN 989 | ASN 1000 | | | |
| 47 (B26) | PHE 1000 | PHE 1000 | | | |
| 48 (B27) | ASP 915 | ASP 1000 | | | |
| 49 (B28) | PHE 873 | ASN 123 | PHE 877 | | |
| 50 (B29) | THR 310 | SER 183 | THR 351 | ASN 219 | GLU 247 |
| 51 (B30) | SER 606 | ALA 251 | SER 749 | | |

Positions A6, A7, A11, A20, B7, and B19 are cysteines in the wild type sequence and are not included in the 'trz' series of PDA designs. Positions B20 and B23 are glycines are were also not included in these calculations. Positions that are critical for function can be constrained to wild type and combined with mutations from this table to give more stable IA proteins.

EXAMPLE 5

Measurable Properties that will reflect the Effect of Mutations in IA Proteins

The effect of the B14 and/or B5 substitutions can be measured by one or more of the following methods.

1. Metal binding.

Zn and Co binding geometry in the hexamer is measured by UV spectrophotometry of the Co species. The stabilization of the R state causes a well characterized spectral shift that depends on whether the conformation of insulin within the hexamer is in the R or T state [Nakagawa and Tager, Biochemistry 31(12):3204–3214 (1992); Brader et al., Biochemistry 30(27):6636–45 (1991)].

2. Association.

The increased tendency to form a hexameter a given insulin concentration is measured by methods known In the art, such as analytical ultra centrifugation, size exclusion chromatography, peptide circulardichroism and NMR spectrometry.

3. Conformation.

The increased R state conformation is detected using known methods in the art, such as circulardichroism, far UV measurement of increased helix content in the B-chain, and Trp fluorimetry. Structural changes to the R state can be detected by X-ray crystallography or NMER solution of the structure.

4. Stability.

Stability is measured using methods known in the art, such as isothermal titration calorimetry (e.g., Zn binding), thermal melts resistance to chemical inactivation, and guanidinium denaturation.

The increased stability of the hexamer form of these mutant insulins should provide longer shelf life and resistance to inactivation from environmental stress such as heat, light, or chemical denaturation. These effects will be measurable by accelerated shelf lifetesting assessed by e.g., chromatography and by chemical denaturation assessed by e.g., circular dichroism or fluorescence.

A stable insulin hexamer without phenol would also have useful pharmacological properties, such as delayed onset of action following administration subcutaneously or to the circulation.

the above described mutants should slow the dissociation of the hexamer in the bloodstream. Additionally, receptor affinity may be reduced.

Pharmacokinetics can be measured by injection of an IA protein into animals or humans followed by a glucose challenge at varying times afterward. Delayed onset of glucose blood level control would be observed. Receptor affinity can be measured with an adipocyte lipogenesis assayorin vitro using BioCore.

Standard Potency Assays (1) insulin radioreceptor assays are performed, in which the relative potency of an insulin is defined as the ratio of insulin to IA protein required to displace 50% od $^{125}$I-insulin specifically bound to insulin receptors present on cell membranes, e.g., rat liver plasma membrane fraction.

(2) Lipogenesis assays are performed, e.g., with rat adipocytes, in which relative insulin potency is defined as the ratio of insulin to IA protein required to achieve 50% of the maximum conversion of [$^3$H]glucose into organic-extractable material (i.e. lipids);.

(3) Glucose oxidation assays are performed in isolated fat cells in which the relative potency of the IA proteins is defined as the ratio of insulin to IA protein to achieve 50% of the maximum conversion of glucose-1-[$^{14}$C] into $^{14}CO_2$.

(4) Insulin radioimmunoassays are performed, which can determine the immunogenecity of IA proteins by measuring the effectiveness by which insulin or an IA protein competes with $^{125}$I-insulin in binding to specific anti-insulin antibodies.

(5) Other assays are performed that measure the binding of insulin or an IA protein to cells known to possess specific insulin receptors.

We claim:

1. A protein having insulin activity comprising an amino acid sequence of SEQ ID NO: 2, wherein said protein has at least one substitution selected from B4-Y and B4F.

2. A protein having insulin activity comprising an amino acid sequence of SEQ ID NO: 2 wherein said protein has at least one substitution selected from the group of B5-F, B5-W, B14-F, B14-W, B14-Y, and B14-L.

3. A protein having insulin activity comprising an amino acid sequence selected from the group of amino acid sequence shown in SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO; 17, SEQ ID NO: 18, SEQ ID NO: 19, SEQ ID NO: 20, SEQ ID NO: 21, SEQ ID NO: 22, SEQ SEQ ID NO: 23.

4. A recombinant nucleic acid encoding said protein of claim 3.

5. An expression vector comprising the recombinant nucleic acid of claim 4.

6. A host cell comprising the expression vector of claim 5.

7. A host cell comprising the recombinant nucleic acid of claim 4.

8. A method of producing a protein having insulin activity comprising culturing the host cell of claim 7 under conditions suitable for expression of said nucleic acid.

9. A method according to claim 8 further comprising recovering said protein.

10. A pharmaceutical composition comprising a protein according to claim 3 and a pharmaceutical carrier.

11. A protein according to claim 3 wherein said protein comprises the amino acid sequence shown in (SEQ ID NO: 7).

12. A protein having insulin activity comprising an amino acid sequence of SEQ ID NO: 2, wherein said protein comprises an least 2 amino acid substitutions from the A-chain and at least 5 amino acid substitutions from the B-chain and said substitutions are selected from the group consisting of A1N, A10Q, A16Y, A17Y, A17L, A17W, A17Q, A19F, B1D, B2E, B2T, B2K, B2Q, B2D, B2R, B2N, B2F, B4Y, B4F, B4E, B4K, B4R, B8L, B8L, B8K, B8E, B11I, B12R, B12K, B14F, B14W, B14Y, B14I, B14B, B14R, B14K, B14L, B25N, B26F, B27D, B28N, and B28F.

13. A protein according to claim 12, wherein said substitutions are selected from the group consisting of A1-N, A10-Q, A16-Y, A17-Y, A19-F, B1-D, B2-K, B4-F, B8-L, B11-I, B12-R, B14-W, B25-N, B26-F, B27-D, and B28-N.

14. A recombinant nucleic acid encoding the non-naturally occurring IA protein selected from the group consisting of: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, and SEQ ID NO: 23.

* * * * *

SEQUENCE LISTING

```
<160> NUMBER OF SEQ ID NOS: 23

<210> SEQ ID NO 1
<211> LENGTH: 110
<212> TYPE: PRT
<213> ORGANISM: Homo sapiens
<300> PUBLICATION INFORMATION:
<308> DATABASE ACCESSION NUMBER: P01308
<309> DATABASE ENTRY DATE: 1986-07-21
<313> RELEVANT RESIDUES: (1)..(110)

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gly His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80

Ala Leu Glu Gly Ser Leu Gly Lys Arg Gly Ile Val Glu Gln Cys Cys
                85                  90                  95

Thr Ser Ile Cys Ser Leu Tyr Gln Leu Glu Asn Tyr Cys Asn
                100                 105                 110

<210> SEQ ID NO 2
<211> LENGTH: 51
<212> TYPE: PRT
<213> ORGANISM: Homo sapiens
<300> PUBLICATION INFORMATION:
<308> DATABASE ACCESSION NUMBER: 229122
<309> DATABASE ENTRY DATE: 1992-07-10
<313> RELEVANT RESIDUES: (1)..(51)

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn Phe Val Asn Gln His Leu Cys Gly Ser His Leu
                20                  25                  30

Val Glu Ala Leu Tyr Leu Val Cys Gly Glu Arg Gly Phe Phe Tyr Thr
            35                  40                  45

Pro Lys Thr
    50

<210> SEQ ID NO 3
<211> LENGTH: 21
<212> TYPE: PRT
<213> ORGANISM: Homo sapiens
<300> PUBLICATION INFORMATION:
<301> AUTHORS: Ciszak, E. and Smith, G.D.
<302> TITLE: Crystallographic evidence for dual coordination around zinc
```

```
              in the T3R3 human insulin hexamer
<303> JOURNAL: Biochemistry
<304> VOLUME: 33
<305> ISSUE: 6
<306> PAGES: 1512-1517
<307> DATE: 1994-02-15
<308> DATABASE ACCESSION NUMBER: 494680
<309> DATABASE ENTRY DATE: 1993-11-19
<313> RELEVANT RESIDUES: (1)..(21)

<400> SEQUENCE: 3

Gly Ile Val Glu Gln Cys Cys Thr Ser Ile Cys Ser Leu Tyr Gln Leu
1               5                  10                  15

Glu Asn Tyr Cys Asn
            20

<210> SEQ ID NO 4
<211> LENGTH: 30
<212> TYPE: PRT
<213> ORGANISM: Homo sapiens
<300> PUBLICATION INFORMATION:
<301> AUTHORS: Ciszak, E. and Smith, G.D.
<302> TITLE: Crystallographic evidence for dual coordination around zinc
       in the T3R3 human insulin hexamer
<303> JOURNAL: Biochemistry
<304> VOLUME: 33
<305> ISSUE: 6
<306> PAGES: 1512-1517
<307> DATE: 1994-02-15
<308> DATABASE ACCESSION NUMBER: 494681
<309> DATABASE ENTRY DATE: 1993-11-19
<313> RELEVANT RESIDUES: (1)..(30)

<400> SEQUENCE: 4

Phe Val Asn Gln His Leu Cys Gly Ser His Leu Val Glu Ala Leu Tyr
1               5                  10                  15

Leu Val Cys Gly Glu Arg Gly Phe Phe Tyr Thr Pro Lys Thr
            20                  25                  30

<210> SEQ ID NO 5
<211> LENGTH: 21
<212> TYPE: PRT
<213> ORGANISM: Homo sapiens
<300> PUBLICATION INFORMATION:
<301> AUTHORS: Ciszak, E. and Smith, G.D.
<302> TITLE: Crystallographic evidence for dual coordination around zinc
       in the T3R3 human insulin hexamer
<303> JOURNAL: Biochemistry
<304> VOLUME: 33
<305> ISSUE: 6
<306> PAGES: 1512-1517
<307> DATE: 1994-02-15
<308> DATABASE ACCESSION NUMBER: 494682
<309> DATABASE ENTRY DATE: 1993-11-19
<313> RELEVANT RESIDUES: (1)..(21)

<400> SEQUENCE: 5

Gly Ile Val Glu Gln Cys Cys Thr Ser Ile Cys Ser Leu Tyr Gln Leu
1               5                  10                  15

Glu Asn Tyr Cys Asn
            20

<210> SEQ ID NO 6
<211> LENGTH: 30
<212> TYPE: PRT
<213> ORGANISM: Homo sapiens
<300> PUBLICATION INFORMATION:
<301> AUTHORS: Ciszak, E. and Smith, G.D.
<302> TITLE: Crystallographic evidence for dual coordination around zinc
       in the T3R3 human insulin hexamer
```

```
<303> JOURNAL: Biochemistry
<304> VOLUME: 33
<305> ISSUE: 6
<306> PAGES: 1512-1517
<307> DATE: 1994-02-15
<308> DATABASE ACCESSION NUMBER: 494683
<309> DATABASE ENTRY DATE: 1993-11-19
<313> RELEVANT RESIDUES: (1)..(30)

<400> SEQUENCE: 6

Phe Val Asn Gln His Leu Cys Gly Ser His Leu Val Glu Ala Leu Tyr
1               5                  10                  15

Leu Val Cys Gly Glu Arg Gly Phe Phe Tyr Thr Pro Lys Thr
            20                  25                  30

<210> SEQ ID NO 7
<211> LENGTH: 51
<212> TYPE: PRT
<213> ORGANISM: Artificial Sequence
<220> FEATURE:
<223> OTHER INFORMATION: synthetic

<400> SEQUENCE: 7

Asn Leu Val Glu Gln Ala Ser Thr Ser Gln Ala Ser Leu Tyr Gln Ile
1               5                  10                  15

Tyr Asn Phe Asp Asn Asp Val Asn Phe His Leu Tyr Gly Ser His Ile
            20                  25                  30

Arg Glu Trp Leu Tyr Leu Val Ala Gly Glu Arg Gly Phe Asn Phe Asp
        35                  40                  45

Pro Lys Thr
    50

<210> SEQ ID NO 8
<211> LENGTH: 51
<212> TYPE: PRT
<213> ORGANISM: Artificial Sequence
<220> FEATURE:
<223> OTHER INFORMATION: synthetic

<400> SEQUENCE: 8

Gly Ile Val Glu Gln Cys Ser Thr Ser Ile Cys Ser Leu Tyr Gln Leu
1               5                  10                  15

Glu Asn Tyr Cys Asn Phe Glu Asn Tyr His Leu Tyr Gly Ser His Leu
            20                  25                  30

Val Glu Ala Leu Tyr Leu Val Cys Gly Glu Arg Gly Phe Phe Tyr Thr
        35                  40                  45

Pro Lys Thr
    50

<210> SEQ ID NO 9
<211> LENGTH: 51
<212> TYPE: PRT
<213> ORGANISM: Artificial Sequence
<220> FEATURE:
<223> OTHER INFORMATION: synthetic

<400> SEQUENCE: 9

Gly Ile Val Glu Gln Cys Ser Thr Ser Ile Cys Ser Leu Tyr Gln Leu
1               5                  10                  15

Glu Asn Tyr Cys Asn Phe Val Asn Gln His Leu Asp Gly Ser His Leu
            20                  25                  30

Val Glu Ala Leu Tyr Leu Val Cys Gly Glu Arg Gly Phe Phe Tyr Thr
        35                  40                  45
```

-continued

Pro Lys Thr
    50

<210> SEQ ID NO 10
<211> LENGTH: 51
<212> TYPE: PRT
<213> ORGANISM: Artificial Sequence
<220> FEATURE:
<223> OTHER INFORMATION: synthetic

<400> SEQUENCE: 10

Gly Ile Val Glu Gln Cys Ser Thr Ser Ile Cys Ser Leu Tyr Gln Leu
1               5                   10                  15

Glu Asn Tyr Cys Asn Phe Thr Asn Tyr His Leu Tyr Gly Ser His Leu
            20                  25                  30

Val Glu Ala Leu Tyr Leu Val Cys Gly Glu Arg Gly Phe Phe Tyr Thr
        35                  40                  45

Pro Lys Thr
    50

<210> SEQ ID NO 11
<211> LENGTH: 51
<212> TYPE: PRT
<213> ORGANISM: Artificial Sequence
<220> FEATURE:
<223> OTHER INFORMATION: synthetic

<400> SEQUENCE: 11

Gly Ile Val Glu Gln Cys Ser Thr Ser Ile Cys Ser Leu Tyr Gln Leu
1               5                   10                  15

Glu Asn Tyr Cys Asn Phe Val Asn Tyr His Leu Tyr Gly Ser His Leu
            20                  25                  30

Val Glu Ala Leu Tyr Leu Val Cys Gly Glu Arg Gly Phe Phe Tyr Thr
        35                  40                  45

Pro Lys Thr
    50

<210> SEQ ID NO 12
<211> LENGTH: 51
<212> TYPE: PRT
<213> ORGANISM: Artificial Sequence
<220> FEATURE:
<223> OTHER INFORMATION: synthetic

<400> SEQUENCE: 12

Gly Ile Val Glu Gln Cys Ser Thr Ser Ile Cys Ser Leu Tyr Gln Leu
1               5                   10                  15

Glu Asn Tyr Cys Asn Phe Val Asn Gln His Leu Glu Gly Ser His Leu
            20                  25                  30

Val Glu Ala Leu Tyr Leu Val Cys Gly Glu Arg Gly Phe Phe Tyr Thr
        35                  40                  45

Pro Lys Thr
    50

<210> SEQ ID NO 13
<211> LENGTH: 47
<212> TYPE: PRT
<213> ORGANISM: Artificial Sequence
<220> FEATURE:
<223> OTHER INFORMATION: synthetic

<400> SEQUENCE: 13

-continued

Gly Ile Val Glu Gln Cys Glu Thr Ser Ile Cys Ser Leu Tyr Gln Leu
1               5                   10                  15

Glu Asn Tyr Cys Asn His Leu Glu Gly Ser His Leu Val Glu Ala Leu
            20                  25                  30

Tyr Leu Val Cys Gly Glu Arg Gly Phe Phe Tyr Thr Pro Lys Thr
            35                  40                  45

<210> SEQ ID NO 14
<211> LENGTH: 51
<212> TYPE: PRT
<213> ORGANISM: Artificial Sequence
<220> FEATURE:
<223> OTHER INFORMATION: synthetic

<400> SEQUENCE: 14

Gly Ile Val Glu Gln Cys Cys Thr Ser Ile Cys Ser Leu Tyr Gln Leu
1               5                   10                  15

Glu Asn Tyr Cys Asn Phe Val Asn Gln Phe Leu Cys Gly Ser His Leu
            20                  25                  30

Val Glu Phe Leu Tyr Leu Val Cys Gly Glu Arg Gly Phe Phe Tyr Thr
            35                  40                  45

Pro Lys Thr
    50

<210> SEQ ID NO 15
<211> LENGTH: 51
<212> TYPE: PRT
<213> ORGANISM: Artificial Sequence
<220> FEATURE:
<223> OTHER INFORMATION: synthetic

<400> SEQUENCE: 15

Gly Ile Val Glu Gln Cys Cys Thr Ser Ile Cys Ser Leu Tyr Gln Leu
1               5                   10                  15

Glu Asn Tyr Cys Asn Phe Val Asn Gln Phe Leu Cys Gly Ser His Leu
            20                  25                  30

Val Glu Ala Leu Tyr Leu Val Cys Gly Glu Arg Gly Phe Phe Tyr Thr
            35                  40                  45

Pro Lys Thr
    50

<210> SEQ ID NO 16
<211> LENGTH: 51
<212> TYPE: PRT
<213> ORGANISM: Artificial Sequence
<220> FEATURE:
<223> OTHER INFORMATION: synthetic

<400> SEQUENCE: 16

Gly Ile Val Glu Gln Cys Cys Thr Ser Ile Cys Ser Leu Tyr Gln Leu
1               5                   10                  15

Glu Asn Tyr Cys Asn Phe Val Asn Gln His Leu Cys Gly Ser His Leu
            20                  25                  30

Val Glu Phe Leu Tyr Leu Val Cys Gly Glu Arg Gly Phe Phe Tyr Thr
            35                  40                  45

Pro Lys Thr
    50

<210> SEQ ID NO 17
<211> LENGTH: 51

```
<212> TYPE: PRT
<213> ORGANISM: Artificial Sequence
<220> FEATURE:
<223> OTHER INFORMATION: synthetic

<400> SEQUENCE: 17

Gly Ile Val Glu Gln Cys Cys Thr Ser Ile Cys Ser Leu Tyr Gln Leu
1               5                   10                  15

Glu Asn Tyr Cys Asn Phe Val Asn Gln His Leu Cys Gly Ser His Leu
            20                  25                  30

Val Glu Trp Leu Tyr Leu Val Cys Gly Glu Arg Gly Phe Phe Tyr Thr
        35                  40                  45

Pro Lys Thr
    50

<210> SEQ ID NO 18
<211> LENGTH: 51
<212> TYPE: PRT
<213> ORGANISM: Artificial Sequence
<220> FEATURE:
<223> OTHER INFORMATION: synthetic

<400> SEQUENCE: 18

Gly Ile Val Glu Gln Cys Cys Thr Ser Ile Cys Ser Leu Tyr Gln Leu
1               5                   10                  15

Glu Asn Tyr Cys Asn Phe Val Asn Gln Phe Leu Cys Gly Ser His Leu
            20                  25                  30

Val Glu Trp Leu Tyr Leu Val Cys Gly Glu Arg Gly Phe Phe Tyr Thr
        35                  40                  45

Pro Lys Thr
    50

<210> SEQ ID NO 19
<211> LENGTH: 51
<212> TYPE: PRT
<213> ORGANISM: Artificial Sequence
<220> FEATURE:
<223> OTHER INFORMATION: synthetic

<400> SEQUENCE: 19

Gly Ile Val Glu Gln Cys Cys Thr Ser Ile Cys Ser Leu Tyr Gln Leu
1               5                   10                  15

Glu Asn Tyr Cys Asn Phe Val Asn Gln His Leu Cys Gly Ser His Leu
            20                  25                  30

Val Glu Tyr Leu Tyr Leu Val Cys Gly Glu Arg Gly Phe Phe Tyr Thr
        35                  40                  45

Pro Lys Thr
    50

<210> SEQ ID NO 20
<211> LENGTH: 51
<212> TYPE: PRT
<213> ORGANISM: Artificial Sequence
<220> FEATURE:
<223> OTHER INFORMATION: synthetic

<400> SEQUENCE: 20

Gly Ile Val Glu Gln Cys Cys Thr Ser Ile Cys Ser Leu Tyr Gln Leu
1               5                   10                  15

Glu Asn Tyr Cys Asn Phe Val Asn Gln His Leu Cys Gly Ser His Leu
            20                  25                  30
```

```
Val Glu Ile Leu Tyr Leu Val Cys Gly Glu Arg Gly Phe Phe Tyr Thr
         35                  40                  45

Pro Lys Thr
     50

<210> SEQ ID NO 21
<211> LENGTH: 51
<212> TYPE: PRT
<213> ORGANISM: Artificial Sequence
<220> FEATURE:
<223> OTHER INFORMATION: synthetic

<400> SEQUENCE: 21

Asn Ile Val Glu Gln Cys Cys Thr Ser Gln Cys Ser Leu Tyr Gln Tyr
1               5                   10                  15

Glu Asn Tyr Cys Asn Asp Val Asn Gln His Leu Cys Gly Ser His Leu
            20                  25                  30

Val Glu Ala Leu Tyr Leu Val Cys Gly Glu Arg Gly Phe Asn Tyr Asp
        35                  40                  45

Pro Lys Thr
    50

<210> SEQ ID NO 22
<211> LENGTH: 51
<212> TYPE: PRT
<213> ORGANISM: Artificial Sequence
<220> FEATURE:
<223> OTHER INFORMATION: synthetic

<400> SEQUENCE: 22

Asn Ile Val Glu Gln Cys Cys Thr Ser Gln Cys Ser Leu Tyr Gln Tyr
1               5                   10                  15

Tyr Asn Phe Cys Asn Asp Lys Asn Phe His Leu Cys Gly Ser His Ile
            20                  25                  30

Arg Glu Trp Leu Tyr Leu Val Cys Gly Glu Arg Gly Phe Asn Phe Asp
        35                  40                  45

Pro Lys Thr
    50

<210> SEQ ID NO 23
<211> LENGTH: 51
<212> TYPE: PRT
<213> ORGANISM: Artificial Sequence
<220> FEATURE:
<223> OTHER INFORMATION: synthetic

<400> SEQUENCE: 23

Asn Ile Val Glu Gln Cys Cys Thr Ser Gln Cys Ser Leu Tyr Gln Tyr
1               5                   10                  15

Tyr Asn Phe Cys Asn Asp Lys Asn Phe His Leu Cys Gly Ser His Ile
            20                  25                  30

Arg Glu Trp Leu Tyr Leu Val Cys Gly Glu Arg Gly Phe Asn Phe Asp
        35                  40                  45

Pro Lys Thr
    50
```